US009815776B2

(12) United States Patent
Narayanan et al.

(10) Patent No.: US 9,815,776 B2
(45) Date of Patent: Nov. 14, 2017

(54) SELECTIVE ANDROGEN RECEPTOR DEGRADER (SARD) LIGANDS AND METHODS OF USE THEREOF

(71) Applicants: GTX, INC., Memphis, TN (US); University of Tennessee Research Foundation, Knoxville, TN (US)

(72) Inventors: Ramesh Narayanan, Cordova, TN (US); Duane D. Miller, Collierville, TN (US); Thamarai Ponnusamy, Memphis, TN (US); Dong-Jin Hwang, Arlington, TN (US); Charles B. Duke, Memphis, TN (US); Christopher C. Coss, Upper Arlington, OH (US); Amanda Jones, Silver Spring, MI (US); James T. Dalton, Ann Arbor, MI (US)

(73) Assignees: UNIVERSITY OF TENNESSEE RESEARCH FOUNDATION, Knoxville, TN (US); GTX, INC., Memphis, TN (US)

( * ) Notice: Subject to any disclaimer, the term of this patent is extended or adjusted under 35 U.S.C. 154(b) by 0 days.

(21) Appl. No.: 15/135,151

(22) Filed: Apr. 21, 2016

(65) Prior Publication Data
US 2017/0050921 A1 Feb. 23, 2017

Related U.S. Application Data

(60) Provisional application No. 62/150,768, filed on Apr. 21, 2015, provisional application No. 62/220,094, filed on Sep. 17, 2015.

(51) Int. Cl.
C07C 255/58 (2006.01)
C07C 255/60 (2006.01)
(Continued)

(52) U.S. Cl.
CPC .......... *C07C 255/58* (2013.01); *A61K 9/0014* (2013.01); *A61K 31/277* (2013.01); *C07C 255/60* (2013.01); *C07B 2200/07* (2013.01)

(58) Field of Classification Search
None
See application file for complete search history.

(56) References Cited

U.S. PATENT DOCUMENTS

| 5,480,656 A | 1/1996 | Okada et al. |
| 5,575,987 A | 11/1996 | Kamei et al. |

(Continued)

FOREIGN PATENT DOCUMENTS

| CN | 1597662 A | 3/2005 |
| EP | 100172 A1 | 2/2004 |

(Continued)

OTHER PUBLICATIONS

Weiner, Arch Neurol. Mar. 1980;37(3):129-31.*

(Continued)

*Primary Examiner* — Karl J Puttlitz
(74) *Attorney, Agent, or Firm* — Mark S. Cohen; Pearl Cohen Zedek Latzer Baratz LLP

(57) ABSTRACT

This invention provides novel 3-amino propanamide selective androgen receptor degrader (SARD) compounds, pharmaceutical compositions and uses thereof in treating prostate cancer, advanced prostate cancer, castration resistant prostate cancer, androgenic alopecia or other hyperandrogenic dermal diseases, Kennedy's disease, amyotrophic lateral sclerosis (ALS), and uterine fibroids, and to methods for reducing the levels of androgen receptor-full length (AR-FL) including pathogenic or resistance mutations, AR-splice variants (AR-SV), and pathogenic polyglutamine (polyQ) polymorphisms of AR in a subject.

56 Claims, 13 Drawing Sheets

(51) Int. Cl.
A61K 9/00 (2006.01)
A61K 31/277 (2006.01)

(56) References Cited

U.S. PATENT DOCUMENTS

| | | | |
|---|---|---|---|
| 5,631,020 | A | 5/1997 | Okada et al. |
| 5,643,607 | A | 7/1997 | Okada et al. |
| 5,716,640 | A | 2/1998 | Kamei et al. |
| 5,814,342 | A | 9/1998 | Okada et al. |
| 6,036,976 | A | 3/2000 | Takechi et al. |
| 7,022,870 | B2 | 4/2006 | Dalton et al. |
| 7,118,552 | B2 | 10/2006 | Shaw et al. |
| 7,220,247 | B2 | 5/2007 | Shaw et al. |
| 7,500,964 | B2 | 3/2009 | Shaw et al. |
| 7,741,371 | B2 | 6/2010 | Dalton et al. |
| 8,735,440 | B2 | 5/2014 | McKnight et al. |
| 9,550,742 | B2 | 1/2017 | Marugan et al. |
| 2006/0142387 | A1 | 6/2006 | Cadilla et al. |
| 2006/0173037 | A1 | 8/2006 | Schlienger et al. |
| 2006/0241180 | A1 | 10/2006 | Dalton et al. |
| 2007/0049629 | A1 | 3/2007 | Scanlan et al. |
| 2007/0123563 | A1 | 5/2007 | Dalton et al. |
| 2007/0173546 | A1 | 7/2007 | Dalton et al. |
| 2008/0293766 | A1 | 11/2008 | Diamond et al. |
| 2009/0042844 | A1 | 2/2009 | Labrie et al. |
| 2009/0060873 | A1 | 3/2009 | Sporn et al. |
| 2009/0142323 | A1 | 6/2009 | Quarles et al. |
| 2011/0028719 | A1 | 2/2011 | Slon-Usakiewicz |
| 2014/0018433 | A1 | 1/2014 | Dalton et al. |
| 2014/0094474 | A1 | 4/2014 | Tormakangas et al. |

FOREIGN PATENT DOCUMENTS

| | | | |
|---|---|---|---|
| WO | WO 02/16310 A1 | | 2/2002 |
| WO | WO 2002/046164 A1 | | 6/2002 |
| WO | 03/106401 | * | 12/2003 |
| WO | WO 03/106401 A1 | | 12/2003 |
| WO | 2005/000794 | * | 1/2005 |
| WO | WO 2005000794 A1 | | 1/2005 |
| WO | WO 2007/005887 A2 | | 1/2007 |
| WO | WO 2007/126988 A2 | | 11/2007 |
| WO | WO 2008/011072 A2 | | 1/2008 |
| WO | WO 2008/124000 A2 | | 10/2008 |
| WO | WO 2009/010480 A1 | | 1/2009 |
| WO | WO 2009/069736 A1 | | 6/2009 |
| WO | WO 2009/082437 A2 | | 7/2009 |
| WO | WO 2012/007644 A1 | | 1/2012 |
| WO | WO 2014/113260 A1 | | 7/2014 |
| WO | WO 2015/042297 A1 | | 3/2015 |

OTHER PUBLICATIONS

Maclean, J Neurol Sci. Feb. 1996;135(2):149-57.*
Andersen et al. "Regression of castrate-recurrent prostate cancer by a small-molecule inhibitor of the amino-terminus domain of the androgen receptor" Cancer cell. Jun. 15, 2010;17(6):535-46.
Antonarakis et al. "AR-V7 and resistance to enzalutamide and abiraterone in prostate cancer" New England Journal of Medicine, Sep. 11, 2014;371(11)1028-38.
Attard et al. "Selective inhibition of CYP17 with abiraterone acetate is highly active in the treatment of castration-resistant prostate cancer" Journal of clinical oncology. May 26, 2009;27(23):3742-8.
Baek et al. "Ligand-specific allosteric regulation of coactivator functions of androgen receptor in prostate cancer cells" Proceedings of the National Academy of Sciences of the United States of America. Feb. 28, 2006;103(9):3100-5.
Berrevoets et al. "Effects of antiandrogens on transformation and transcription activation of wild-type and mutated (LNCaP) androgen receptors" The Journal of steroid biochemistry and molecular biology. Dec. 31, 1993;46(6):731-6.
Bohl et al. "Structural basis for antagonism and resistance of bicalutamide in prostate cancer" Proceedings of the National Academy of Sciences. Apr. 26, 2005;102(17):6201-6.

Bohl et al. "Structural basis for accommodation of nonsteroidal ligands in the androgen receptor" Journal of Biological Chemistry. Nov. 11, 2005;280(45):37747-54.
Claessens et al. "Diverse roles of androgen receptor (AR) domains in AR-mediated signaling" Nuclear receptor signaling. Jun. 27, 2008;6:e008.
Clegg et al. "ARN-509: a novel antiandrogen for prostate cancer treatment" Cancer research. Mar. 15, 2012;72(6):1494-503.
De Bono et al. "Abiraterone and increased survival in metastatic prostate cancer" New England Journal of Medicine, May 26, 2011:364(21):1995-2005.
Dehm et al. "Alternatively spliced androgen receptor Variants" Endocrine-related cancer. Oct. 1, 2011; (5):R183-96.
Dehm et al. "Splicing of a novel androgen receptor exon generates a constitutively active androgen receptor that mediates prostate cancer therapy resistance" Cancer research. Jul. 1, 2008;68(13):5469-77.
Hu et al. "Distinct transcriptional programs mediated by the ligand-dependent full-length androgen receptor and its splice variants in castration-resistant prostate cancer" Cancer research. Jul. 15, 2012;72(14):3457-62.
International Search Report for PCT Application No. PCT/US16/28623 dated Jun. 30, 2016.
Klotz L. "Maximal androgen blockade for advanced prostate cancer" Best Practice & Research Clinical Endocrinology 8, Metabolism. Apr. 30, 2008;22(2):331-40.
Li et al. "Androgen receptor splice variants mediate enzalutamide resistance in castration-resistant prostate cancer cell lines" Cancer research. Jan. 15, 2013;73(2):483-9.
Marhefka et al. "Homology modeling using multiple molecular dynamics simulations and docking studies of the human androgen receptor ligand binding domain bound to testosterone and nonsteroidal ligands" Journal of medicinal chemistry. May 24, 2001:44(11):1729-40.
McGinley et al. "Circumventing anti-androgen resistance by molecular design" Journal of the American Chemical Society. Apr. 4, 2007;129(13):3822-3.
Mitsiades N. "A road map to comprehensive androgen receptor axis targeting for castration-resistant prostate cancer" Cancer research. Aug. 1, 2013;73(15):4599-605.
Monge et al. "Unfaithfulness and promiscuity of a mutant androgen receptor in a hormone-refractory prostate cancer" Cellular and molecular life sciences. Feb. 1, 2006;63(4):487-97.
Nazareth et al. "Activation of the human androgen receptor through a protein kinase A signaling pathway" Journal of Biological Chemistry. Aug. 16, 1996;271(33):19900-7.
Nyquist et al. "TALEN-engineered AR gene rearrangements reveal endocrine uncoupling of androgen receptor in prostate cancer" Proceedings of the National Academy of Sciences. Oct. 22, 2013;110(43):17492-7.
Sadar MD. "Androgen-independent induction of prostate-specific antigen gene expression via cross-talk between the androgen receptor and protein kinase A signal transduction pathways" Journal of Biological Chemistry. Mar. 19, 1999;274(12):7777-83.
Sadar et al. "Ligand-independent activation of the androgen receptor by the differentiation agent butyrate in human prostate cancer cells" Cancer research. Oct. 15, 2000;60(20):5825-31.
Sartor et al. "Androgen receptor variant-7: an important predictive biomarker in castrate resistant prostate cancer" Asian journal of andrology. May 2015;17(3):439.
Scher et al. "Increased survival with enzalutamide in prostate cancer after chemotherapy" New England Journal of Medicine. Sep. 27, 2012;367(13):1187-97.
Sieber PR. "Treatment of bicalutamide-induced breast events" Expert review of anticancer therapy, Dec. 1, 2007;7(12):1773-9.
Siegel et al. "Cancer statistics" CA Cancer. J. Clin. 2014;64:9-29.
Tran et al. "Development of a second-generation antiandrogen for treatment of advanced prostate cancer" Science. May 8, 2009;324(5928):787-90.
Ueda et al. Ligand-independent activation of the androgen receptor by interleukin-6 and the role of steroid receptor coactivator-1 in prostate cancer cells: Journal of Biological Chemistry. Oct. 11, 2002;277(41):38087-94.

(56) References Cited

OTHER PUBLICATIONS

Xu et al. "hSSB1 binds and protects p21 from ubiquitin-mediated degradation and positively correlates with p21 in human hepatocellular carcinomas" Oncogene. May 12, 2011;30(19):2219-29.

Yamashita et al. "ASC-J9 suppresses castration-resistant prostate cancer growth through degradation of full-length and splice variant androgen receptors" Neoplasia. Jan. 1, 2012;14(1)74IN9-83IN12.

Yoshida et al. "Antiandrogen bicalutamide promotes tumor growth in a novel androgen-dependent prostate cancer xenograft model derived from a bicalutamide-treated patient" Cancer Research. Nov. 1, 2005;65(21):9611-6.

Zhou et al. "Study of the impact of the T877A mutation on ligand-induced helix-12 positioning of the androgen receptor resulted in design and synthesis of novel antiandrogens" Proteins: Structure; Function, and Bioinformatics. Feb. 15, 2010;78(3);623-37.

Bohl et al. "Aligand-based approach to identify quantitative structure-activity relationships for the androgen receptor" Journal of medicinal chemistry. Jul. 15, 2004;47(15):3765.

Danquah et al. "Combination therapy of antiandrogen and XIAP inhibitor for treating advanced prostate cancer" Pharmaceutical research. Aug. 1, 2012;29(8):2070-01.

Duke III, Charles B., et al. "Synthesis and biological studies of androgen receptor ligands: Towards mutation-resistant nonsteroidal antagonism." Abstracts of Papers of the American Chemical Society. vol. 240. 1155 16th St, NW, Washington, DC 20036 USA: Amer Chemical Soc, 2010.

Hwang et al. "Arylisothiacyanato selective androgen receptor modulators (SARMs) for prostate cancer" Bioorganic & medicinal chemistry. Oct. 1, 2006;14(19):6525-38.

Kim et al. "Ribosomal proteins as unrevealed caretakers for cellular stress and genomic instability" Oncotarget. Feb. 1, 2014;5(4):860-71.

Marhefka et al. "Design, synthesis, and biological characterization of metabolically stable selective androgen receptor modulators" Journal of medicinal chemistry. Feb. 12, 2004;47(4):993.

Wen et al. "LHRH-conjugated micelles for targeted delivery of antiandrogen to treat advanced prostate cancer" Pharmaceutical research. Oct. 1, 2014;31(10):2784-95.

* cited by examiner

E

F

SELECTIVE ANDROGEN RECEPTOR DEGRADER (SARD) LIGANDS AND METHODS OF USE THEREOF

CROSS REFERENCE TO RELATED APPLICATIONS

This application claims the benefit of U.S. Ser. No. 62/220,094, filed on 17 Sep. 2015, and U.S. Ser. No. 62/150,768, filed on 21 Apr. 2015 which are incorporated in their entirety herein by reference.

FIELD OF THE INVENTION

This invention is directed to 3-amino-propanamide selective androgen receptor degrader (SARD) compounds, pharmaceutical compositions and uses thereof in treating prostate cancer, advanced prostate cancer, castration resistant prostate cancer, androgenic alopecia or other hyperandrogenic dermal diseases, Kennedy's disease, amyotrophic lateral sclerosis (ALS), and uterine fibroids, and to methods for reducing the levels of androgen receptor-full length (AR-FL) including pathogenic or resistance mutations, AR-splice variants (AR-SV), and pathogenic polyglutamine (polyQ) polymorphisms of AR in a subject.

BACKGROUND OF THE INVENTION

Prostate cancer (PCa) is one of the most frequently diagnosed noncutaneous cancers among men in the US and is the second most common cause of cancer deaths with more than 200,000 new cases and over 30,000 deaths each year in the United States. PCa therapeutics market is growing at an annual rate of 15-20% globally.

Androgen-deprivation therapy (ADT) is the standard of treatment for advanced PCa. Patients with advanced prostate cancer undergo ADT, either by luteinizing hormone releasing hormone (LHRH) agonists, LHRH antagonists or by bilateral orchiectomy. Despite initial response to ADT, disease progression is inevitable and the cancer emerges as castration-resistant prostate cancer (CRPC). Up to 30% of patients with prostate cancer that undergo primary treatment by radiation or surgery will develop metastatic disease within 10 years of the primary treatment. Approximately 50,000 patients a year will develop metastatic disease, which is termed metastatic CRPC (mCRPC).

Patients with CRPC have a median survival of 12-18 months. Though castration-resistant, CRPC is still dependent on the androgen receptor (AR) signaling axis for continued growth. The primary reason for CRPC re-emergence is re-activation of AR by alternate mechanisms such as 1) intracrine androgen synthesis, 2) AR splice variants (AR-SV) that lack ligand binding domain (LBD), 3) AR-LBD mutations with potential to resist AR antagonists (i.e., mutants that are not sensitive to inhibition by AR antagonists, and in some cases AR antagonists act as agonists of the AR bearing these LBD mutations); and 4) amplications of the AR gene within the tumor.

A critical barrier to progress in treating CRPC is that AR signaling inhibitors such as enzalutamide, bicalutamide, and abiraterone, acting through the LBD, fail to inhibit growth driven by the N-terminal domain (NTD)-dependent constitutively active AR-SV. Recent high-impact clinical trials with enzalutamide and abiraterone in CRPC patients demonstrated that 0% of AR-V7 (the predominant AR-SV) expressing patients responded to either of the treatments, indicating the requirement for next generation AR antagonists that target AR-SVs. In addition, a significant number of CRPC patients are becoming refractory to abiraterone or enzalutamide, emphasizing the need for next generation AR antagonists.

Current evidences demonstrate that CRPC growth is dependent on constitutively active AR including AR-SV's that lack the LBD such as AR-V7 and therefore cannot be inhibited by conventional antagonists. AR inhibition and degradation through binding to a domain that is distinct from the AR LBD provides alternate strategies to manage CRPC.

Molecules that degrade the AR prevent any inadvertent AR activation through growth factors or signaling pathways, or promiscuous ligand-dependent activation. In addition, molecules that inhibit the constitutive activation of AR-SVs are extremely important to provide extended benefit to CRPC patients.

Currently only a few chemotypes are known to degrade AR which include the SARDs ARN-509, AZD-3514, and ASC-J9. However, these molecules degrade AR indirectly at much higher concentrations than their binding coefficient and they fail to degrade the AR-SVs that have become in recent years the primary reason for resurgence of treatment-resistant CRPC.

This invention describes novel AR antagonists with unique pharmacology that strongly (high potency and efficacy) and selectively bind AR (better than known antagonists), antagonize AR, and degrade AR full length (AR-FL) and AR-SV. Selective androgen receptor degrader (SARD) compounds possess dual degradation and AR-SV inhibitory functions and hence are distinct from any available CRPC therapeutics. These novel selective androgen receptor degrader (SARD) compounds inhibit the growth of PCa cells and tumors that are dependent on AR-FL and AR-SV for proliferation.

SARDs have the potential to evolve as new therapeutics to treat CRPCs that are untreatable with any other antagonists. This unique property of degrading AR-SV has extremely important health consequences for prostate cancer. Till date only one molecule (EPI-001) is reported to bind to AR-NTD and inhibit AR function and PCa cell growth, albeit at lower affinity and inability to degrade the receptor. The SARDs reported herein also bind to AR-NTD and inhibit NTD-driven AR activity.

The positive correlation between AR and PCa and the lack of a fail-safe AR antagonist, emphasize the need for molecules that inhibit AR function through novel or alternate mechanisms and/or binding sites, and that can elicit antagonistic activities within an altered cellular environment.

Traditional antiandrogens such as bicalutamide and flutamide were approved for use in prostate cancer. Subsequent studies have demonstrated the utility of antiandrogens (e.g., flutamide, spironolactone, cyproterone acetate, finasteride and chlormadinone acetate) in androgen-dependent dermatological conditions such as androgenic alopecia (male pattern baldness), acne vulgaris, and hirsutism. Prepubertal castration prevents sebum production and androgenic alopecia but this can be reversed by use of testosterone, suggesting its androgen-dependence.

The AR gene has a polymorphism of glutamine repeats (polyQ) within exon 1 which when shortened may augment AR transactivation (i.e., hyperandrogenism). It has been found that shortened polyQ polymorphisms are more common in people with alopecia, hirsutism, and acne. Classic antiandrogens are undesirable for these purposes because they are ineffective through dermal dosing and their long-term systemic use raises the risks of untoward sexual effects such as gynecomastia and impotence. Further, similar to CPRC discussed above, inhibition of ligand-dependent AR activity alone may not be sufficient as AR can be activated by various cellular factors other than the endogenous androgens testosterone (T) and dihydrotestosterone (DHT), such as growth factors, kinases, co-activator overexpression and/or promiscuous activation by other hormones (e.g., estrogens or glucocorticoids). Consequently, blocking the binding of T and DHT to AR with a classical antiandrogen may not be sufficient to have the desired efficacy.

An emerging concept is the topical application of a SARD to destroy the AR locally to the affected areas of the skin or other tissue without exerting any systemic antiandrogenism. For this use, a SARD that does not penetrate the skin or is rapidly metabolized would be preferable.

Supporting this approach is the observation that cutaneous wound healing has been demonstrated to be suppressed by androgens. Castration of mice accelerates cutaneous wound healing while attenuating the inflammation in the wounds. The negative correlation between androgen levels and cutaneous healing and inflammation, in part, explains another mechanism by which high levels of endogenous androgens exacerbate hyperandrogenic dermatological conditions. Further, it provides a rationale for the treatment of wounds such as diabetic ulcers or even trauma, or skin disorders with an inflammatory component such as acne or psoriasis, with a topical SARD.

Androgenic alopecia occurs in ~50% of Caucasian males by midlife and up to 90% by 80 years old. Minoxidil (a topical vasodilator) and finasteride (a systemic 5alpha reductase type II inhibitor) are FDA approved for alopecia but require 4-12 months of treatment to produce a therapeutic effect and only arrest hair loss in most with mild to moderate hair regrowth in 30-60%. Since currently available treatments have slow and limited efficacy that varies widely between individuals, and produce unwanted sexual side effects, it is important to find a novel approach to treat androgenic alopecia and other hyperandrogenic dermatologic diseases.

Amyotrophic lateral sclerosis (ALS) is a fatal neurodegenerative disease. Patients with ALS are characterized by extended AR polyglutamine repeats. Riluzole is an available drug for ALS treatment, however, only provides short-term effects. There is an urgent need for drugs that extend the survival of ALS patients. Transgenic animals of ALS were shown to survive longer upon castration and reduction in AR levels compared to castration+nandrolone (agonist) supplementation. Castration reduces the AR level, which may be the reason for extended survival.

Androgens promote uterine proliferation. Higher testosterone levels increase the risk of uterine fibroids. Treatment of uterine fibroids with SARDs would help prevent or treat uterine fibroids.

Here we describe 3-amino-propanamide SARDs that bind to LBD and an alternate binding and degradation domain (BDD; located in the NTD), antagonize AR, and degrade AR thereby blocking ligand-dependent and ligand-independent AR activities. This novel mechanism produces improved efficacy when dosed systemically (e.g., for prostate cancer) or topically (e.g., dermatological diseases). X-linked spinal-bulbar muscular atrophy (SBMA—also known as Kennedy's disease) is a muscular atrophy that arises from a defect in the androgen receptor gene on the X chromosome. Proximal limb and bulbar muscle weakness results in physical limitations including dependence on a wheelchair in some cases. The mutation results in a protracted polyglutamine tract added to the N-terminal domain of the androgen receptor (polyQ AR). Binding and activation of this lengthened polyQ AR by endogeneous androgens (testosterone and DHT) results in unfolding and nuclear translocation of the mutant androgen receptor. These steps are required for pathogenesis and result in partial loss of transactivation function (i.e., an androgen insensitivity) and a poorly understood neuromuscular degeneration. Currently there are no disease-modifying treatments but rather only symptom directed treatments. Efforts to target the polyQ AR of Kennedy's disease as the proximal mediator of toxicity by harnessing cellular machinery to promote its degradation, i.e., through the use of a SARD, hold promise for therapeutic intervention. Selective androgen receptor degraders such as those reported herein bind to and degrade a variety of androgen receptors (full length, splice variant, antiandrogen resistance mutants, and are likely to degrade polyQ AR polymorphism as well), indicating that they are promising leads for treatment of SBMA.

SUMMARY OF THE INVENTION

In one embodiment, this invention provides a selective androgen receptor degrader (SARD) compound represented by the structure of formula I:

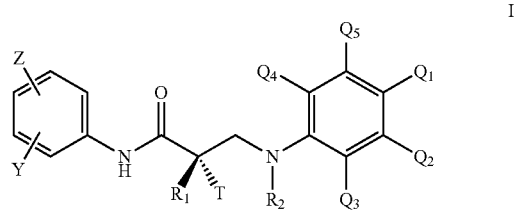

wherein
T is OH, OR, —NHCOCH$_3$, or NHCOR;
Z is NO$_2$, CN, COOH, COR, NHCOR or CONHR;
Y is CF$_3$, F, I, Br, Cl, CN, C(R)$_3$ or Sn(R)$_3$;
R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH;
R$_1$ is CH$_3$, CH$_2$F, CHF$_2$, CF$_3$, CH$_2$CH$_3$, or CF$_2$CF$_3$;
R$_2$ is hydrogen, C$_1$-C$_{12}$-alkyl, —SO$_2$-aryl, —SO$_2$-phenyl, —CO-aryl, arylalkyl, substituted or unsubstituted benzyl, substituted or unsubstituted aryl, or C$_3$-C$_7$-cycloalkyl;
Q$_1$, Q$_2$, Q$_3$, Q$_4$, and Q$_5$ are each independently selected from hydrogen, substituted or unsubstituted linear or branched alkyl, substituted or unsubstituted aryl, substituted or unsubstituted phenyl, F, Cl, Br, I, CF$_3$, CN, NO$_2$, substituted or unsubstituted cycloalkyl, substituted or unsubstituted heterocycloalkyl, substituted or unsubstituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO, or OCN;
wherein at least two of Q$_1$, Q$_2$, Q$_3$, Q$_4$, and Q$_5$ are not hydrogens; or
Q$_1$ and Q$_2$ are joined together to form a substituted or unsubstituted C$_5$-C$_8$ carbocyclic or heterocyclic ring, and Q$_3$, Q$_4$, and Q$_5$ are as defined above; or Q$_2$ and Q$_3$ are joined together to form a substituted or unsubstituted C$_5$-C$_8$ carbocyclic or heterocyclic ring, and Q$_1$, Q$_4$, and Q$_5$ are as defined above; and wherein said formed carbocyclic or heterocyclic ring is not dihydropyridin-2(1H)-one, pyridin-2(1H)-one or 1H-pyrrole.

In another embodiment, the selective androgen receptor degrader (SARD) compound is represented by the structure of formula III:

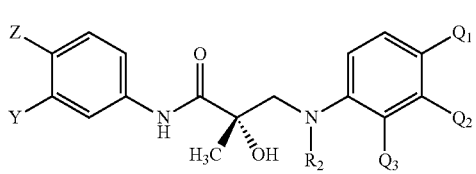

wherein
Z is $NO_2$ or CN;
Y is $CF_3$, F, I, Br, Cl, or CN;
$R_2$ is hydrogen, $C_1$-$C_{12}$-alkyl, —$SO_2$-aryl, —$SO_2$-phenyl, —CO-aryl, substituted or unsubstituted arylalkyl, substituted or unsubstituted benzyl, substituted or unsubstituted aryl, or substituted or unsubstituted $C_3$-$C_7$-cycloalkyl;
$Q_1$, $Q_2$ and $Q_3$ are each independently selected from hydrogen, substituted or unsubstituted aryl, substituted or unsubstituted phenyl, substituted or unsubstituted arylalkyl, F, Cl, Br, I, $CF_3$, CN, $NO_2$, substituted or unsubstituted cycloalkyl, or substituted or unsubstituted heterocycloalkyl;
wherein least one of $Q_1$, $Q_2$ and $Q_3$ is a substituted or unsubstituted aryl, substituted or unsubstituted arylalkyl, or substituted or unsubstituted phenyl;
or
$Q_1$ and $Q_2$ are joined together to form a substituted or unsubstituted $C_5$-$C_8$ carbocyclic or heterocyclic ring and $Q_3$ is as defined above;
or
$Q_2$ and $Q_3$ are joined together to form a substituted or unsubstituted $C_5$-$C_8$ carbocyclic or heterocyclic ring and $Q_1$ is as defined above; and
wherein said formed carbocyclic or heterocyclic ring is not dihydropyridin-2(1H)-one, pyridin-2(1H)-one or 1H-pyrrole.

In one embodiment, this invention is directed to a selective androgen receptor degrader (SARD) compound represented by the structure of formula IV:

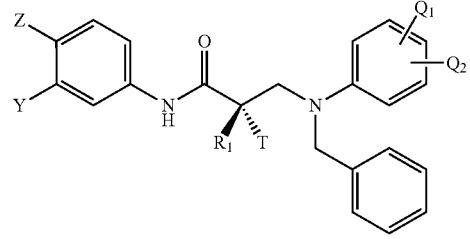

wherein
T is OH, OR, —$NHCOCH_3$, or NHCOR;
Z is $NO_2$, CN, COOH, COR, NHCOR or CONHR;
Y is $CF_3$, F, I, Br, Cl, CN, $C(R)_3$ or $Sn(R)_3$;
R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;
$R_1$ is $CH_3$, $CH_2F$, $CHF_2$, $CF_3$, $CH_2CH_3$, or $CF_2CF_3$;
$Q_1$ is hydrogen, substituted or unsubstituted linear or branched alkyl, substituted or unsubstituted aryl, substituted or unsubstituted phenyl, F, Cl, Br, I, $CF_3$, CN, $NO_2$, substituted or unsubstituted cycloalkyl, substituted or unsubstituted heterocycloalkyl, substituted or unsubstituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO, or OCN;
$Q_2$ is hydrogen, substituted or unsubstituted linear or branched alkyl, substituted or unsubstituted aryl, substituted or unsubstituted phenyl, F, Cl, Br, I, $CF_3$, CN, $NO_2$, substituted or unsubstituted cycloalkyl, substituted or unsubstituted heterocycloalkyl, substituted or unsubstituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO, or OCN;
or
$Q_1$ and $Q_2$ are joined together to form a substituted or unsubstituted $C_5$-$C_8$ carbocyclic or heterocyclic ring.

In one embodiment, this invention is directed to a selective androgen receptor degrader (SARD) compound represented by the structure of formula VII:

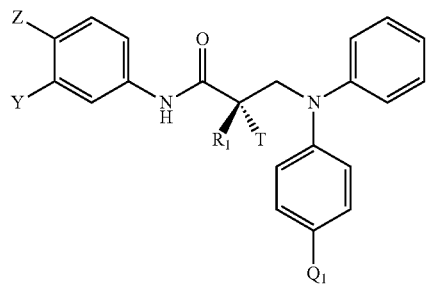

wherein
T is OH, OR, —$NHCOCH_3$, or NHCOR;
Z is $NO_2$, CN, COOH, COR, NHCOR or CONHR;
Y is $CF_3$, F, I, Br, Cl, CN, $C(R)_3$ or $Sn(R)_3$;
R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;
$R_1$ is $CH_3$, $CH_2F$, $CHF_2$, $CF_3$, $CH_2CH_3$, or $CF_2CF_3$; and
$Q_1$ is hydrogen, substituted or unsubstituted linear or branched alkyl, substituted or unsubstituted aryl, substituted or unsubstituted phenyl, F, Cl, Br, I, $CF_3$, CN, $NO_2$, substituted or unsubstituted cycloalkyl, substituted or unsubstituted heterocycloalkyl, substituted or unsubstituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO, or OCN.

In another embodiment, $Q_1$ of formulas I, III, IV or VII is CN. In another embodiment, $Q_2$ and $Q_3$ of formulas III and IV are joined together to form a substituted or unsubstituted $C_5$-$C_8$ carbocyclic or heterocyclic ring. In another embodiment, $Q_1$ of formula VII is F or $NO_2$.

In another embodiment, the SARD compound of this invention is represented by the structure of any one of the following compounds:
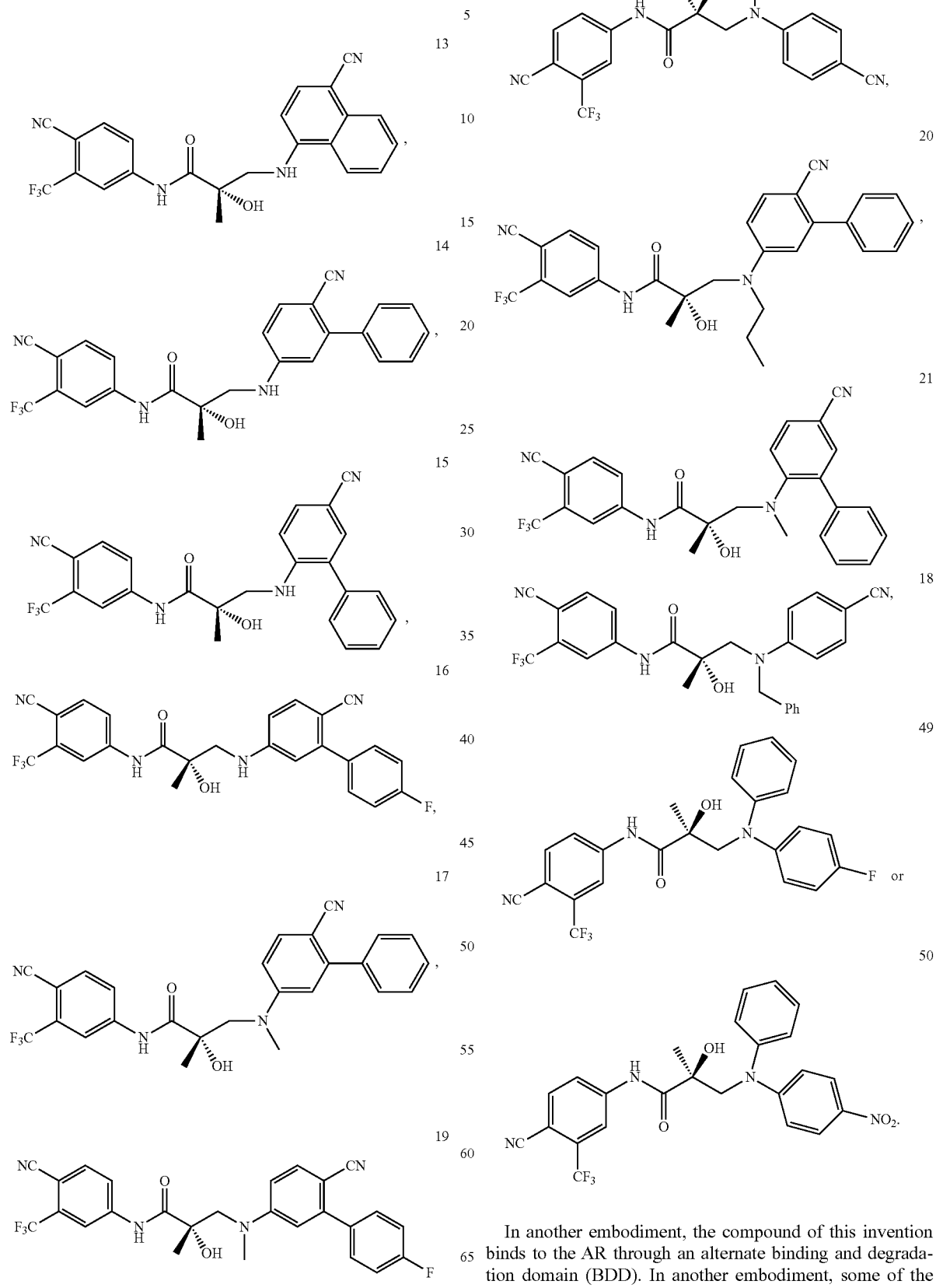
In another embodiment, the compound of this invention binds to the AR through an alternate binding and degradation domain (BDD). In another embodiment, some of the compounds of this invention further bind the AR ligand binding domain (LBD). In another embodiment, the compound exhibits AR-splice variant (AR-SV) degradation activity. In another embodiment, the compound further exhibits AR-full length (AR-FL) degradation activity. In another embodiment, the compound exhibits AR-SV inhibitory activity (i.e., is an AR-SV antagonist). In another embodiment, the compound further exhibits AR-FL inhibitory activity (i.e., is an AR-FL antagonist). In another embodiment, the compound possesses dual AR-SV degradation and AR-SV inhibitory functions. In another embodiment, the compound further possesses dual AR-FL degradation and AR-FL inhibitory functions.

In one embodiment, this invention is directed to a pharmaceutical composition comprising a SARD compound according to this invention, or its isomer, pharmaceutically acceptable salt, pharmaceutical product, polymorph, hydrate or any combination thereof, and a pharmaceutically acceptable carrier. In another embodiment, the pharmaceutical composition is formulated for topical use. In another embodiment, the pharmaceutical composition is in the form of a solution, lotion, salve, cream, ointment, liposome, spray, gel, foam, roller stick, cleansing soaps or bars, emulsion, mousse, aerosol, shampoo, or any combination thereof.

In one embodiment, this invention is directed to a method of treating, suppressing, reducing the incidence, reducing the severity, or inhibiting the progression of prostate cancer (PCa) and its symptoms, or increasing the survival of a male subject suffering from prostate cancer comprising administering to said subject a therapeutically effective amount of a compound according to this invention, or its isomer, pharmaceutically acceptable salt, pharmaceutical product, polymorph, hydrate or any combination thereof. In another embodiment, the prostate cancer is advanced prostate cancer, castration resistant prostate cancer (CRPC), metastatic CRPC (mCRPC), non-metastatic CRPC (nmCRPC), high-risk nmCRPC or any combination thereof. In one embodiment, this invention is directed to a method of treating, suppressing, reducing the incidence, reducing the severity, or inhibiting the progression of advanced prostate cancer and its symptoms, or increasing the survival of a male subject suffering from advanced prostate cancer comprising administering to said subject a therapeutically effective amount of a compound of this invention, or its isomer, pharmaceutically acceptable salt, pharmaceutical product, polymorph, hydrate or any combination thereof.

In one embodiment, this invention is directed to a method of treating, suppressing, reducing the incidence, reducing the severity, or inhibiting the progression of castration resistant prostate cancer (CRPC) and its symptoms, or increasing the survival of a male subject suffering from castration resistant prostate cancer comprising administering to said subject a therapeutically effective amount of a compound of this invention, or its isomer, pharmaceutically acceptable salt, pharmaceutical product, polymorph, hydrate or any combination thereof.

In another embodiment, the prostate cancer depends on AR-SV for proliferation. In another embodiment, the prostate cancer further depends on AR-FL for proliferation. In another embodiment, the AR-SV is AR-V7 or ARv567es. In another embodiment, the prostate cancer depends on AR that contains the W741L mutation or T877A mutation or other antiandrogen resistance-conferring AR-LBD mutations, or any combination thereof. In another embodiment, the prostate cancer depends on amplications of the AR gene within the tumor. In another embodiment, there may be a heterogenous expression of AR such that the prostate cancer may depend on multiple AR variations and/or amplifications within a single patient. In another embodiment, the subject further receives androgen deprivation therapy (ADT). In another embodiment, the subject has failed androgen deprivation therapy (ADT). In another embodiment, the cancer is resistant to treatment with an androgen receptor antagonist. In another embodiment, the androgen receptor antagonist is enzalutamide, bicalutamide, abiraterone, ARN-509, AZD-3514, galeterone, ASC-J9, flutamide, hydroxyflutamide, nilutamide, cyproterone acetate, ketoconazole, spironolactone, or any combination thereof. In another embodiment, the administering of the compound reduces the levels of AR, AR-full length (AR-FL), AR-FL with antiandrogen resistance-conferring AR-LBD mutations, AR-splice variant (AR-SV), gene-amplified AR, or any combination thereof, in said subject.

In one embodiment, this invention is directed to a method of reducing the levels of AR-splice variants in a subject, comprising administering to said subject a therapeutically effective amount of a compound of this invention, or its isomer, pharmaceutically acceptable salt, pharmaceutical product, polymorph, hydrate or any combination thereof. In another embodiment, the method further reduces the levels of AR-full length in said subject. In another embodiment, the reduction is achieved by degradation, inhibition, or dual degradation and inhibitory functions of AR-splice variants (AR-SV) or AR-FL variations including antiandrogen resistance mutants such as W741L and T877A. In another embodiment, the reduction is further achieved by degradation, inhibition, or dual degradation and inhibitory function of AR-FL. In another embodiment, the reduction is further achieved by degradation or inhibition of AR from amplified AR gene within the tumor.

In one embodiment, this invention is directed to a method of treating, suppressing, reducing the incidence, reducing the severity, or inhibiting the progression of the Kennedy's disease in a subject, comprising administering to said subject a compound of this invention.

In one embodiment, this invention is directed to a method of: (a) treating, suppressing, reducing the incidence, reducing the severity, or inhibiting the progression of acne in a subject; (b) decreasing sebum production in a subject; (c) treating, suppressing, reducing the incidence, reducing the severity, or inhibiting the progression of hirsutism in a subject; (d) treating, suppressing, reducing the incidence, reducing the severity, or inhibiting the progression of alopecia in a subject; (e) treating, suppressing, reducing the incidence, reducing the severity, or inhibiting the progression of a hormonal condition in female; (f) treating, suppressing, reducing the incidence, reducing the severity, or inhibiting the progression of sexual perversion, hypersexuality, or paraphilias in a subject; (g) treating, suppressing, reducing the incidence, reducing the severity, or inhibiting the progression of androgen psychosis in a subject; (h) treating, suppressing, reducing the incidence, reducing the severity, or inhibiting the progression of virilization in a subject; (i) treating, suppressing, reducing the incidence, reducing the severity, or inhibiting the progression of androgen insensitivity syndrome in a subject; (j) increasing, modulating, or improving ovulation in an animal; (k) treating, suppressing, reducing the incidence, reducing the severity, or inhibiting the progression of cancer in a subject; or any combination thereof, comprising administering a compound of this invention or of a pharmaceutical composition thereof.

In one embodiment, this invention is directed to a method of reducing the levels of polyglutamine (polyQ) AR polymorphs in a subject comprising administering a compound according to this invention. In another embodiment, the reduction is achieved by degradation, inhibition, or dual degradation and inhibitory function of said polyglutamine (polyQ) AR polymorphs (polyQ-AR). In another embodiment, the polyQ-AR is a short polyQ polymorph or a long polyQ polymorph. In another embodiment, the polyQ-AR is a short polyQ polymorph, and the method further treats dermal disease. In another embodiment the polyQ-AR is a long polyQ polymorph, and said method further treats Kennedy's disease.

In one embodiment, this invention is directed to a method of treating, suppressing, reducing the incidence, reducing the severity, or inhibiting the progression of amyotrophic lateral sclerosis (ALS) in a subject, comprising administering a therapeutically effective amount of the compound of this invention, or its isomer, pharmaceutically acceptable salt, pharmaceutical product, polymorph, hydrate or any combination thereof; or a pharmaceutical composition thereof.

In one embodiment, this invention is directed to a method of treating, suppressing, reducing the incidence, reducing the severity, or inhibiting the progression of uterine fibroids in a subject, comprising administering a therapeutically effective amount of the compound of this invention, or its isomer, pharmaceutically acceptable salt, pharmaceutical product, polymorph, hydrate or any combination thereof; or a pharmaceutical composition thereof.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 11A: There are two tryptophan residues and up to 12 tyrosine residues. This has allowed us to study the folding properties of this domain using intrinsic steady state fluorescence emission spectra. Excitation at 287 nm excites both tyrosine and tryptophan residues. The emission maximum ($\lambda_{max}$) for the tryptophan is sensitive to the exposure to solvent. In the presence of the natural osmolyte TMAO (AF1+TMAO) there is a characteristic 'blue shift' consistent with the tryptophan residues being less solvent exposed and a loss of the shoulder (~307 nm; see solid black trace as compared to AF1 (alone) which is the $2^{nd}$ to top trace at 300 nm in the left panel and top trace at 300 nm in the right panel) for tyrosine as there is increased energy transfer to tryptophan as the polypeptide folds. In contrast in the presence of urea (causes unfolding) there is a 'red shift' as the tryptophan residues become more solvent exposed and a defined peak for tyrosine emission appears. To test if the compounds (enobosarm (E) and 17) interact with AF-1 and/or alter the folding of this domain we measured the steady state fluorescence for each compound with AR-AF1 alone or the presence of TMAO (3 M) or urea (4 or 6 M). Enobosarm was used as a negative control (should not interact) while TMAO serves as a positive control (should promote folding). We used 1 µM of AR-AF1 and 5 µM of the individual compounds and preincubated for at least 30 minutes prior to measuring the emission spectra. The emission spectra were all corrected for buffer alone or buffer with TMAO/urea/compounds as necessary. There was no dramatic effect of enobosarm (left panel) on the $\lambda_{max}$ for tryptophan, while 17 (right panel) reduces the wavelength (i.e., a 'blue shift'), indicating that 17 binds to the AF-1 and enobosarm does not bind to AF-1. Also the shoulder is missing on the AF1+TMAO+17 trace. FIG. 11B: Left Panel: A dose-dependent shift in the fluorescence intensity (i.e., quenching) by 17 was observed when incubated with AR AF-1. The fluorescence shoulder observed at 307 nm, which corresponds to tyrosine residues in the AF-1, is shifted by 17. The overall fluorescence is also markedly altered by 17. This indicates that 17 interacts with the AR AF-1 (in addition to the LBD binding demonstrated in other experiments). Right Panel. Data shown in the left panel was plotted as a difference in fluorescence plot between control and 17 treated samples (fluorescence in the absence of compound—fluorescence in the presence of compound), a dose dependent increase was observed in the presence of 17, again supporting that 17 interacts with the AR AF-1. AF1—activation function-1 which is a domain in the NTD of AR; TMAO—trimethylamine-N-oxide; E—enobosarm which is a selective androgen receptor modulator which does not bind NTD; 17—a selective androgen receptor degrader (SARD) of this invention.

Figure 1:
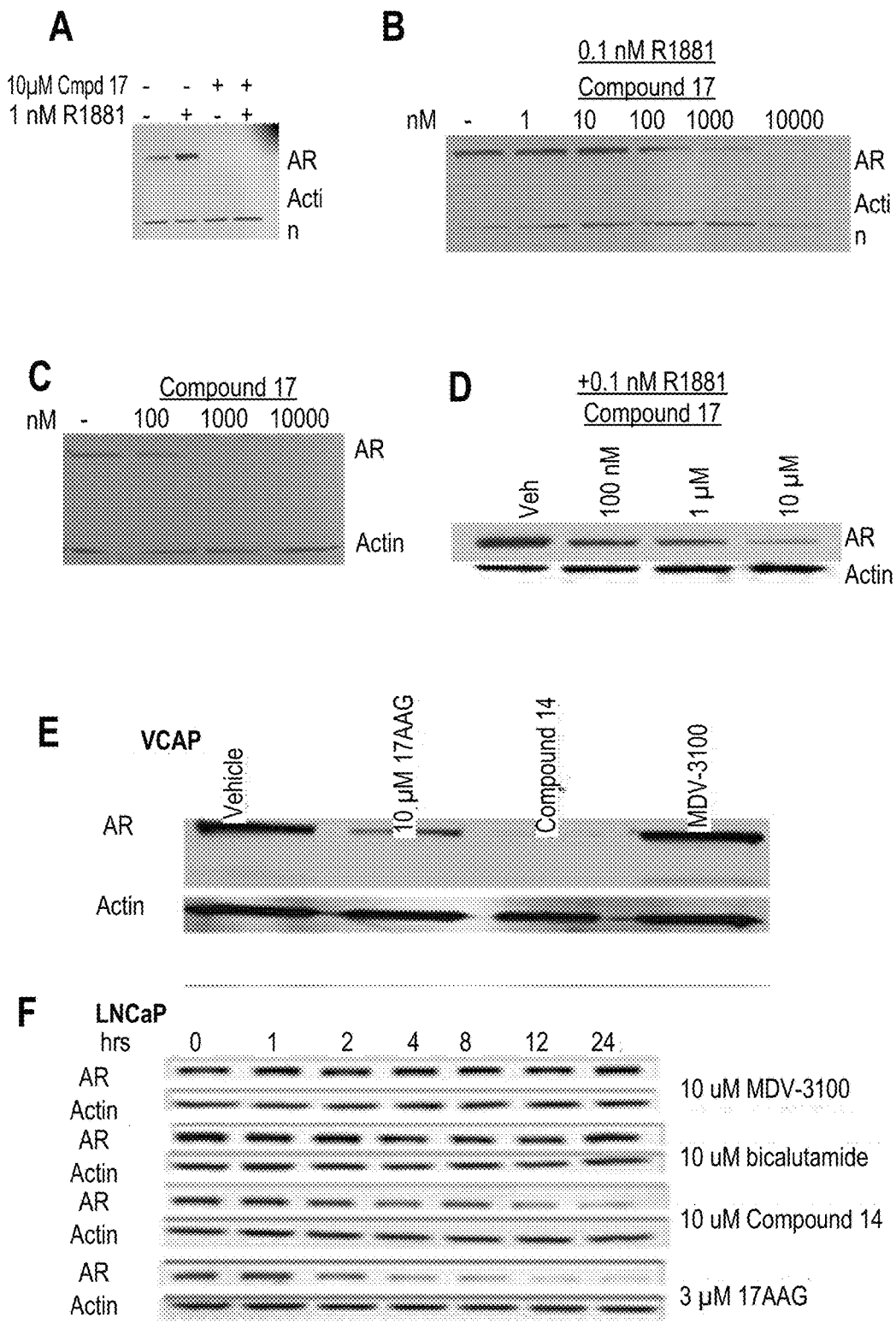
FIG. 1 depicts the effect of novel AR antagonists on AR protein levels (i.e. the SARD effect). (A) Serum-starved LNCaP cells treated with R1881 and SARD compound (17). (B) Dose response of 17 in the presence of 0.1 nM R1881 in LNCaP cells. (C) LNCaP cells were plated in full serum and treated with compound 17 (dose response). Cells were harvested, protein extracted, and Western blotted for AR and actin. (D) Effect of 17 on wild-type AR transfected into HeLa cells. (E) Effect of 14 on AR expression in VCaP. (F) Time-course response of AR to SARD (14) in LNCaP cells. 17-AAG-17-allylamino-17-demethoxygeldanamycin, a Hsp90 inhibitor. MDV-3100, an AR antagonist (antiandrogen) also known as enzalutamide. AR—androgen receptor; R1881—an AR agonist.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Androgens act in cells by binding to the AR, a member of the steroid receptor superfamily of transcription factors. As the growth and maintenance of prostate cancer (PCa) is largely controlled by circulating androgens, treatment of PCa heavily relies on therapies that target AR. Treatment with AR antagonists such as enzalutamide, bicalutamide or hydroxyflutamide to disrupt receptor activation has been successfully used in the past to reduce PCa growth. All currently available AR antagonists competitively bind AR and recruit corepressors such as NCoR and SMRT to repress transcription of target genes. However, altered intracellular signaling, AR mutations, and increased expression of coactivators lead to functional impairment of antagonists or even transformation of antagonists into agonists. Studies have demonstrated that mutation of W741 and T877 within AR converts bicalutamide and hydroxyflutamide, respectively, to agonists. Similarly, increased intracellular cytokines recruit coactivators instead of corepressors to AR-responsive promoters subsequently converting bicalutamide to an agonist.

Despite initial response to androgen deprivation therapy (ADT), PCa disease progression is inevitable and the cancer emerges as castration-resistant prostate cancer (CRPC). The primary reason for castration resistant prostate cancer (CRPC) re-emergence is re-activation of androgen receptor (AR) by alternate mechanisms such as:
  (a) intracrine androgen synthesis;
  (b) expression of AR splice variants (AR-SV) that lack ligand binding domain (LBD);

(c) AR-LBD mutations with potential to resist antagonists;
(d) hyper-sensitization of AR to low androgen levels, e.g., due to AR gene amplification or AR mutation;
(e) amplication of the AR gene within the tumor; and
(f) over expression of coactivators.

In one embodiment, this invention is directed to novel selective androgen receptor degrader (SARD) compounds, which inhibit the growth of prostate cancer (PCa) cells and tumors that are dependent on AR full length (AR-FL) including pathogenic and resistance mutations and wildtype, and AR splice variants (AR-SV) for proliferation.

According to this invention, a "selective androgen receptor degrader" (SARD) compound is an androgen receptor antagonist that is capable of inhibiting the growth of PCa cells and tumors that are dependent on AR-full length (AR-FL) and/or AR splice variants (AR-SV) for proliferation. In another embodiment, the SARD compound does not bind to ligand binding domain (LBD). In another embodiment, the SARD compound binds to the N-terminal domain (NTD) of the AR. In another embodiment, the SARD compound binds to an alternate binding and degradation domain (BDD) of the AR. In another embodiment, the SARD compound binds both to the AR ligand binding domain (LBD) and to an alternate binding and degradation domain (BDD). In another embodiment, the SARD compound binds both to the N-terminal domain (NTD) and to the ligand binding domain (LBD) of the AR. In another embodiment, the SARD compound is capable of inhibiting growth driven by the N-terminal domain (NTD)-dependent constitutively active AR-SV. In another embodiment, the SARD compound inhibits the AR through binding to a domain that is distinct from the AR LBD. In another embodiment, the SARD compound is a strong (i.e., highly potent and highly efficacious) selective androgen receptor antagonist, which antagonizes the AR stronger than other known AR antagonists (e.g., enzalutamide, bicalutamide and abiraterone). In another embodiment, the SARD compound is a selective androgen receptor antagonist, which targets AR-SVs, which cannot be inhibited by conventional antagonists. In another embodiment, the SARD compound exhibits AR-splice variant (AR-SV) degradation activity. In another embodiment, the SARD compound further exhibits AR-full length (AR-FL) degradation activity. In another embodiment, the SARD compound exhibits AR-splice variant (AR-SV) inhibitory activity (i.e., is an AR-SV antagonist). In another embodiment, the SARD compound further exhibits AR-full length (AR-FL) inhibitory activity (i.e., is an AR-FL antagonist). In another embodiment, the SARD compound possesses dual AR-SV degradation and AR-SV inhibitory functions. In another embodiment, the SARD compound further possesses dual AR-FL degradation and AR-FL inhibitory functions. In another embodiment, the SARD compound is a selective androgen receptor antagonist, which targets AR-SVs. In another embodiment, the SARD compound further targets AR-FLs. In another embodiment, the SARD compound inhibits the constitutive activation of AR-SVs. In another embodiment, the SARD compound further inhibits the constitutive activation of AR-FLs. In another embodiment, the SARD compound is a selective androgen receptor antagonist, which degrades AR-full length (AR-FL) and AR splice variants (AR-SV). In another embodiment, the SARD compound degrades the AR through binding to a domain that is distinct from the AR LBD. In another embodiment, the SARD compound possesses dual degradation and AR-SV inhibitory functions that are distinct from any available CRPC therapeutics. In another embodiment, the SARD compound inhibits the re-activation of the AR by alternate mechanisms such as: intracrine androgen synthesis, expression of AR splice variants (AR-SV) that lack ligand binding domain (LBD) and AR-LBD mutations with potential to resist antagonists. In another embodiment, the SARD compound inhibits re-activated androgen receptors presence in pathogenic altered cellular environments.

Nonlimiting examples of AR-splice variants (AR-SVs) are: AR-V7 and ARv567es (a.k.a. AR-V12). Nonlimiting examples of AR mutations conferring antiandrogen resistance are: W741L mutation and T877A mutation. AR-V7 is a splice variant of AR that lacks the LBD. It is constitutively active and has been demonstrated to be responsible for aggressive PCa and resistance to endocrine therapy.

In one embodiment, this invention is directed to novel selective androgen receptor degrader (SARD) compounds, which bind to the AR through an alternate binding and degradation domain (BDD). In another embodiment, the SARDs further binds the AR ligand binding domain (LBD).

In one embodiment, this invention is directed to novel selective androgen receptor degrader (SARD) compounds, which exhibit AR-splice variant (AR-SV) inhibitory activity (i.e., is an AR-SV antagonist). In another embodiment, the novel selective androgen receptor degrader (SARD) compounds, further exhibit AR-full length (AR-FL) inhibitory activity (i.e., is an AR-FL antagonist).

In one embodiment, this invention is directed to novel selective androgen receptor degrader (SARD) compounds, which exhibit AR-splice variant (AR-SV) degradation activity. In another embodiment, the novel selective androgen receptor degrader (SARD) compounds, further exhibit AR-full length (AR-FL) degradation activity.

In one embodiment, this invention is directed to novel selective androgen receptor degrader (SARD) compounds, which possess dual AR-SV degradation and AR-SV inhibitory functions. In another embodiment, the SARDs further possess dual AR-FL degradation and AR-FL inhibitory functions. In another embodiment, this invention is directed to novel selective androgen receptor degrader (SARD) compounds, which possess dual AR-SV and AR-FL degradation, and AR-SV and AR-FL inhibitory functions.

In one embodiment, this invention is directed to novel selective androgen receptor degrader (SARD) compounds, for use in treating CRPC that cannot be treated with any other antagonist.

In one embodiment, this invention is directed to selective androgen receptor degrader (SARD) compounds, for use in treating CRPC, by degrading AR-SVs.

In one embodiment, the novel SARD compounds according to this invention maintain their antagonistic activity in AR mutants that normally convert AR antagonists to agonists. In another embodiment, the SARD compounds maintain their antagonistic activity to AR mutants W741 and T877. In another embodiment, the SARD compounds elicit antagonistic activity within an altered cellular environment in which LBD-targeted agents are not effective. In another embodiment, the SARD compounds elicit antagonistic activity within an altered cellular environment in which NTD-dependent AR activity is constitutively active.

Selective Androgen Receptor Degrader (SARD) Compounds

In one embodiment, this invention is directed to a selective androgen receptor degrader (SARD) compound represented by the structure of formula I:

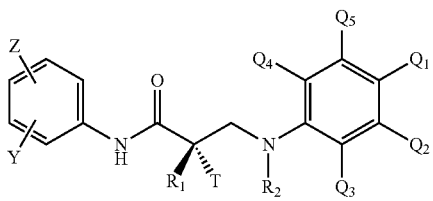

I wherein
T is OH, OR, —NHCOCH₃, or NHCOR;
Z is NO₂, CN, COOH, COR, NHCOR or CONHR;
Y is CF₃, F, I, Br, Cl, CN, C(R)₃ or Sn(R)₃;
R is alkyl, haloalkyl, dihaloalkyl, trihaloalkyl, CH₂F, CHF₂, CF₃, CF₂CF₃, aryl, phenyl, F, Cl, Br, I, alkenyl or OH;
R₁ is CH₃, CH₂F, CHF₂, CF₃, CH₂CH₃, or CF₂CF₃;
R₂ is hydrogen, C₁-C₁₂-alkyl, —SO₂-aryl, —SO₂-phenyl, —CO-aryl, arylalkyl, benzyl, aryl, or C₃-C₇-cycloalkyl;
Q₁, Q₂, Q₃, Q₄, and Q₅ are each independently selected from hydrogen, substituted or unsubstituted linear or branched alkyl, substituted or unsubstituted aryl, substituted or unsubstituted phenyl, F, Cl, Br, I, CF₃, CN, NO₂, substituted or unsubstituted cycloalkyl, substituted or unsubstituted heterocycloalkyl, substituted or unsubstituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO, or OCN;
wherein at least two of Q₁, Q₂, Q₃, Q₄, and Q₅ are not hydrogens; or
Q₁ and Q₂ are joined together to form a substituted or unsubstituted C₅-C₈ carbocyclic or heterocyclic ring, and Q₃, Q₄, and Q₅ are as defined above; or
Q₂ and Q₃ are joined together to form a substituted or unsubstituted C₅-C₈ carbocyclic or heterocyclic ring, and Q₁, Q₄, and Q₅ are as defined above; and
wherein said formed carbocyclic or heterocyclic ring is not dihydropyridin-2(1H)-one, pyridin-2(1H)-one or 1H-pyrrole.

In one embodiment, this invention is directed to a selective androgen receptor degrader (SARD) compound represented by the structure of formula II:

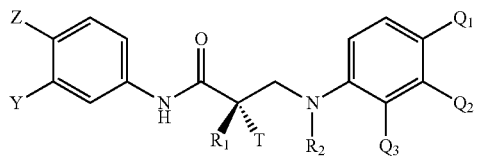

II wherein
T is OH, OR, —NHCOCH₃, or NHCOR;
Z is NO₂, CN, COOH, COR, NHCOR or CONHR;
Y is CF₃, F, I, Br, Cl, CN, C(R)₃ or Sn(R)₃;
R is alkyl, haloalkyl, dihaloalkyl, trihaloalkyl, CH₂F, CHF₂, CF₃, CF₂CF₃, aryl, phenyl, F, Cl, Br, I, alkenyl or OH;
R₁ is CH₃, CH₂F, CHF₂, CF₃, CH₂CH₃, or CF₂CF₃;
R₂ is hydrogen, C₁-C₁₂-alkyl, —SO₂-aryl, —SO₂-phenyl, —CO-aryl, arylalkyl, benzyl, aryl, or C₃-C₇-cycloalkyl;
Q₁ is hydrogen, substituted or unsubstituted linear or branched alkyl, substituted or unsubstituted aryl, substituted or unsubstituted phenyl, F, Cl, Br, I, CF₃, CN, NO₂, substituted or unsubstituted cycloalkyl, substituted or unsubstituted heterocycloalkyl, substituted or unsubstituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO, or OCN;
Q₂ is hydrogen, substituted or unsubstituted linear or branched alkyl, substituted or unsubstituted aryl, substituted or unsubstituted phenyl, F, Cl, Br, I, CF₃, CN, NO₂, substituted or unsubstituted cycloalkyl, substituted or unsubstituted heterocycloalkyl, substituted or unsubstituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO, or OCN;
Q₃ is hydrogen, substituted or unsubstituted linear or branched alkyl, substituted or unsubstituted aryl, substituted or unsubstituted phenyl, F, Cl, Br, I, CF₃, CN, NO₂, substituted or unsubstituted cycloalkyl, substituted or unsubstituted heterocycloalkyl, substituted or unsubstituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO, or OCN;
wherein at least two of Q₁, Q₂ and Q₃ are not hydrogens; or
Q₁ and Q₂ are joined together to form a substituted or unsubstituted C₅-C₈ carbocyclic or heterocyclic ring and Q₃ is as defined above; or
Q₂ and Q₃ are joined together to form a substituted or unsubstituted C₅-C₈ carbocyclic or heterocyclic ring and Q₁ is as defined above; and
wherein said formed carbocyclic or heterocyclic ring is not dihydropyridin-2(1H)-one, pyridin-2(1H)-one or 1H-pyrrole.

In one embodiment, this invention is directed to a selective androgen receptor degrader (SARD) compound represented by the structure of formula III:

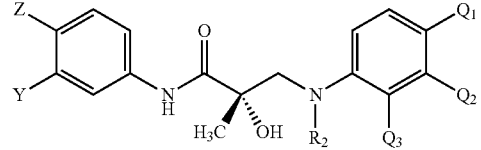

III wherein
Z is NO₂ or CN;
Y is CF₃, F, I, Br, Cl, or CN;
R₂ is hydrogen, C₁-C₁₂-alkyl, —SO₂-aryl, —SO₂-phenyl, —CO-aryl, arylalkyl, benzyl, aryl, or C₃-C₇-cycloalkyl
Q₁ is substituted or unsubstituted aryl, substituted or unsubstituted phenyl, substituted or unsubstituted arylalkyl, CN, or NO₂;
Q₂ is hydrogen, substituted or unsubstituted aryl, substituted or unsubstituted phenyl, F, Cl, Br, I, CF₃, CN, NO₂, substituted or unsubstituted cycloalkyl, substituted or unsubstituted heterocycloalkyl, or substituted or unsubstituted arylalkyl;

$Q_3$ is hydrogen, substituted or unsubstituted aryl, substituted or unsubstituted phenyl, F, Cl, Br, I, $CF_3$, CN, $NO_2$, substituted or unsubstituted cycloalkyl, substituted or unsubstituted heterocycloalkyl, or substituted or unsubstituted arylalkyl;

wherein at least one of $Q_2$ and $Q_3$ is a substituted or unsubstituted aryl, substituted or unsubstituted phenyl or substituted or unsubstituted arylalkyl; or $Q_2$ and $Q_3$ are joined together to form a substituted or unsubstituted $C_5$-$C_8$ carbocyclic or heterocyclic ring and $Q_1$ is as defined above.

In another embodiment, this invention is directed to a selective androgen receptor degrader (SARD) compound represented by the structure of formula III:

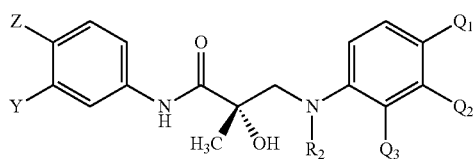

wherein

Z is $NO_2$ or CN;

Y is $CF_3$, F, I, Br, Cl, or CN;

$R_2$ is hydrogen, $C_1$-$C_{12}$-alkyl, —$SO_2$-aryl, —$SO_2$-phenyl, —CO-aryl, substituted or unsubstituted arylalkyl, substituted or unsubstituted benzyl, substituted or unsubstituted aryl, or substituted or unsubstituted $C_3$-$C_7$-cycloalkyl;

$Q_1$, $Q_2$ and $Q_3$ are each independently selected from hydrogen, substituted or unsubstituted aryl, substituted or unsubstituted phenyl, substituted or unsubstituted arylalkyl, F, Cl, Br, I, $CF_3$, CN, $NO_2$, substituted or unsubstituted cycloalkyl, or substituted or unsubstituted heterocycloalkyl;

wherein least one of $Q_1$, $Q_2$ and $Q_3$ is a substituted or unsubstituted aryl, substituted or unsubstituted arylalkyl, or substituted or unsubstituted phenyl;

or $Q_1$ and $Q_2$ are joined together to form a substituted or unsubstituted $C_5$-$C_8$ carbocyclic or heterocyclic ring and $Q_3$ is as defined above;

or $Q_2$ and $Q_3$ are joined together to form a substituted or unsubstituted $C_5$-$C_8$ carbocyclic or heterocyclic ring and $Q_1$ is as defined above; and wherein said formed carbocyclic or heterocyclic ring is not dihydropyridin-2(1H)-one, pyridin-2(1H)-one or 1H-pyrrole.

In one embodiment, this invention is directed to a selective androgen receptor degrader (SARD) compound represented by the structure of formula IV:

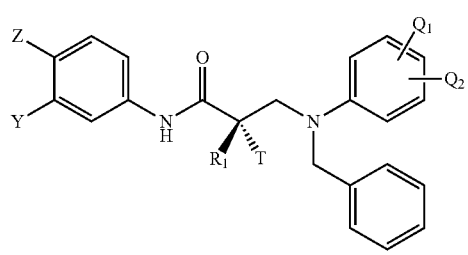

wherein

T is OH, OR, —$NHCOCH_3$, or NHCOR;

Z is $NO_2$, CN, COOH, COR, NHCOR or CONHR;

Y is $CF_3$, F, I, Br, Cl, CN, $C(R)_3$ or $Sn(R)_3$;

R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;

$R_1$ is $CH_3$, $CH_2F$, $CHF_2$, $CF_3$, $CH_2CH_3$, or $CF_2CF_3$;

$Q_1$ is hydrogen, substituted or unsubstituted linear or branched alkyl, substituted or unsubstituted aryl, substituted or unsubstituted phenyl, F, Cl, Br, I, $CF_3$, CN, $NO_2$, substituted or unsubstituted cycloalkyl, substituted or unsubstituted heterocycloalkyl, substituted or unsubstituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO, or OCN;

$Q_2$ is hydrogen, substituted or unsubstituted linear or branched alkyl, substituted or unsubstituted aryl, substituted or unsubstituted phenyl, F, Cl, Br, I, $CF_3$, CN, $NO_2$, substituted or unsubstituted cycloalkyl, substituted or unsubstituted heterocycloalkyl, substituted or unsubstituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO, or OCN;

or $Q_1$ and $Q_2$ are joined together to form a substituted or unsubstituted $C_5$-$C_8$ carbocyclic or heterocyclic ring.

In one embodiment, this invention is directed to a selective androgen receptor degrader (SARD) compound represented by the structure of formula V:

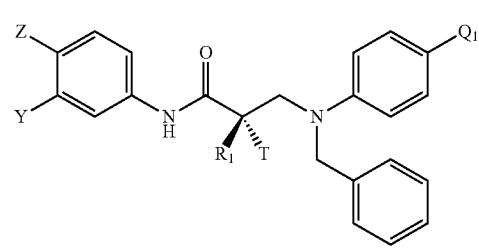

wherein

T is OH, OR, —$NHCOCH_3$, or NHCOR;

Z is $NO_2$, CN, COOH, COR, NHCOR or CONHR;

Y is $CF_3$, F, I, Br, Cl, CN, $C(R)_3$ or $Sn(R)_3$;

R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;

$R_1$ is $CH_3$, $CH_2F$, $CHF_2$, $CF_3$, $CH_2CH_3$, or $CF_2CF_3$; and $Q_1$ is hydrogen, substituted or unsubstituted linear or branched alkyl, substituted or unsubstituted aryl, substituted or unsubstituted phenyl, F, Cl, Br, I, $CF_3$, CN, $NO_2$, substituted or unsubstituted cycloalkyl, substituted or unsubstituted heterocycloalkyl, substituted or unsubstituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO, or OCN.

In one embodiment, this invention is directed to a selective androgen receptor degrader (SARD) compound represented by the structure of formula VI:

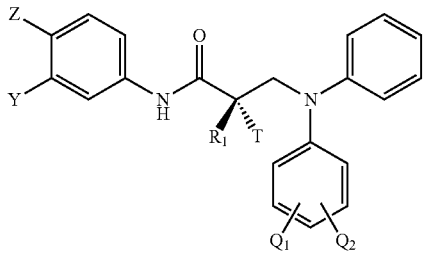

wherein
T is OH, OR, —NHCOCH$_3$, or NHCOR;
Z is NO$_2$, CN, COOH, COR, NHCOR or CONHR;
Y is CF$_3$, F, I, Br, Cl, CN, C(R)$_3$ or Sn(R)$_3$;
R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH;
R$_1$ is CH$_3$, CH$_2$F, CHF$_2$, CF$_3$, CH$_2$CH$_3$, or CF$_2$CF$_3$;
Q$_1$ is hydrogen, substituted or unsubstituted linear or branched alkyl, substituted or unsubstituted aryl, substituted or unsubstituted phenyl, F, Cl, Br, I, CF$_3$, CN, NO$_2$, substituted or unsubstituted cycloalkyl, substituted or unsubstituted heterocycloalkyl, substituted or unsubstituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO, or OCN;
Q$_2$ is hydrogen, substituted or unsubstituted linear or branched alkyl, substituted or unsubstituted aryl, substituted or unsubstituted phenyl, F, Cl, Br, I, CF$_3$, CN, NO$_2$, substituted or unsubstituted cycloalkyl, substituted or unsubstituted heterocycloalkyl, substituted or unsubstituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO, or OCN;
or
Q$_1$ and Q$_2$ are joined together to form a substituted or unsubstituted C$_5$-C$_8$ carbocyclic or heterocyclic ring.

In one embodiment, this invention is directed to a selective androgen receptor degrader (SARD) compound represented by the structure of formula VII:

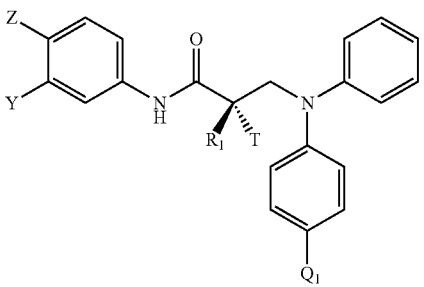

wherein
T is OH, OR, —NHCOCH$_3$, or NHCOR;
Z is NO$_2$, CN, COOH, COR, NHCOR or CONHR;
Y is CF$_3$, F, I, Br, Cl, CN, C(R)$_3$ or Sn(R)$_3$;
R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH;
R$_1$ is CH$_3$, CH$_2$F, CHF$_2$, CF$_3$, CH$_2$CH$_3$, or CF$_2$CF$_3$; and
Q$_1$ is hydrogen, substituted or unsubstituted linear or branched alkyl, substituted or unsubstituted aryl, substituted or unsubstituted phenyl, F, Cl, Br, I, CF$_3$, CN, NO$_2$, substituted or unsubstituted cycloalkyl, substituted or unsubstituted heterocycloalkyl, substituted or unsubstituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO, or OCN.

In one embodiment, Q$_1$ of compound of formulas I-VII is CN. In another embodiment, Q$_1$ is F. In another embodiment, Q$_1$ is Cl. In another embodiment, Q$_1$ is Br. In another embodiment, Q$_1$ is I. In another embodiment, Q$_1$ is NO$_2$. In another embodiment, Q$_1$ is H. In another embodiment, Q$_1$ is phenyl. In another embodiment, Q$_1$ is aryl. In another embodiment, Q$_1$ is arylalkyl. In another embodiment, the arylalkyl is benzyl. In another embodiment, Q$_1$ is 4-fluorophenyl.

In one embodiment, Q$_1$ of compound of formula III is CN. In another embodiment, Q$_1$ is phenyl. In another embodiment, Q$_1$ is aryl. In another embodiment, Q$_1$ is arylalkyl. In another embodiment, the arylalkyl is benzyl. In another embodiment, Q$_1$ is 4-fluorophenyl.

In one embodiment, Q$_1$ of compound of formulas VI or VII is F. In another embodiment, Q$_1$ is Cl. In another embodiment, Q$_1$ is Br. In another embodiment, Q$_1$ is I. In another embodiment, Q$_1$ is NO$_2$. In another embodiment, Q$_1$ is CN.

In one embodiment, Q$_2$ of compound of formulas I-IV and VI is CN. In another embodiment, Q$_2$ is H. In another embodiment, Q$_2$ is phenyl. In another embodiment, Q$_2$ is aryl. In another embodiment, Q$_2$ is arylalkyl. In another embodiment, the arylalkyl is benzyl. In another embodiment, Q$_2$ is 4-fluorophenyl.

In one embodiment, Q$_3$ of compound of formula I-III is CN. In another embodiment, Q$_3$ is H. In another embodiment, Q$_3$ is phenyl. In another embodiment, Q$_3$ is aryl. In another embodiment, Q$_3$ is arylalkyl. In another embodiment, the arylalkyl is benzyl. In another embodiment, Q$_3$ is 4-fluorophenyl.

In one embodiment, Q$_1$ and Q$_2$ of compound of formulas I-IV and VI are joined together to form a substituted or unsubstituted C$_5$-C$_8$ carbocyclic or heterocyclic ring. In another embodiment, the C$_5$-C$_8$ carbocyclic ring is benzene. In another embodiment, the C$_5$-C$_8$ carbocyclic ring is substituted benzene, wherein the substitution is one or more groups selected from halogen, haloalkyl, hydroxy, alkoxy carbonyl, amido, alkylamido, dialkylamido, nitro, amino, alkylamino, dialkylamino, carboxy, thio or thioalkyl. In another embodiment, Q$_1$ and Q$_2$ are —(CH)$_4$—. In another embodiment, the C$_5$-C$_8$ heterocyclic ring is piperidine, pyridine, furan, thiophene, pyrrole, pyrrolidine, pyrazine, piperazine or pyrimidine.

In one embodiment, Q$_2$ and Q$_3$ of compound of formulas I-III are joined together to form a substituted or unsubstituted C$_5$-C$_8$ carbocyclic or heterocyclic ring. In another embodiment, the C$_5$-C$_8$ carbocyclic ring is benzene. In another embodiment, the C$_5$-C$_8$ carbocyclic ring is substituted benzene, wherein the substitution is one or more groups selected from halogen, haloalkyl, hydroxy, alkoxy carbonyl, amido, alkylamido, dialkylamido, nitro, amino, alkylamino, dialkylamino, carboxy, thio or thioalkyl. In another embodiment, $Q_2$ and $Q_3$ are —$(CH)_4$—. In another embodiment, the $C_5$-$C_8$ heterocyclic ring is piperidine, pyridine, furan, thiophene, pyrrole, pyrrolidine, pyrazine, piperazine or pyrimidine.

In one embodiment, $Q_1$ of compound of formulas I-III is CN, $Q_2$ is phenyl and $Q_3$ is hydrogen. In another embodiment, $Q_1$ is CN, $Q_2$ is hydrogen and $Q_3$ is phenyl. In another embodiment, $Q_1$ is CN, and $Q_2$ and $Q_3$ are joined to form benzene ring (i.e. are —$(CH)_4$—).

In one embodiment, $R_2$ of compound of formulas I-III is alkyl. In another embodiment, $R_2$ is methyl. In another embodiment, $R_2$ is ethyl. In another embodiment, $R_2$ is propyl. In another embodiment, $R_2$ is isopropyl. In another embodiment, $R_2$ is pentyl. In another embodiment, $R_2$ is hexyl. In another embodiment, $R_2$ is $C_3$-$C_7$ cycloalkyl. In another embodiment, $R_2$ is cyclobutyl. In another embodiment, $R_2$ is benzyl. In another embodiment, $R_2$ is methylcyclohexyl. In another embodiment, $R_2$ is CO-phenyl. In another embodiment, $R_2$ is $SO_2$-phenyl. In another embodiment, $R_2$ is $SO_2$-phenyl-$OCH_3$. In another embodiment, $R_2$ is $SO_2$-phenyl-F.

In one embodiment, Z of compound of formulas I-VII is CN. In another embodiment, Z is $NO_2$. In another embodiment, Z is COOH. In another embodiment, Z is COR. In another embodiment, Z is NHCOR. In another embodiment, Z is CONHR.

In one embodiment, Y of compound of formulas I-VII is $CF_3$. In another embodiment, Y is F. In another embodiment, Y is I. In another embodiment, Y is Br. In another embodiment, Y is Cl. In another embodiment, Y is CN. In another embodiment, Y is $C(R)_3$. In another embodiment, Y is $Sn(R)_3$.

In one embodiment, Z of compound of formulas I-VII is CN and Y is $CF_3$. In another embodiment, Z is $NO_2$ and Y is $CF_3$. In another embodiment, Z is $NO_2$ and Y is halogen. In another embodiment, Z is CN and Y is halogen.

In one embodiment, $R_1$ of compound of formulas I-II and IV-VII is $CH_3$. In another embodiment, $R_1$ is $CF_3$.

In one embodiment, T of compound of formulas I-II and IV-VII is OH. In another embodiment, T is $OCH_3$.

In one embodiment, R of compound of formulas I-II and IV-VII is alkyl. In another embodiment, R is haloalkyl. In another embodiment, R is dihaloalkyl. In another embodiment, R is trihaloalkyl. In another embodiment, R is $CH_2F$. In another embodiment, R is $CHF_2$. In another embodiment, R is $CF_3$. In another embodiment, R is $CF_2CF_3$. In another embodiment, R is aryl. In another embodiment, R is phenyl. In another embodiment, R is F. In another embodiment, R is Cl. In another embodiment, R is Br. In another embodiment, R is I. In another embodiment, R is alkenyl. In another embodiment, R is hydroxyl (OH).

In one embodiment, this invention is directed to a selective androgen receptor degrader (SARD) compound selected from any one of the following structures:

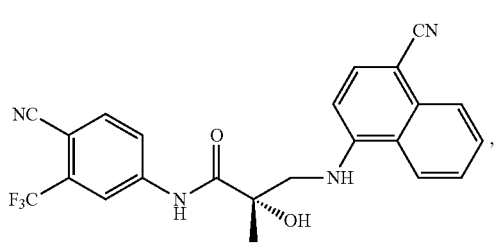

13

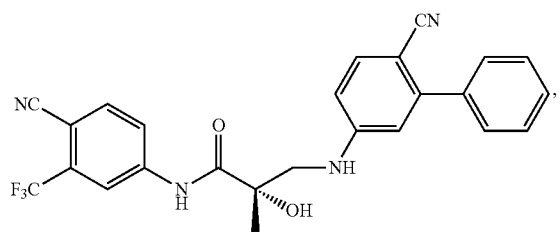

14

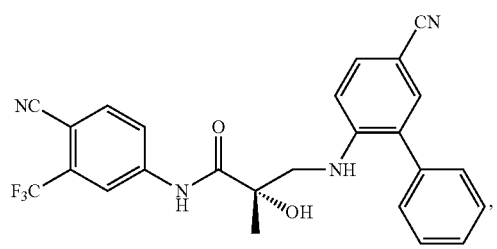

15

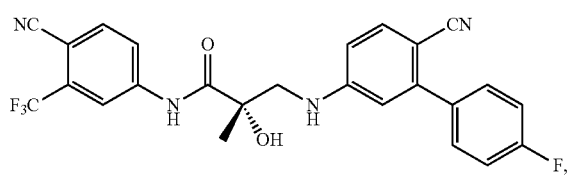

16

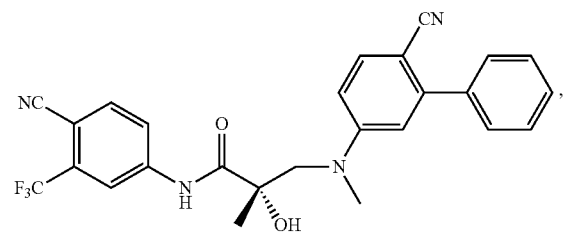

17

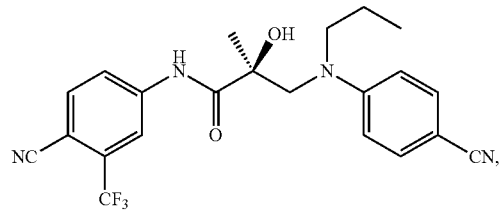

17a

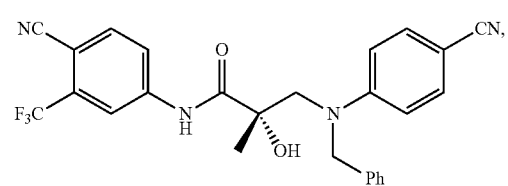

18

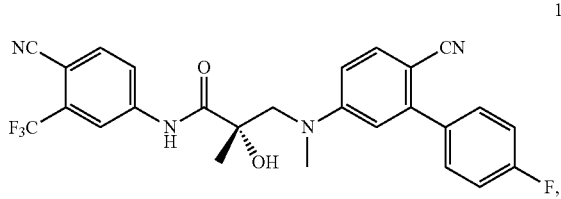

19

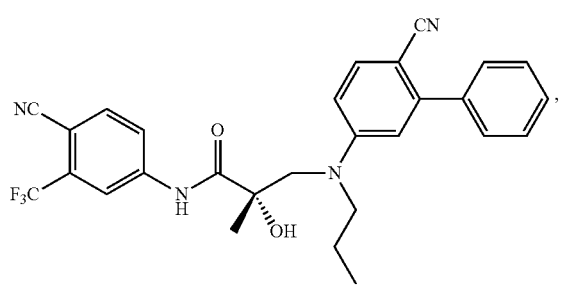

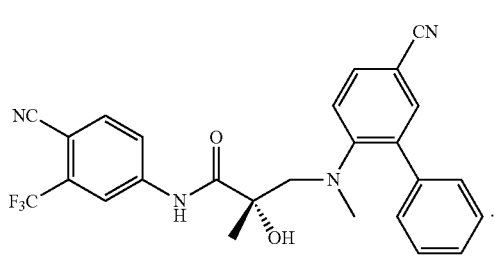

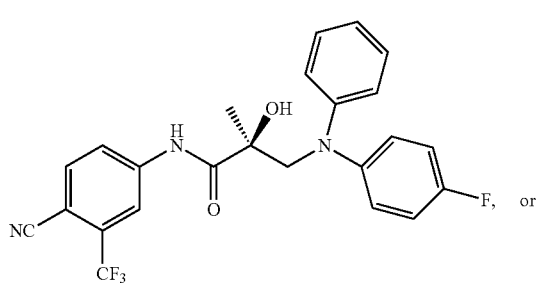

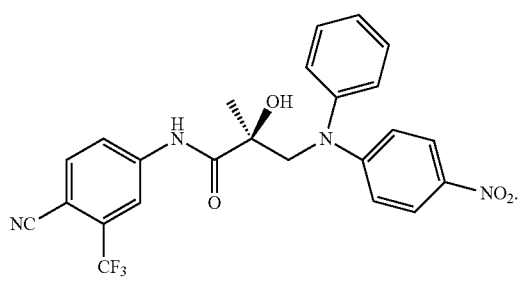

The term "carbocyclic ring" refers to either saturated, unsaturated or aromatic ring composed exclusively of carbon atoms.

The term "heterocycle" group refers, in one embodiment, to a ring structure comprising in addition to carbon atoms, sulfur, oxygen, nitrogen or any combination thereof, as part of the ring. In another embodiment, the heterocycle is a 3-12 membered ring. In another embodiment, the heterocycle is a 6 membered ring. In another embodiment, the heterocycle is a 5-7 membered ring. In another embodiment, the heterocycle is a 4-8 membered ring. In another embodiment, the heterocycle group may be unsubstituted or substituted by a halogen, haloalkyl, hydroxyl, alkoxy, carbonyl, amido, alkylamido, dialkylamido, cyano, nitro, $CO_2H$, amino, alkylamino, dialkylamino, carboxyl, thio and/or thioalkyl. In another embodiment, the heterocycle ring may be fused to another saturated or unsaturated cycloalkyl or heterocyclic 3-8 membered ring. In another embodiment, the heterocyclic ring is a saturated ring. In another embodiment, the heterocyclic ring is an unsaturated ring. In another embodiment, the heterocycle is piperidine. In another embodiment, the heterocycle is pyridine. In another embodiment, the heterocycle is piperidine, pyridine, furan, thiophene, pyrrole, pyrrolidine, pyrazine, piperazine or pyrimidine.

The term "cycloalkyl" refers to a non-aromatic, monocyclic or polycyclic ring comprising carbon and hydrogen atoms. A cycloalkyl group can have one or more carbon-carbon double bonds in the ring so long as the ring is not rendered aromatic by their presence. Examples of cycloalkyl groups include, but are not limited to, ($C_3$-$C_7$) cycloalkyl groups, such as cyclopropyl, cyclobutyl, cyclopentyl, cyclohexyl, and cycloheptyl, and saturated cyclic and bicyclic terpenes and ($C_3$-$C_7$) cycloalkenyl groups, such as cyclopropenyl, cyclobutenyl, cyclopentenyl, cyclohexenyl, and cycloheptenyl, and unsaturated cyclic and bicyclic terpenes. A cycloalkyl group can be unsubstituted or substituted by one or two substituents. Preferably, the cycloalkyl group is a monocyclic ring or bicyclic ring.

Non limiting examples for "$C_5$-$C_8$ carbocyclic or heterocyclic rings" are carbocyclic rings such as cyclopentane, cyclopentene, cyclohexane, benzene, and cyclohexene rings, and heterocyclic rings such as pyran, dihydropyran, tetrahydropyran, dihydropyrrole, tetrahydropyrrole, pyrazine, dihydropyrazine, tetrahydropyrazine, pyrimidine, dihydropyrimidine, tetrahydropyrimidone, pyrazole, dihydropyrazole, tetrahydropyrazole, piperidine, piperazine, pyridine, dihydropyridine, tetrahydropyridine, morpholine, thiomorpholine, furan, dihydrofuran, tetrahydrofuran, thiophene, dihydrothiophene, tetrahydrothiophene, thiazole, imidazole, isoxazole, and the like.

The term "alkyl" refers, in one embodiment, to a saturated aliphatic hydrocarbon, including straight-chain, branched-chain and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-4 carbons. In another embodiment, the cyclic alkyl group has 3-8 carbons. In another embodiment, the cyclic alkyl group has 3-12 carbons. In another embodiment, the branched alkyl is an alkyl substituted by alkyl side chains of 1 to 5 carbons. In another embodiment, the branched alkyl is an alkyl substituted by haloalkyl side chains of 1 to 5 carbons. The alkyl group may be unsubstituted or substituted by a halogen, haloalkyl, hydroxyl, alkoxy carbonyl, amido, alkylamido, dialkylamido, nitro, amino, alkylamino, dialkylamino, carboxyl, thio and/or thioalkyl.

An "arylalkyl" group refers to an alkyl bound to an aryl, wherein alkyl and aryl are as defined above. An example of an arylalkyl group is a benzyl group.

An "alkenyl" group refers, in another embodiment, to an unsaturated hydrocarbon, including straight chain, branched chain and cyclic groups having one or more double bonds. The alkenyl group may have one double bond, two double bonds, three double bonds, etc. In another embodiment, the alkenyl group has 2-12 carbons. In another embodiment, the alkenyl group has 2-6 carbons. In another embodiment, the alkenyl group has 2-4 carbons. Examples of alkenyl groups are ethenyl, propenyl, butenyl, cyclohexenyl, etc. The alkenyl group may be unsubstituted or substituted by a halogen, hydroxy, alkoxy carbonyl, amido, alkylamido, dialkylamido, nitro, amino, alkylamino, dialkylamino, carboxyl, thio and/or thioalkyl.

An "aryl" group refers to an aromatic group having at least one carbocyclic aromatic group or heterocyclic aromatic group, which may be unsubstituted or substituted by one or more groups selected from halogen, haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like. In one embodiment, the aryl group is a 4-8 membered ring. In another embodiment, the aryl group is a 4-12 membered ring(s). In another embodiment, the aryl group is a 6 membered ring. In another embodiment, the aryl group is a 5 membered ring. In another embodiment, the aryl group is 2-4 fused ring system.

A "aldehyde" group refers, in one embodiment, to an alkyl, or alkenyl substituted by a formyl group, wherein the alkyl or alkenyl are as defined hereinabove. In another embodiment, the aldehyde group is an aryl, or phenyl group substituted by a formyl group, wherein the aryl is as defined hereinabove. Examples of aldehydes are: formyl, acetal, propanal, butanal, pentanal, benzaldehyde. In another embodiment, the aldehyde group is a formyl group.

A "haloalkyl" group refers, in another embodiment, to an alkyl group as defined above, which is substituted by one or more halogen atoms, e.g. by F, Cl, Br or I.

A "hydroxyl" group refers, in another embodiment, to an OH group. It is understood by a person skilled in the art that when $R_1$, $R_2$ or $R_3$ in the compounds of the present invention is OR, then R is not OH.

In one embodiment, the term "halogen" or "halo" refers to a halogen, such as F, Cl, Br or I.

In another embodiment, the phrase "phenol" refers to an alcohol (OH) derivative of benzene.

In one embodiment, this invention provides for the use of a compound as herein described and/or, its derivative, isomer, metabolite, pharmaceutically acceptable salt, pharmaceutical product, hydrate, N-oxide, prodrug, polymorph, crystal or combinations thereof.

In one embodiment, the methods of this invention make use of "pharmaceutically acceptable salts" of the compounds, which may be produced, by reaction of a compound of this invention with an acid or base.

Suitable pharmaceutically acceptable salts of amines of the compounds of the methods of this invention may be prepared from an inorganic acid or from an organic acid. In one embodiment, examples of inorganic salts of amines are bisulfates, borates, bromides, chlorides, hemisulfates, hydrobromates, hydrochlorates, 2-hydroxyethylsulfonates (hydroxyethanesulfonates), iodates, iodides, isothionates, nitrates, persulfates, phosphate, sulfates, sulfamates, sulfanilates, sulfonic acids (alkylsulfonates, arylsulfonates, halogen substituted alkylsulfonates, halogen substituted arylsulfonates), sulfonates and thiocyanates.

In one embodiment, examples of organic salts of amines may be selected from aliphatic, cycloaliphatic, aromatic, araliphatic, heterocyclic, carboxylic and sulfonic classes of organic acids, examples of which are acetates, arginines, aspartates, ascorbates, adipates, anthranilates, algenates, alkane carboxylates, substituted alkane carboxylates, alginates, benzenesulfonates, benzoates, bisulfates, butyrates, bicarbonates, bitartrates, carboxylates, citrates, camphorates, camphorsulfonates, cyclohexylsulfamates, cyclopentanepropionates, calcium edetates, camsylates, carbonates, clavulanates, cinnamates, dicarboxylates, digluconates, dodecylsulfonates, dihydrochlorides, decanoates, enanthuates, ethanesulfonates, edetates, edisylates, estolates, esylates, fumarates, formates, fluorides, galacturonates, gluconates, glutamates, glycolates, glucorates, glucoheptanoates, glycerophosphates, gluceptates, glycollylarsanilates, glutarates, glutamates, heptanoates, hexanoates, hydroxymaleates, hydroxycarboxlic acids, hexylresorcinates, hydroxybenzoates, hydroxynaphthoates, hydrofluorates, lactates, lactobionates, laurates, malates, maleates, methylenebis(beta-oxynaphthoate), malonates, mandelates, mesylates, methane sulfonates, methylbromides, methylnitrates, methylsulfonates, monopotassium maleates, mucates, monocarboxylates, nitrates, naphthalenesulfonates, 2-naphthalenesulfonates, nicotinates, napsylates, N-methylglucamines, oxalates, octanoates, oleates, pamoates, phenylacetates, picrates, phenylbenzoates, pivalates, propionates, phthalates, pectinates, phenylpropionates, palmitates, pantothenates, polygalacturates, pyruvates, quinates, salicylates, succinates, stearates, sulfanilates, subacetates, tartarates, theophyllineacetates, p-toluenesulfonates (tosylates), trifluoroacetates, terephthalates, tannates, teoclates, trihaloacetates, triethiodide, tricarboxylates, undecanoates and valerates.

In one embodiment, examples of inorganic salts of carboxylic acids or phenols may be selected from ammonium, alkali metals to include lithium, sodium, potassium, cesium; alkaline earth metals to include calcium, magnesium, aluminium; zinc, barium, cholines, quaternary ammoniums.

In another embodiment, examples of organic salts of carboxylic acids or phenols may be selected from arginine, organic amines to include aliphatic organic amines, alicyclic organic amines, aromatic organic amines, benzathines, t-butylamines, benethamines (N-benzylphenethylamine), dicyclohexylamines, dimethylamines, diethanolamines, ethanolamines, ethylenediamines, hydrabamines, imidazoles, lysines, methylamines, meglamines, N-methyl-D-glucamines, N,N'-dibenzylethylenediamines, nicotinamides, organic amines, ornithines, pyridines, picolies, piperazines, procaine, tris(hydroxymethyl)methylamines, triethylamines, triethanolamines, trimethylamines, tromethamines and ureas.

In one embodiment, the salts may be formed by conventional means, such as by reacting the free base or free acid form of the product with one or more equivalents of the appropriate acid or base in a solvent or medium in which the salt is insoluble or in a solvent such as water, which is removed in vacuo or by freeze drying or by exchanging the ions of a existing salt for another ion or suitable ion-exchange resin.

In one embodiment, the methods of this invention make use of a pharmaceutically acceptable salt of the compounds of this invention. In one embodiment, the methods of this invention make use of a pharmaceutically acceptable salt of compounds of formulas I-VII. In one embodiment, the methods of this invention make use of a salt of an amine of the compounds of formulas I-VII of this invention. In one embodiment, the methods of this invention make use of a salt of a phenol of the compounds of formulas I-VII of this invention.

In one embodiment, the methods of this invention make use of a free base, free acid, non charged or non-complexed compounds of formulas I-VII and/or its isomer, pharmaceutical product, hydrate, polymorph, or combinations thereof.

In one embodiment, the methods of this invention make use of an isomer of a compound of formulas I-VII. In one embodiment, the methods of this invention make use of a pharmaceutical product of a compound of formulas I-VII. In one embodiment, the methods of this invention make use of a hydrate of a compound of formulas I-VII. In one embodiment, the methods of this invention make use of a polymorph of a compound of formulas I-VII. In one embodiment, the methods of this invention make use of a metabolite of a compound of formulas I-VII. In another embodiment, the methods of this invention make use of a composition comprising a compound of formulas I-VII, as described herein, or, in another embodiment, a combination of isomer, metabolite, pharmaceutical product, hydrate, polymorph of a compound of formulas I-VII.

In one embodiment, the term "isomer" includes, but is not limited to, optical isomers and analogs, structural isomers and analogs, conformational isomers and analogs, and the like.

In one embodiment, the term "isomer" is meant to encompass optical isomers of the SARD compound. It will be appreciated by those skilled in the art that the SARDs of the present invention contain at least one chiral center. Accordingly, the SARDs used in the methods of the present invention may exist in, and be isolated in, optically-active or racemic forms. Some compounds may also exhibit polymorphism. It is to be understood that the present invention encompasses any racemic, optically-active, polymorphic, or stereroisomeric form, or mixtures thereof, which form possesses properties useful in the treatment of androgen-related conditions described herein. In one embodiment, the SARDs are the pure (R)-isomers. In another embodiment, the SARDs are the pure (S)-isomers. In another embodiment, the SARDs are a mixture of the (R) and the (S) isomers. In another embodiment, the SARDs are a racemic mixture comprising an equal amount of the (R) and the (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

In another embodiment, this invention further includes hydrates of the compounds. The invention also includes use of N-oxides of the amino substituents of the compounds described herein.

In one embodiment, the term "hydrate" refers to hemihydrate, monohydrate, dihydrate, trihydrate or others, as known in the art.

This invention provides, in other embodiments, use of metabolites of the compounds as herein described. In one embodiment, "metabolite" means any substance produced from another substance by metabolism or a metabolic process.

Compounds as herein described may be prepared by any means known in the art, including inter alia, those described in U.S. patent application Ser. No. 11/505,363, U.S. patent application Ser. No. 11/505,499 and U.S. patent application Ser. No. 11/394,181; and U.S. patent application Ser. No. 10/462,837 fully incorporated by reference herein in their entirety.

In another example, Compounds 13-21, 17a, 49 or 50 are prepared according to Example 1A and Example 1B.

Biological Activity of Selective Androgen Receptor Degraders

In one embodiment, this invention provides a method of treating, suppressing, reducing the incidence, reducing the severity, or inhibiting the progression of prostate cancer (PCa) and its symptoms, or increasing the survival of a male subject suffering from prostate cancer comprising administering to said subject a therapeutically effective amount of a compound or its isomer, pharmaceutically acceptable salt, pharmaceutical product, polymorph, hydrate or any combination thereof, represented by a compound of formula I:

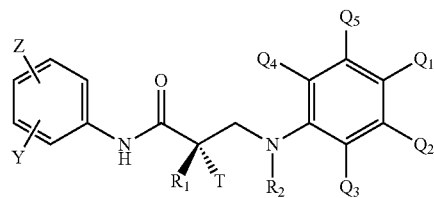

wherein
T is OH, OR, —NHCOCH$_3$, or NHCOR;
Z is NO$_2$, CN, COOH, COR, NHCOR or CONHR;
Y is CF$_3$, F, I, Br, Cl, CN, C(R)$_3$ or Sn(R)$_3$;
R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH;
R$_1$ is CH$_3$, CH$_2$F, CHF$_2$, CF$_3$, CH$_2$CH$_3$, or CF$_2$CF$_3$;
R$_2$ is hydrogen, C$_1$-C$_{12}$-alkyl, —SO$_2$-aryl, —SO$_2$-phenyl, —CO-aryl, arylalkyl, benzyl, aryl, or C$_3$-C$_7$-cycloalkyl;
Q$_1$, Q$_2$, Q$_3$, Q$_4$, and Q$_5$ are each independently selected from hydrogen, substituted or unsubstituted linear or branched alkyl, substituted or unsubstituted aryl, substituted or unsubstituted phenyl, F, Cl, Br, I, CF$_3$, CN, NO$_2$, substituted or unsubstituted cycloalkyl, substituted or unsubstituted heterocycloalkyl, substituted or unsubstituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO, or OCN;
wherein at least two of Q$_1$, Q$_2$, Q$_3$, Q$_4$, and Q$_5$ are not hydrogens; or
Q$_1$ and Q$_2$ are joined together to form a substituted or unsubstituted C$_5$-C$_8$ carbocyclic or heterocyclic ring, and Q$_3$, Q$_4$, and Q$_5$ are as defined above; or
Q$_2$ and Q$_3$ are joined together to form a substituted or unsubstituted C$_5$-C$_8$ carbocyclic or heterocyclic ring, and Q$_1$, Q$_4$, and Q$_5$ are as defined above; and
wherein said formed carbocyclic or heterocyclic ring is not dihydropyridin-2(1H)-one, pyridin-2(1H)-one or 1H-pyrrole.

In another embodiment, the prostate cancer is advanced prostate cancer, castration resistant prostate cancer (CRPC), metastatic CRPC (mCRPC), non-metastatic CRPC (nm-CRPC), high-risk nmCRPC or any combination thereof. In another embodiment, the prostate cancer depends on AR-FL and/or AR-SV for proliferation. In another embodiment, the subject further receives androgen deprivation therapy (ADT). In another embodiment, the subject has failed androgen deprivation therapy (ADT). In another embodiment, the cancer is resistant to treatment with an androgen receptor antagonist. In another embodiment, the cancer is resistant to treatment with enzalutamide, bicalutamide, abiraterone, ARN-509, AZD-3514, galeterone, ASC-J9, flutamide, hydroxyflutamide, nilutamide, cyproterone acetate, ketoconazole, spironolactone, or any combination thereof. In another embodiment, administering the compound to a subject reduces the levels of AR, AR-full length (AR-FL), AR-FL with antiandrogen resistance-conferring AR-LBD mutations, AR-splice variant (AR-SV), gene-amplified AR, or any combination thereof, in said subject.

In one embodiment, this invention provides a method of treating, suppressing, reducing the incidence, reducing the severity, or inhibiting the progression of prostate cancer (PCa) and its symptoms, or increasing the survival of a male subject suffering from prostate cancer comprising administering to said subject a therapeutically effective amount of a compound or its isomer, pharmaceutically acceptable salt, pharmaceutical product, polymorph, hydrate or any combination thereof, represented by a compound of formula II:

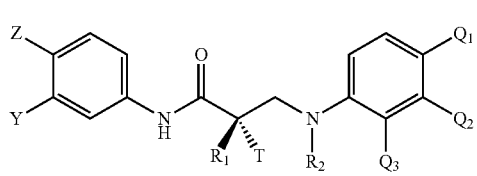

wherein
T is OH, OR, —NHCOCH$_3$, or NHCOR;
Z is NO$_2$, CN, COOH, COR, NHCOR or CONHR;
Y is CF$_3$, F, I, Br, Cl, CN, C(R)$_3$ or Sn(R)$_3$;
R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH;
R$_1$ is CH$_3$, CH$_2$F, CHF$_2$, CF$_3$, CH$_2$CH$_3$, or CF$_2$CF$_3$;
R$_2$ is hydrogen, C$_1$-C$_{12}$-alkyl, —SO$_2$-aryl, —SO$_2$-phenyl, —CO-aryl, arylalkyl, benzyl, aryl, or C$_3$-C$_7$-cycloalkyl;
Q$_1$ is hydrogen, substituted or unsubstituted linear or branched alkyl, substituted or unsubstituted aryl, substituted or unsubstituted phenyl, F, Cl, Br, I, CF$_3$, CN, NO$_2$, substituted or unsubstituted cycloalkyl, substituted or unsubstituted heterocycloalkyl, substituted or unsubstituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO, or OCN;
Q$_2$ is hydrogen, substituted or unsubstituted linear or branched alkyl, substituted or unsubstituted aryl, substituted or unsubstituted phenyl, F, Cl, Br, I, CF$_3$, CN, NO$_2$, substituted or unsubstituted cycloalkyl, substituted or unsubstituted heterocycloalkyl, substituted or unsubstituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO, or OCN;
Q$_3$ is hydrogen, substituted or unsubstituted linear or branched alkyl, substituted or unsubstituted aryl, substituted or unsubstituted phenyl, F, Cl, Br, I, CF$_3$, CN, NO$_2$, substituted or unsubstituted cycloalkyl, substituted or unsubstituted heterocycloalkyl, substituted or unsubstituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO, or OCN;
wherein least two of Q$_1$, Q$_2$ and Q$_3$ are not hydrogens; or Q$_1$ and Q$_2$ are joined together to form a substituted or unsubstituted C$_5$-C$_8$ carbocyclic or heterocyclic ring and Q$_3$ is as defined above; or Q$_2$ and Q$_3$ are joined together to form a substituted or unsubstituted C$_5$-C$_8$ carbocyclic or heterocyclic ring and Q$_1$ is as defined above; and
wherein said formed carbocyclic or heterocyclic ring is not dihydropyridin-2(1H)-one, pyridin-2(1H)-one or 1H-pyrrole.

In another embodiment, the prostate cancer is advanced prostate cancer, castration resistant prostate cancer (CRPC), metastatic CRPC (mCRPC), non-metastatic CRPC (nm-CRPC), high-risk nmCRPC or any combination thereof. In another embodiment, the prostate cancer depends on AR-FL and/or AR-SV for proliferation. In another embodiment, the subject further receives androgen deprivation therapy (ADT). In another embodiment, the subject has failed androgen deprivation therapy (ADT). In another embodiment, the cancer is resistant to treatment with an androgen receptor antagonist. In another embodiment, the cancer is resistant to treatment with enzalutamide, bicalutamide, abiraterone, ARN-509, AZD-3514, galeterone, ASC-J9, flutamide, hydroxyflutamide, nilutamide, cyproterone acetate, ketoconazole, spironolactone, or any combination thereof. In another embodiment, administering the compound to a subject reduces the levels of AR, AR-full length (AR-FL), AR-FL with antiandrogen resistance-conferring AR-LBD mutations, AR-splice variant (AR-SV), gene-amplified AR, or any combination thereof, in said subject.

In one embodiment, this invention provides a method of treating, suppressing, reducing the incidence, reducing the severity, or inhibiting the progression of prostate cancer (PCa) and its symptoms, or increasing the survival of a male subject suffering from prostate cancer comprising administering to said subject a therapeutically effective amount of a compound or its isomer, pharmaceutical product, pharmaceutically acceptable salt, polymorph, hydrate or any combination thereof, represented by a compound of formula III:

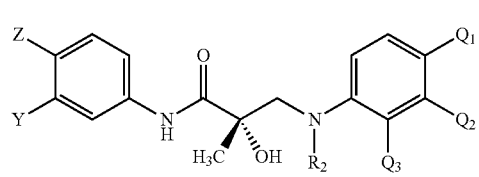

wherein
Z is NO$_2$ or CN;
Y is CF$_3$, F, I, Br, Cl, or CN;
R$_2$ is hydrogen, C$_1$-C$_{12}$-alkyl, —SO$_2$-aryl, —SO$_2$-phenyl, —CO-aryl, arylalkyl, benzyl, aryl, or C$_3$-C$_7$-cycloalkyl
Q$_1$ is substituted or unsubstituted aryl, substituted or unsubstituted phenyl, substituted or unsubstituted arylalkyl, CN, or NO$_2$;
Q$_2$ is hydrogen, substituted or unsubstituted aryl, substituted or unsubstituted phenyl, F, Cl, Br, I, CF$_3$, CN, NO$_2$, substituted or unsubstituted cycloalkyl, substituted or unsubstituted heterocycloalkyl, or substituted or unsubstituted arylalkyl;
Q$_3$ is hydrogen, substituted or unsubstituted aryl, substituted or unsubstituted phenyl, F, Cl, Br, I, CF$_3$, CN, NO$_2$, substituted or unsubstituted cycloalkyl, substituted or unsubstituted heterocycloalkyl, or substituted or unsubstituted arylalkyl;
wherein at least one of Q$_2$ and Q$_3$ is a substituted or unsubstituted aryl, substituted or unsubstituted phenyl, or substituted or unsubstituted arylalkyl; or
Q$_2$ and Q$_3$ are joined together to form a substituted or unsubstituted C$_5$-C$_8$ carbocyclic or heterocyclic ring and Q$_1$ is as defined above.

In another embodiment, the prostate cancer is advanced prostate cancer, castration resistant prostate cancer (CRPC), metastatic CRPC (mCRPC), non-metastatic CRPC (nm-CRPC), high-risk nmCRPC or any combination thereof. In another embodiment, the prostate cancer depends on AR-FL and/or AR-SV for proliferation. In another embodiment, the subject further receives androgen deprivation therapy (ADT). In another embodiment, the subject has failed androgen deprivation therapy (ADT). In another embodiment, the cancer is resistant to treatment with an androgen receptor antagonist. In another embodiment, the cancer is resistant to treatment with enzalutamide, bicalutamide, abiraterone, ARN-509, AZD-3514, galeterone, ASC-J9, flutamide, hydroxyflutamide, nilutamide, cyproterone acetate, ketoconazole, spironolactone, or any combination thereof. In another embodiment, administering the compound to a subject reduces the levels of AR, AR-full length (AR-FL), AR-FL with antiandrogen resistance-conferring AR-LBD mutations, AR-splice variant (AR-SV), gene-amplified AR, or any combination thereof, in said subject.

In another embodiment, this invention provides a method of treating, suppressing, reducing the incidence, reducing the severity, or inhibiting the progression of prostate cancer (PCa) and its symptoms, or increasing the survival of a male subject suffering from prostate cancer comprising administering to said subject a therapeutically effective amount of a compound or its isomer, pharmaceutically acceptable salt, pharmaceutical product, polymorph, hydrate or any combination thereof, represented by a compound of formula III:

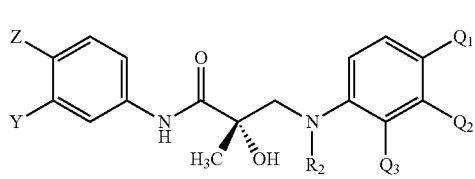

III wherein
Z is $NO_2$ or CN;
Y is $CF_3$, F, I, Br, Cl, or CN;
$R_2$ is hydrogen, $C_1$-$C_{12}$-alkyl, —$SO_2$-aryl, —$SO_2$-phenyl, —CO-aryl, substituted or unsubstituted arylalkyl, substituted or unsubstituted benzyl, substituted or unsubstituted aryl, or substituted or unsubstituted $C_3$-$C_7$-cycloalkyl;
$Q_1$, $Q_2$ and $Q_3$ are each independently selected from hydrogen, substituted or unsubstituted aryl, substituted or unsubstituted phenyl, substituted or unsubstituted arylalkyl, F, Cl, Br, I, $CF_3$, CN, $NO_2$, substituted or unsubstituted cycloalkyl, or substituted or unsubstituted heterocycloalkyl;
wherein at least one of $Q_1$, $Q_2$ and $Q_3$ is a substituted or unsubstituted aryl, substituted or unsubstituted arylalkyl, or substituted or unsubstituted phenyl;
or
$Q_1$ and $Q_2$ are joined together to form a substituted or unsubstituted $C_5$-$C_8$ carbocyclic or heterocyclic ring and $Q_3$ is as defined above;
or
$Q_2$ and $Q_3$ are joined together to form a substituted or unsubstituted $C_5$-$C_8$ carbocyclic or heterocyclic ring and $Q_1$ is as defined above; and
wherein said formed carbocyclic or heterocyclic ring is not dihydropyridin-2(1H)-one, pyridin-2(1H)-one or 1H-pyrrole.

In another embodiment, the prostate cancer is advanced prostate cancer, castration resistant prostate cancer (CRPC), metastatic CRPC (mCRPC), non-metastatic CRPC (nm-CRPC), high-risk nmCRPC or any combination thereof. In another embodiment, the prostate cancer depends on AR-FL and/or AR-SV for proliferation. In another embodiment, the subject further receives androgen deprivation therapy (ADT). In another embodiment, the subject has failed androgen deprivation therapy (ADT). In another embodiment, the cancer is resistant to treatment with an androgen receptor antagonist. In another embodiment, the cancer is resistant to treatment with enzalutamide, bicalutamide, abiraterone, ARN-509, AZD-3514, galeterone, ASC-J9, flutamide, hydroxyflutamide, nilutamide, cyproterone acetate, ketoconazole, spironolactone, or any combination thereof. In another embodiment, administering the compound to a subject reduces the levels of AR, AR-full length (AR-FL), AR-FL with antiandrogen resistance-conferring AR-LBD mutations, AR-splice variant (AR-SV), gene-amplified AR, or any combination thereof, in said subject.

In one embodiment, this invention provides a method of treating, suppressing, reducing the incidence, reducing the severity, or inhibiting the progression of prostate cancer (PCa) and its symptoms, or increasing the survival of a male subject suffering from prostate cancer comprising administering to said subject a therapeutically effective amount of a compound or its isomer, pharmaceutically acceptable salt, pharmaceutical product, polymorph, hydrate or any combination thereof, represented by a compound of formula IV:

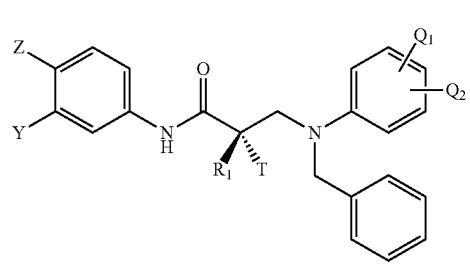

IV wherein
T is OH, OR, —$NHCOCH_3$, or NHCOR;
Z is $NO_2$, CN, COOH, COR, NHCOR or CONHR;
Y is $CF_3$, F, I, Br, Cl, CN, $C(R)_3$ or $Sn(R)_3$;
R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;
$R_1$ is $CH_3$, $CH_2F$, $CHF_2$, $CF_3$, $CH_2CH_3$, or $CF_2CF_3$;
$Q_1$ is hydrogen, substituted or unsubstituted linear or branched alkyl, substituted or unsubstituted aryl, substituted or unsubstituted phenyl, F, Cl, Br, I, $CF_3$, CN, $NO_2$, substituted or unsubstituted cycloalkyl, substituted or unsubstituted heterocycloalkyl, substituted or unsubstituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO, or OCN;
$Q_2$ is hydrogen, substituted or unsubstituted linear or branched alkyl, substituted or unsubstituted aryl, substituted or unsubstituted phenyl, F, Cl, Br, I, $CF_3$, CN, $NO_2$, substituted or unsubstituted cycloalkyl, substituted or unsubstituted heterocycloalkyl, substituted or unsubstituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO, or OCN;

or

Q$_1$ and Q$_2$ are joined together to form a substituted or unsubstituted C$_5$-C$_8$ carbocyclic or heterocyclic ring.

In another embodiment, the prostate cancer is advanced prostate cancer, castration resistant prostate cancer (CRPC), metastatic CRPC (mCRPC), non-metastatic CRPC (nm-CRPC), high-risk nmCRPC or any combination thereof. In another embodiment, the prostate cancer depends on AR-FL and/or AR-SV for proliferation. In another embodiment, the subject further receives androgen deprivation therapy (ADT). In another embodiment, the subject has failed androgen deprivation therapy (ADT). In another embodiment, the cancer is resistant to treatment with an androgen receptor antagonist. In another embodiment, the cancer is resistant to treatment with enzalutamide, bicalutamide, abiraterone, ARN-509, AZD-3514, galeterone, ASC-J9, flutamide, hydroxyflutamide, nilutamide, cyproterone acetate, ketoconazole, spironolactone, or any combination thereof. In another embodiment, administering the compound to a subject reduces the levels of AR, AR-full length (AR-FL), AR-FL with antiandrogen resistance-conferring AR-LBD mutations, AR-splice variant (AR-SV), gene-amplified AR, or any combination thereof, in said subject.

In one embodiment, this invention provides a method of treating, suppressing, reducing the incidence, reducing the severity, or inhibiting the progression of prostate cancer (PCa) and its symptoms, or increasing the survival of a male subject suffering from prostate cancer comprising administering to said subject a therapeutically effective amount of a compound or its isomer, pharmaceutically acceptable salt, pharmaceutical product, polymorph, hydrate or any combination thereof, represented by a compound of formula V:

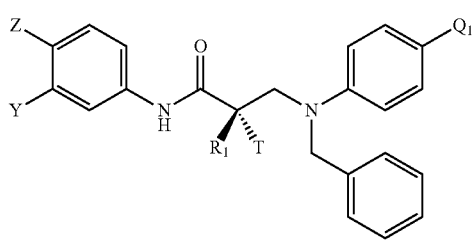

V wherein
T is OH, OR, —NHCOCH$_3$, or NHCOR;
Z is NO$_2$, CN, COOH, COR, NHCOR or CONHR;
Y is CF$_3$, F, I, Br, Cl, CN, C(R)$_3$ or Sn(R)$_3$;
R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH;
R$_1$ is CH$_3$, CH$_2$F, CHF$_2$, CF$_3$, CH$_2$CH$_3$, or CF$_2$CF$_3$; and
Q$_1$ is hydrogen, substituted or unsubstituted linear or branched alkyl, substituted or unsubstituted aryl, substituted or unsubstituted phenyl, F, Cl, Br, I, CF$_3$, CN, NO$_2$, substituted or unsubstituted cycloalkyl, substituted or unsubstituted heterocycloalkyl, substituted or unsubstituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO, or OCN.

In another embodiment, the prostate cancer is advanced prostate cancer, castration resistant prostate cancer (CRPC), metastatic CRPC (mCRPC), non-metastatic CRPC (nm-CRPC), high-risk nmCRPC or any combination thereof. In another embodiment, the prostate cancer depends on AR-FL and/or AR-SV for proliferation. In another embodiment, the subject further receives androgen deprivation therapy (ADT). In another embodiment, the subject has failed androgen deprivation therapy (ADT). In another embodiment, the cancer is resistant to treatment with an androgen receptor antagonist. In another embodiment, the cancer is resistant to treatment with enzalutamide, bicalutamide, abiraterone, ARN-509, AZD-3514, galeterone, ASC-J9, flutamide, hydroxyflutamide, nilutamide, cyproterone acetate, ketoconazole, spironolactone, or any combination thereof. In another embodiment, administering the compound to a subject reduces the levels of AR, AR-full length (AR-FL), AR-FL with antiandrogen resistance-conferring AR-LBD mutations, AR-splice variant (AR-SV), gene-amplified AR, or any combination thereof, in said subject.

In one embodiment, this invention provides a method of treating, suppressing, reducing the incidence, reducing the severity, or inhibiting the progression of prostate cancer (PCa) and its symptoms, or increasing the survival of a male subject suffering from prostate cancer comprising administering to said subject a therapeutically effective amount of a compound or its isomer, pharmaceutically acceptable salt, pharmaceutical product, polymorph, hydrate or any combination thereof, represented by a compound of formula VI:

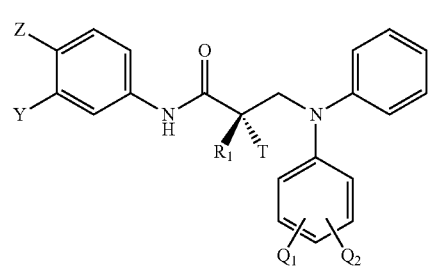

VI wherein
T is OH, OR, —NHCOCH$_3$, or NHCOR;
Z is NO$_2$, CN, COOH, COR, NHCOR or CONHR;
Y is CF$_3$, F, I, Br, Cl, CN, C(R)$_3$ or Sn(R)$_3$;
R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH;
R$_1$ is CH$_3$, CH$_2$F, CHF$_2$, CF$_3$, CH$_2$CH$_3$, or CF$_2$CF$_3$;
Q$_1$ is hydrogen, substituted or unsubstituted linear or branched alkyl, substituted or unsubstituted aryl, substituted or unsubstituted phenyl, F, Cl, Br, I, CF$_3$, CN, NO$_2$, substituted or unsubstituted cycloalkyl, substituted or unsubstituted heterocycloalkyl, substituted or unsubstituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO, or OCN;
Q$_2$ is hydrogen, substituted or unsubstituted linear or branched alkyl, substituted or unsubstituted aryl, substituted or unsubstituted phenyl, F, Cl, Br, I, CF$_3$, CN, NO$_2$, substituted or unsubstituted cycloalkyl, substituted or unsubstituted heterocycloalkyl, substituted or unsubstituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO, or OCN;

or

Q₁ and Q₂ are joined together to form a substituted or unsubstituted C₅-C₈ carbocyclic or heterocyclic ring.

In another embodiment, the prostate cancer is advanced prostate cancer, castration resistant prostate cancer (CRPC), metastatic CRPC (mCRPC), non-metastatic CRPC (nmCRPC), high-risk nmCRPC or any combination thereof. In another embodiment, the prostate cancer depends on AR-FL and/or AR-SV for proliferation. In another embodiment, the subject further receives androgen deprivation therapy (ADT). In another embodiment, the subject has failed androgen deprivation therapy (ADT). In another embodiment, the cancer is resistant to treatment with an androgen receptor antagonist. In another embodiment, the cancer is resistant to treatment with enzalutamide, bicalutamide, abiraterone, ARN-509, AZD-3514, galeterone, ASC-J9, flutamide, hydroxyflutamide, nilutamide, cyproterone acetate, ketoconazole, spironolactone, or any combination thereof. In another embodiment, administering the compound to a subject reduces the levels of AR, AR-full length (AR-FL), AR-FL with antiandrogen resistance-conferring AR-LBD mutations, AR-splice variant (AR-SV), gene-amplified AR, or any combination thereof, in said subject.

In one embodiment, this invention provides a method of treating, suppressing, reducing the incidence, reducing the severity, or inhibiting the progression of prostate cancer (PCa) and its symptoms, or increasing the survival of a male subject suffering from prostate cancer comprising administering to said subject a therapeutically effective amount of a compound or its isomer, pharmaceutically acceptable salt, pharmaceutical product, polymorph, hydrate or any combination thereof, represented by a compound of formula VII:

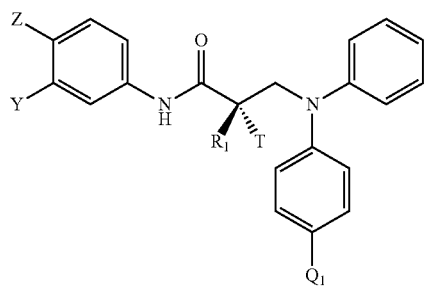

VII wherein
T is OH, OR, —NHCOCH₃, or NHCOR;
Z is NO₂, CN, COOH, COR, NHCOR or CONHR;
Y is CF₃, F, I, Br, Cl, CN, C(R)₃ or Sn(R)₃;
R is alkyl, haloalkyl, dihaloalkyl, trihaloalkyl, CH₂F, CHF₂, CF₃, CF₂CF₃, aryl, phenyl, F, Cl, Br, I, alkenyl or OH;
R₁ is CH₃, CH₂F, CHF₂, CF₃, CH₂CH₃, or CF₂CF₃; and
Q₁ is hydrogen, substituted or unsubstituted linear or branched alkyl, substituted or unsubstituted aryl, substituted or unsubstituted phenyl, F, Cl, Br, I, CF₃, CN, NO₂, substituted or unsubstituted cycloalkyl, substituted or unsubstituted heterocycloalkyl, substituted or unsubstituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO, or OCN.

In another embodiment, the prostate cancer is advanced prostate cancer, castration resistant prostate cancer (CRPC), metastatic CRPC (mCRPC), non-metastatic CRPC (nmCRPC), high-risk nmCRPC or any combination thereof. In another embodiment, the prostate cancer depends on AR-FL and/or AR-SV for proliferation. In another embodiment, the subject further receives androgen deprivation therapy (ADT). In another embodiment, the subject has failed androgen deprivation therapy (ADT). In another embodiment, the cancer is resistant to treatment with an androgen receptor antagonist. In another embodiment, the cancer is resistant to treatment with enzalutamide, bicalutamide, abiraterone, ARN-509, AZD-3514, galeterone, ASC-J9, flutamide, hydroxyflutamide, nilutamide, cyproterone acetate, ketoconazole, spironolactone, or any combination thereof. In another embodiment, administering the compound to a subject reduces the levels of AR, AR-full length (AR-FL), AR-FL with antiandrogen resistance-conferring AR-LBD mutations, AR-splice variant (AR-SV), gene-amplified AR, or any combination thereof, in said subject.

In one embodiment, this invention provides a method of treating, suppressing, reducing the incidence, reducing the severity, or inhibiting the progression of prostate cancer (PCa) and its symptoms, or increasing the survival of a male subject suffering from prostate cancer comprising administering to said subject a therapeutically effective amount of a compound or its isomer, pharmaceutically acceptable salt, pharmaceutical product, polymorph, hydrate or any combination thereof, selected from any one of the following structures:

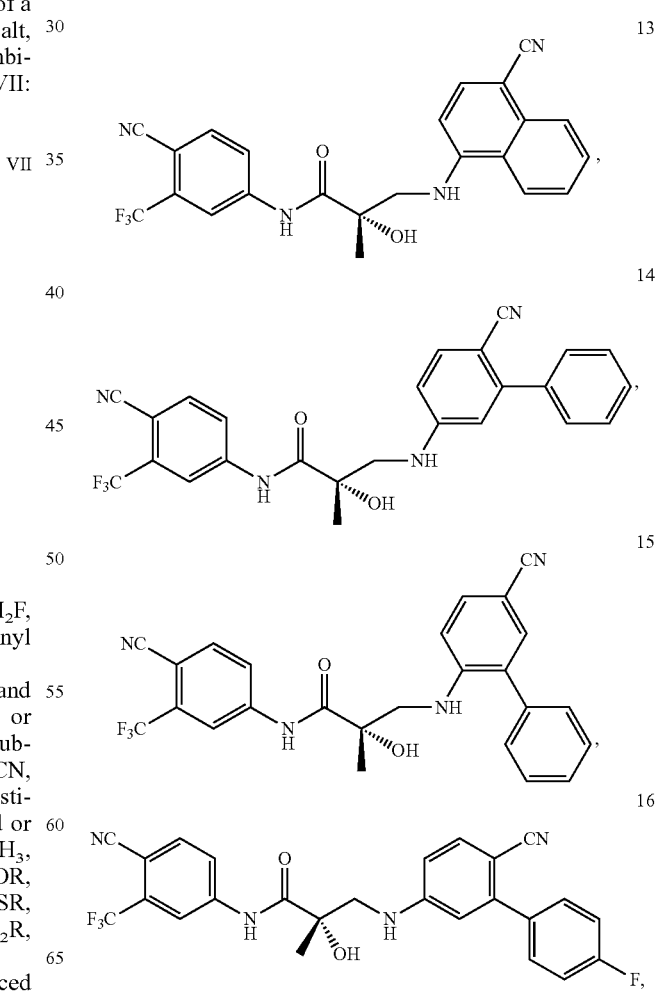

-continued

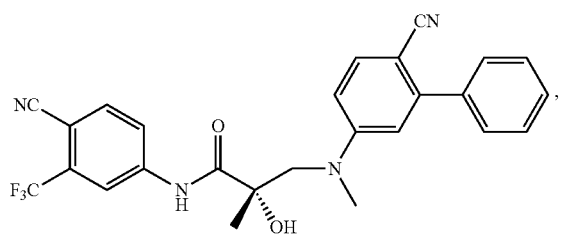

17

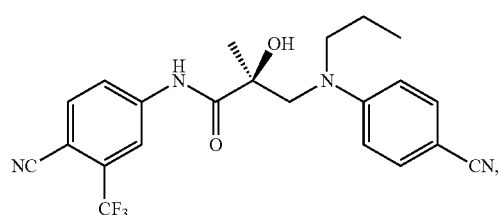

17a

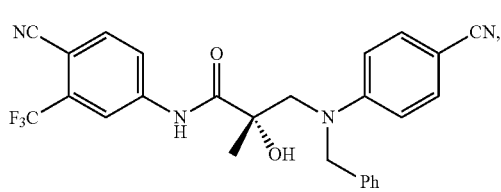

18

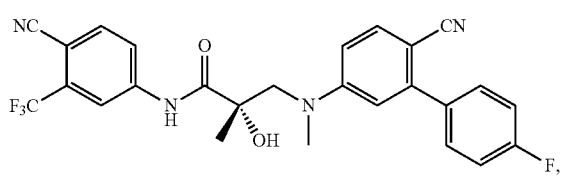

19

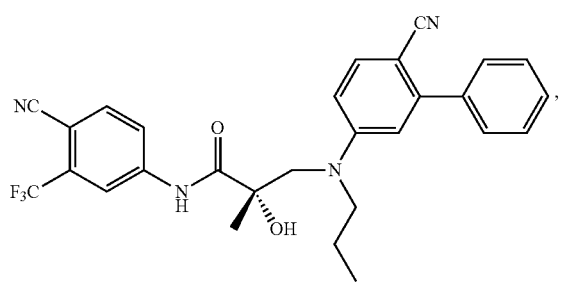

20

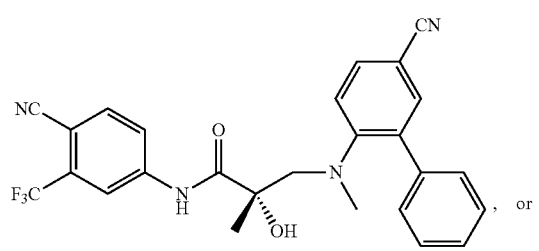

21

-continued

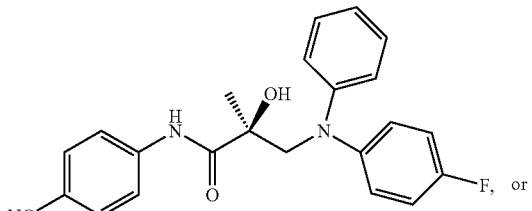

49

, or

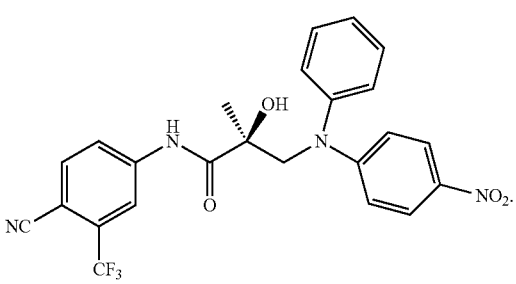

50

In another embodiment, the prostate cancer is advanced prostate cancer, castration resistant prostate cancer (CRPC), metastatic CRPC (mCRPC), non-metastatic CRPC (nm-CRPC), high-risk nmCRPC or any combination thereof. In another embodiment, the prostate cancer depends on AR-FL and/or AR-SV for proliferation. In another embodiment, the subject further receives androgen deprivation therapy (ADT). In another embodiment, the subject has failed androgen deprivation therapy (ADT). In another embodiment, the cancer is resistant to treatment with an androgen receptor antagonist. In another embodiment, the cancer is resistant to treatment with enzalutamide, bicalutamide, abiraterone, ARN-509, AZD-3514, galeterone, ASC-J9, flutamide, hydroxyflutamide, nilutamide, cyproterone acetate, ketoconazole, spironolactone, or any combination thereof. In another embodiment, administering the compound to a subject reduces the levels of AR, AR-full length (AR-FL), AR-FL with antiandrogen resistance-conferring AR-LBD mutations, AR-splice variant (AR-SV), gene-amplified AR, or any combination thereof, in said subject.

In one embodiment, the methods of this invention are directed to treating, suppressing, reducing the incidence, reducing the severity, inhibiting, providing palliative care, or increasing the survival of a subject suffering from prostate cancer. In one embodiment, the methods of this invention are directed to methods of treating, suppressing, reducing the incidence, reducing the severity, inhibiting, providing palliative care, or increasing the survival of advanced prostate cancer in a subject. In one embodiment, the methods of this invention are directed to treating, suppressing, reducing the incidence, reducing the severity, inhibiting, providing palliative care, or increasing the survival of a subject suffering from castration resistant prostate cancer (CRPC). In one embodiment, the methods of this invention are directed to treating, suppressing, reducing the incidence, reducing the severity, inhibiting, providing palliative care, or increasing the survival of a subject suffering from metastatic castration resistant prostate cancer (mCRPC). In one embodiment, the methods of this invention are directed to treating, suppressing, reducing the incidence, reducing the severity, inhibiting, providing palliative care, or increasing the survival of a subject suffering from non-metastatic castration resistant prostate cancer (nmCRPC). In one embodiment, the nmCRPC is high-risk nmCRPC. In another embodiment, the subject has high or increasing prostate specific antigen (PSA) levels.

In one embodiment, this invention provides a method of treating, suppressing, reducing the incidence, reducing the severity, or inhibiting the progression of prostate cancer (PCa) and its symptoms, or increasing the survival of a male subject suffering from prostate cancer comprising administering to said subject a therapeutically effective amount of a SARD compound or its isomer, pharmaceutically acceptable salt, pharmaceutical product, polymorph, hydrate or any combination thereof, said compound is represented by a compound of formulas I-VII, or any one of compounds 13-21, 49, 50 and 17a.

In one embodiment, this invention provides a method of treating, suppressing, reducing the incidence, reducing the severity, or inhibiting the progression of advanced prostate cancer and its symptoms, or increasing the survival of a male subject suffering from advanced prostate cancer comprising administering to said subject a therapeutically effective amount of a SARD compound or its isomer, pharmaceutically acceptable salt, pharmaceutical product, polymorph, hydrate or any combination thereof, said compound is represented by a compound of formulas I-VII, or any one of compounds 13-21, 49, 50 and 17a.

In one embodiment, this invention provides a method of treating, suppressing, reducing the incidence, reducing the severity, or inhibiting the progression of metastatic prostate cancer and its symptoms, or increasing the survival of a male subject suffering from metastatic prostate cancer comprising administering to said subject a therapeutically effective amount of a SARD compound or its isomer, pharmaceutically acceptable salt, pharmaceutical product, polymorph, hydrate or any combination thereof, said compound is represented by a compound of formulas I-VII, or any one of compounds 13-21, 49, 50 and 17a.

In one embodiment, this invention provides a method of treating, suppressing, reducing the incidence, reducing the severity, or inhibiting the progression of castration resistant prostate cancer (CRPC) and its symptoms, or increasing the survival of a male subject suffering from castration resistant prostate cancer (CRPC) comprising administering to said subject a therapeutically effective amount of a SARD compound or its isomer, pharmaceutically acceptable salt, pharmaceutical product, polymorph, hydrate or any combination thereof, said compound is represented by a compound of formulas I-VII, or any one of compounds 13-21, 49, 50 and 17a.

In one embodiment, the SARD compounds as described herein and/or compositions comprising the same may be used for treating, suppressing, reducing the incidence, reducing the severity, or inhibiting the progression of castration resistant prostate cancer (CRPC) and its symptoms, or increasing the survival of men with castration resistant prostate cancer. In another embodiment, the CRPC is metastatic CRPC (mCRPC). In another embodiment, the CRPC is non-metastatic CRPC (nmCRPC). In one embodiment, the nmCRPC is high-risk nmCRPC. In another embodiment, the subject further receives androgen deprivation therapy.

As used herein, the terms "increase" and "prolong" may be used interchangeably having all the same meanings and qualities, wherein these terms may in one embodiment refer to a lengthening of time. In another embodiment, as used herein, the terms "increase", increasing" "increased" may be used interchangeably and refer to an entity becoming progressively greater (as in size, amount, number, or intensity), wherein for example the entity is sex hormone-binding globulin (SHBG) or prostate-specific antigen (PSA).

In one embodiment, the compounds as described herein and/or compositions comprising the same may be used for increasing metastasis-free survival (MFS) in a subject suffering from non-metastatic prostate cancer. In one embodiment, the non-metastatic prostate cancer is non-metastatic advanced prostate cancer. In another embodiment, the non-metastatic prostate cancer is non-metastatic CRPC (nmCRPC). In one embodiment, the nmCRPC is high-risk nmCRPC.

In one embodiment, the SARD compounds as described herein and/or compositions comprising the same may be used to provide a dual action, for example treating prostate cancer and preventing metastases. In one embodiment, the prostate cancer being treated is advanced prostate cancer. In one embodiment, the prostate cancer being treated is castration resistant prostate cancer (CRPC). In one embodiment, the prostate cancer being treated is metastatic CRPC (mCRPC). In one embodiment, the prostate cancer being treated is non-metastatic CRPC (nmCRPC). In one embodiment, the nmCRPC is high-risk nmCRPC.

Men with advanced prostate cancer who are at high risk for progression to castration resistant prostate cancer (CRPC), in one embodiment, are men on ADT with serum total testosterone concentrations greater than 20 ng/dL or in another embodiment, men with advanced prostate cancer who at the time of starting ADT had either (1) confirmed Gleason pattern 4 or 5 prostate cancer, (2) metastatic prostate cancer, (3) a PSA doubling time <3 months, (4) a PSA ≥20 ng/mL, or (5) a PSA relapse in <3 years after definitive local therapy (radical prostatectomy or radiation therapy).

Men with high risk non-metastatic castration resistant prostate cancer (high-risk nmCRPC) may include those with rapid PSA doubling times, having an expected progression-free survival of approximately 18 months or less (Miller K, Moul J W, Gleave M, et al. 2013. Phase III, randomized, placebo-controlled study of once-daily oral zibotentan (ZD4054) in patients with non-metastatic castration-resistant prostate cancer. *Prostate Canc Prost Dis.* February; 16:187-192). This relatively rapid progression of their disease underscores the importance of novel therapies for these individuals. In one embodiment, the PSA levels are greater than 8 ng/mL in a subject suffering from high-risk nmCRPC. In one embodiment, the PSA doubling time is less than 8 months in a subject suffering from high-risk nmCRPC. In another embodiment, the PSA doubling time is less than 10 months in a subject suffering from high-risk nmCRPC. In one embodiment, the total serum testosterone levels are greater than 20 ng/mL in a subject suffering from high-risk nmCRPC. In one embodiment, the serum free testosterone levels are greater than those observed in an orchiechtomized male in a subject suffering from high-risk nmCRPC.

In one embodiment, the compounds as described herein and/or compositions comprising the same may be used in combination with LHRH agonist or antagonist for increasing the progression free survival or overall survival of a subject suffering from prostate cancer. In another embodiment, the prostate cancer is advanced prostate cancer. In another embodiment, the prostate cancer is castration resistant prostate cancer (CRPC). In another embodiment, the CRPC is metastatic CRPC (mCRPC). In another embodiment, the CRPC is non-metastatic CRPC (nmCRPC). In one embodiment, the nmCRPC is high-risk nmCRPC. In another embodiment, the subject is surgically castrated. In another embodiment, the subject is chemically castrated.

In one embodiment, the compounds as described herein and/or compositions comprising the same may be used in combination with anti-programmed death receptor 1 (anti-PD-1) drugs (e.g., AMP-224, nivolumab, pembrolizumab, pidilizumab, AMP-554, and the like) for increasing the progression free survival or overall survival of a subject suffering from prostate cancer. In another embodiment, the prostate cancer is advanced prostate cancer. In another embodiment, the prostate cancer is castration resistant prostate cancer (CRPC). In another embodiment, the CRPC is metastatic CRPC (mCRPC). In another embodiment, the CRPC is non-metastatic CRPC (nmCRPC). In one embodiment, the nmCRPC is high-risk nmCRPC. In another embodiment, the subject is surgically castrated. In another embodiment, the subject is chemically castrated.

In one embodiment, the compounds as described herein and/or compositions comprising the same may be used in combination with anti-PD-L1 drugs (e.g., BMS-936559, MEDI4736, MPDL3280A, MEDI4736, MSB0010718C, and the like) for increasing the progression free survival or overall survival of a subject suffering from prostate cancer. In another embodiment, the prostate cancer is advanced prostate cancer. In another embodiment, the prostate cancer is castration resistant prostate cancer (CRPC). In another embodiment, the CRPC is metastatic CRPC (mCRPC). In another embodiment, the CRPC is non-metastatic CRPC (nmCRPC). In one embodiment, the nmCRPC is high-risk nmCRPC. In another embodiment, the subject is surgically castrated. In another embodiment, the subject is chemically castrated.

In certain embodiments, treatment of prostate cancer, advanced prostate cancer, CRPC, mCRPC and/or nmCRPC may result in clinically meaningful improvement in prostate cancer related symptoms, function and/or survival. Clinically meaningful improvements include but are not limited to increasing radiographic progression free survival (rPFS) if cancer is metastatic, and increasing metastasis-free survival (MFS) if cancer is non-metastatic.

In one embodiment, the compounds as described herein and/or compositions comprising the same may be used for increasing the survival of men with castration resistant prostate cancer (CRPC). In another embodiment, the CRPC is metastatic CRPC (mCRPC). In another embodiment, the CRPC is non-metastatic CRPC (nmCRPC). In one embodiment, the nmCRPC is high-risk nmCRPC. In another embodiment, the subject further receives androgen deprivation therapy.

In one embodiment, levels of prostate specific antigen (PSA) considered normal are age dependent. In one embodiment, levels of prostate specific antigen (PSA) considered normal are dependent on the size of a male subject's prostate. In one embodiment, PSA levels in the range between 2.5-10 ng/mL are considered "borderline high". In another embodiment, PSA levels above 10 ng/mL are considered "high".

In one embodiment, the rate of change or "PSA velocity" is high. In one embodiment, a rate of change or "PSA velocity" greater than 0.75/year is considered high.

In one embodiment, this invention provides a method of lowering serum prostate specific antigen (PSA) levels in a male subject suffering from prostate cancer, advanced prostate cancer, metastatic prostate cancer or castration resistant prostate cancer (CRPC), comprising administering a therapeutically effective amount of a SARD compound or its isomer, pharmaceutically acceptable salt, pharmaceutical product, polymorph, hydrate or any combination thereof, said compound is represented by the structure of formulas I-VII, or any one of compounds 13-21, 49, 50 and 17a.

In one embodiment, this invention is directed to treatment of a subject with high or increasing PSA levels comprising administering a SARD compound of this invention. In one embodiment, this invention is directed to treatment of a subject with high or increasing PSA levels despite ongoing ADT or a history of ADT, surgical castration or despite treatment with antiandrogens and/or LHRH agonist. In another embodiment, the treatment makes use of compounds of formulas I-VII, or any one of compounds 13-21, 49, 50 and 17a.

In one embodiment, this invention provides a method of treating, suppressing, reducing the incidence, reducing the severity, or inhibiting the progression of castration resistant prostate cancer (CRPC) and its symptoms, or increasing the survival of men with castration resistant prostate cancer comprising administering a therapeutically effective amount of a compound of formulas I-VII or its isomer, pharmaceutically acceptable salt, pharmaceutical product, polymorph, hydrate or any combination thereof. In another embodiment, the compound is compound 13. In another embodiment, the compound is compound 14. In another embodiment, the compound is compound 15. In another embodiment, the compound is compound 16. In another embodiment, the compound is compound 17. In another embodiment, the compound is compound 17a. In another embodiment, the compound is compound 18. In another embodiment, the compound is compound 19. In another embodiment, the compound is compound 20. In another embodiment, the compound is compound 21. In another embodiment, the compound is compound 49. In another embodiment, the compound is compound 50.

In one embodiment, this invention provides a method of secondary hormonal therapy that reduces serum PSA in a male subject suffering from castration resistant prostate cancer (CRPC) comprising administering a therapeutically effective amount of a compound of formulas I-VII or its isomer, pharmaceutically acceptable salt, pharmaceutical product, polymorph, hydrate or any combination thereof. In another embodiment, the castration is surgical castration. In another embodiment, with regards to the methods described above, the prostate cancer depends on AR-FL and/or AR-SV for proliferation. In another embodiment, the cancer is resistant to treatment with an androgen receptor antagonist. In another embodiment, the cancer is resistant to treatment with enzalutamide, bicalutamide, abiraterone, ARN-509, AZD-3514, galeterone, ASC-J9, flutamide, hydroxyflutamide, nilutamide, cyproterone acetate, ketoconazole, spironolactone, or any combination thereof. In another embodiment, administration of the compounds of formulas I-VII, reduces the levels of AR, AR-full length (AR-FL), AR-FL with antiandrogen resistance-conferring AR-LBD mutations, AR-splice variant (AR-SV), amplications of the AR gene within the tumor, or any combination thereof, in the subject. In another embodiment, the castration is surgical castration. In another embodiment, the castration is chemical castration. In another embodiment, the CRPC is metastatic CRPC (mCRPC). In another embodiment, the CRPC is non-metastatic CRPC (nmCRPC). In one embodiment, the nmCRPC is high-risk nmCRPC. In another embodiment, the method further increases radiographic progression free survival (rPFS) in a subject suffering from a metastatic cancer. In another embodiment, the method further increases metastasis-free survival (MFS) in a subject suffering from non-metastatic cancer. In one embodiment, the method may be used to provide a dual action, for example treating prostate cancer and preventing metastases. In another embodiment, the subject has failed androgen deprivation therapy (ADT). In another embodiment, the subject further receives androgen deprivation therapy (ADT). In another embodiment, the subject further receives LHRH agonist or antagonist. In another embodiment, the LHRH agonist is leuprolide acetate. In another embodiment, the subject had undergone orchidectomy. In another embodiment, the subject has high or increasing prostate specific antigen (PSA) levels. In another embodiment, the subject is a prostate cancer patient. In another embodiment, the subject is a prostate cancer patient on ADT. In another embodiment, the subject is a prostate cancer patient on ADT with castrate levels of total T. In another embodiment, the subject is an advanced prostate cancer patient. In another embodiment, the subject is an advanced prostate cancer patient on ADT. In another embodiment, the subject is an advanced prostate cancer patient on ADT with castrate levels of total T. In another embodiment, the subject is a CRPC patient. In another embodiment, the subject is a CRPC patient on ADT. In another embodiment, the subject is a CRPC patient on ADT with castrate levels of total T. In another embodiment, the subject is a metastatic castration resistant prostate cancer (mCRPC) patient. In another embodiment, the subject is a mCRPC patient maintained on ADT. In another embodiment, the subject is a mCRPC patient maintained on ADT with castrate levels of total T. In another embodiment, the subject is a non-metastatic castration resistant prostate cancer (nmCRPC) patient. In another embodiment, the subject is an nmCRPC patient maintained on ADT. In another embodiment, the subject is an nmCRPC patient maintained on ADT with castrate levels of total T. In one embodiment, the nmCRPC is high-risk nmCRPC. In another embodiment, the method further treats, suppresses, reduces the incidence, reduces the severity, or inhibits advanced prostate cancer. In another embodiment, the method further provides palliative treatment of advanced prostate cancer.

In one embodiment, this invention is directed to a method of reducing the levels of AR, AR-full length, AR-FL with antiandrogen resistance-conferring AR-LBD mutations, and/or AR-splice variants in a subject, comprising administering to said subject a therapeutically effective amount of a SARD compound according to this invention, or its isomer, pharmaceutically acceptable salt, pharmaceutical product, polymorph, hydrate or any combination thereof. In another embodiment, the reduction is achieved by degradation of said AR, AR-full length (AR-FL) and/or AR-splice variants (AR-SV). In another embodiment, the reduction is achieved by inhibition of said AR, AR-full length (AR-FL) and/or AR-splice variants (AR-SV). In another embodiment, the reduction is achieved by dual AR-SV/AR-FL degradation and AR-SV/AR-FL inhibitory functions.

In one embodiment, this invention is directed to a method of reducing the levels of AR-splice variants in a subject, comprising administering to said subject a therapeutically effective amount of a SARD compound according to this invention, or its isomer, pharmaceutically acceptable salt, pharmaceutical product, polymorph, hydrate or any combination thereof. In another embodiment, the method further reduces the levels of AR-full length (AR-FL) in the subject. In another embodiment, the reduction is achieved by degradation of said AR-splice variants (AR-SV). In another embodiment, the reduction is further achieved by degradation of said AR-FL. In another embodiment, the reduction is achieved by inhibition of said AR-splice variants (AR-SV). In another embodiment, the reduction is further achieved by inhibition of said AR-FL. In another embodiment, the reduction is achieved by dual AR-SV degradation and AR-SV inhibitory functions. In another embodiment, the reduction is achieved by dual AR-FL degradation and AR-FL inhibitory functions.

In one embodiment, "a subject suffering from castration resistant prostate cancer" refers to a subject which has been previously treated with androgen deprivation therapy (ADT), has responded to the ADT and currently has a serum PSA >2 ng/mL or >2 ng/mL and representing a 25% increase above the nadir achieved on the ADT. In another embodiment, the term refers to a subject which despite being maintained on androgen deprivation therapy is diagnosed to have serum PSA progression. In another embodiment, the subject has a castrate level of serum total testosterone (<50 ng/dL). In another embodiment, the subject has a castrate level of serum total testosterone (<20 ng/dL). In another embodiment, the subject has rising serum PSA on two successive assessments at least 2 weeks apart. In another embodiment, the subject had been effectively treated with ADT. In another embodiment, the subject has a history of serum PSA response after initiation of ADT. In another embodiment, the subject has been treated with ADT and had an initial serum PSA response, but now has a serum PSA >2 ng/mL and a 25% increase above the nadir observed on ADT. In one embodiment, the CRPC is metastatic CRPC (mCRPC). In another embodiment, the CRPC is non-metastatic CRPC (nmCRPC). In one embodiment, the nmCRPC is high-risk nmCRPC.

The term "serum PSA response" refers to, in one embodiment, at least 90% reduction in serum PSA value prior to the initiation of ADT, to <10 ng/mL OR undetectable level of serum PSA (<0.2 ng/mL) at any time, or in another embodiment to at least 50% decline from baseline in serum PSA, or in another embodiment to at least 90% decline from baseline in serum PSA, or in another embodiment to at least 30% decline from baseline in serum PSA, or in another embodiment to at least 10% decline from baseline in serum PSA.

The term "serum PSA progression" refers to in one embodiment, a 25% or greater increase in serum PSA and an absolute increase of 2 ng/ml or more from the nadir; or in another embodiment, to serum PSA >2 ng/mL, or >2 ng/mL and a 25% increase above the nadir after the initiation of androgen deprivation therapy (ADT).

In another embodiment, the term "nadir" refers to the lowest PSA level while a patient is undergoing ADT.

Testosterone can be measured as "free" (that is, bioavailable and unbound) or as "total" (including the percentage which is protein bound and unavailable) serum levels. In one embodiment, total serum testosterone comprises free testosterone and bound testosterone.

The methods of this invention comprise administering a combination of forms of ADT and a compound of this invention. In one embodiment, forms of ADT include a LHRH agonist. In another embodiment, the LHRH agonist includes leuprolide acetate (Lupron®)(U.S. Pat. No. 5,480,656; U.S. Pat. Nos. 5,575,987; 5,631,020; 5,643,607; 5,716,640; 5,814,342; 6,036,976 which are all incorporated by reference herein) or goserelin acetate (Zoladex®) (U.S. Pat. Nos. 7,118,552; 7,220,247; 7,500,964 which are all incorporated by reference herein). In one embodiment, forms of ADT include an LHRH antagonist. In another embodiment, the LHRH antagonist includes degarelix. In one embodiment, forms of ADT include reversible antiandrogens. In another embodiment, the antiandrogens include bicalutamide, flutamide, finasteride, dutasteride, enzalutamide, nilutamide, chlormadinone, abiraterone or any combination thereof. In one embodiment, forms of ADT include bilateral orchidectomy.

In one embodiment, this invention provides a method of treating, suppressing, reducing the incidence, reducing the severity, or inhibiting the progression of castration resistant prostate cancer (CRPC) and its symptoms, or increasing the survival of men with castration resistant prostate cancer comprising administering a therapeutically effective amount of a combination of one or more forms of ADT and a compound of formulas I-VII or its isomer, pharmaceutically acceptable salt, pharmaceutical product, polymorph, hydrate or any combination thereof. In another embodiment, the subject has failed androgen deprivation therapy (ADT).

In one embodiment, this invention provides a method of lowering serum PSA levels in a male subject suffering from castration resistant prostate cancer (CRPC) comprising administering a therapeutically effective amount of a combination of one or more forms of ADT and a compound of formulas I-VII or its isomer, pharmaceutically acceptable salt, pharmaceutical product, polymorph, hydrate or any combination thereof. In another embodiment, the subject has failed androgen deprivation therapy (ADT).

In one embodiment, the methods of this invention comprise administering a therapeutically effective amount of an antiandrogen and a compound of this invention. In one embodiment, the methods of this invention comprise administering a therapeutically effective amount of an LHRH agonist and a compound of this invention. In one embodiment, the methods of this invention comprise administering a therapeutically effective amount of an antiandrogen, LHRH agonist and a compound of this invention. In another embodiment, the compound is compound of formulas I-VII. In another embodiment, the compound is any one of compounds 13-21, 49, 50 and 17a.

In one embodiment, the methods of this invention comprise administering a therapeutically effective amount of a lyase inhibitor (e.g., abiraterone) and a compound of this invention. In another embodiment, the compound is a compound of formulas I-VII. In another embodiment, the compound is any one of compounds 13-21, 49, 50 and 17a.

In another embodiment, this invention provides a method for androgen deprivation therapy (ADT) in a subject, comprising administering a therapeutically effective amount of a compound of formulas I-VII or its isomer, pharmaceutically acceptable salt, pharmaceutical product, polymorph, hydrate or any combination thereof. In another embodiment, said subject has prostate cancer. In another embodiment, the prostate cancer is castration resistant prostate cancer (CRPC). In another embodiment, the CRPC is metastatic CRPC (mCRPC). In one embodiment, the CRPC is non-metastatic castration resistant prostate cancer (nmCRPC). In one embodiment, the nmCRPC is high-risk nmCRPC. In another embodiment, the compound is any one of compounds 13-21, 49, 50 and 17a. In another embodiment, the subject has failed androgen deprivation therapy (ADT). In another embodiment, the subject further receives androgen deprivation therapy (ADT).

In one embodiment, this invention provides a method of treating prostate cancer or delaying the progression of prostate cancer comprising administering a SARD compound of this invention. In one embodiment, this invention provides a method of preventing and/or treating the recurrence of prostate cancer comprising administering a SARD compound of this invention. In another embodiment, the prostate cancer is castration resistant prostate cancer (CRPC). In another embodiment, the CRPC is metastatic CRPC (mCRPC). In one embodiment, the CRPC is non-metastatic castration resistant prostate cancer (nmCRPC). In one embodiment, the nmCRPC is high-risk nmCRPC.

In one embodiment, this invention provides a method of increasing the survival of a subject having prostate cancer, advanced prostate cancer, castration resistant prostate cancer or metastatic castration resistant prostate cancer or non-metastatic castration resistant prostate cancer or high-risk non metastatic castration resistant prostate cancer, comprising administering a compound of this invention. In another embodiment, administering a compound of this invention in combination with LHRH analogs, reversible antiandrogens (such as bicalutamide, flutamide, or enzalutamide), anti-estrogens, anticancer drugs, 5-alpha reductase inhibitors, aromatase inhibitors, progestins, selective androgen receptor modulators (SARMs) or agents acting through other nuclear hormone receptors. In another embodiment, the subject has failed androgen deprivation therapy (ADT). In another embodiment the compound is any one of compounds 13-21, 49, 50 and 17a.

The term "advanced prostate cancer" refers to metastatic cancer having originated in the prostate, and having widely metastasized to beyond the prostate such as the surrounding tissues to include the seminal vesicles the pelvic lymph nodes or bone, or to other parts of the body. Prostate cancer pathologies are graded with a Gleason grading from 1 to 5 in order of increasing malignancy. In another embodiment, patients with significant risk of progressive disease and/or death from prostate cancer should be included in the definition and that any patient with cancer outside the prostate capsule with disease stages as low as IIB clearly has "advanced" disease. In another embodiment, "advanced prostate cancer" can refer to locally advanced prostate cancer.

Men with advanced prostate cancer often receive treatment to block the production of androgens, which are male sex hormones that may help prostate tumors grow. However, prostate cancers that initially respond to antiandrogen therapy eventually develop the ability to grow without androgens. Such cancers are often referred to as hormone refractory, androgen independent, or castration resistant.

In one embodiment, the advanced prostate cancer is castration resistant prostate cancer.

The term "castration resistant prostate cancer" (CRPC) refers to advanced prostate cancer that is worsening or progressing while the patient remains on ADT or other therapies to reduce testosterone, or prostate cancer which is considered hormone refractory, hormone naïve, androgen independent or chemical or surgical castration resistant. In another embodiment, CRPC is a result of AR activation by intracrine androgen synthesis. In another embodiment, CRPC is a result of expression of AR splice variants (AR-SV) that lack ligand binding domain (LBD). In another embodiment, CRPC is a result of expression of AR-LBD mutations with potential to resist antagonists. In another embodiment, castration resistant prostate cancer (CRPC) is an advanced prostate cancer which developed despite ongoing ADT and/or surgical castration. In one embodiment, castration resistant prostate cancer is defined as prostate cancer that continues to progress or worsen or adversely affect the health of the patient despite prior surgical castration, continued treatment with gonadotropin releasing hormone agonists (e.g., leuprolide) or antagonists (e.g., degarelix), antiandrogens (e.g., bicalutamide, flutamide, enzalutamide, ketoconazole, aminoglutethamide), chemotherapeutic agents (e.g., docetaxel, paclitaxel, cabazitaxel, adriamycin, mitoxantrone, estramustine, cyclophosphamide), kinase inhibitors (imatinib (Gleevec®) or gefitinib (Iressa®), cabozantinib (Cometriq™, also known as XL184)) or other prostate cancer therapies (e.g., vaccines (sipuleucel-T (Provenge®), GVAX, etc.), herbal (PC-SPES) and lyase inhibitor (abiraterone)) as evidenced by increasing or higher serum levels of prostate specific antigen (PSA), metastasis, bone metastasis, pain, lymph node involvement, increasing size or serum markers for tumor growth, worsening diagnostic markers of prognosis, or patient condition.

In one embodiment, castration resistant prostate cancer is defined as hormone naïve prostate cancer.

Many early prostate cancers require androgens for growth, but advanced prostate cancers are in some embodiments, androgen-independent, or hormone naïve. In one embodiment, in men with castration resistant prostate cancer, the tumor cells may have the ability to grow in the absence of androgens (hormones that promote the development and maintenance of male sex characteristics).

In one embodiment, the term "androgen deprivation therapy" (ADT) or "traditional androgen deprivation therapy" is directed to orchiectomy (surgical castration) wherein the surgeon removes the testicles. In another embodiment, the term "androgen deprivation therapy" or "traditional androgen deprivation therapy" is directed to administering luteinizing hormone-releasing hormone (LHRH) analogs: these drugs lower the amount of testosterone made by the testicles. Examples of LHRH analogs available in the United States include leuprolide (Lupron®, Viadur®, Eligard®), goserelin (Zoladex®), triptorelin (Trelstar®), and histrelin (Vantas®). In another embodiment, the term "androgen deprivation therapy" or "traditional androgen deprivation therapy" is directed to administering antiandrogens: Antiandrogens block the body's ability to use any androgens. Even after orchiectomy or during treatment with LHRH analogs, a small amount of androgens is still made by the adrenal glands. Examples of antiandrogens drugs include enzalutamide (Xtandi®), flutamide (Eulexin®), bicalutamide (Casodex®), and nilutamide (Nilandron®). In another embodiment, the term "androgen deprivation therapy" or "traditional androgen deprivation therapy" is directed to administering luteinizing hormone-releasing hormone (LHRH) antagonists such as abarelix (Plenaxis®) or degarelix (Firmagon®) (approved for use by the FDA in 2008 to treat advanced prostate cancer). In another embodiment, the term "androgen deprivation therapy" or "traditional androgen deprivation therapy" is directed to administering 5α-reductase inhibitors such as finasteride (Proscar®) and dutasteride (Avodart®): 5α-reductase inhibitors block the body's ability to convert testosterone to the more active androgen, 5α-dihydrotestosterone (DHT). In another embodiment, the term "androgen deprivation therapy" or "traditional androgen deprivation therapy" is directed to administering inhibitors of testosterone biosynthesis such as ketoconazole (Nizoral®). In another embodiment, the term "androgen deprivation therapy" or "traditional androgen deprivation therapy" is directed to administering estrogens such as diethylstilbestrol or 17β-estradiol. In another embodiment, the term "androgen deprivation therapy" or "traditional androgen deprivation therapy" is directed to administering 17α-hydroxylase/C17,20 lyase (CYP17A1) inhibitors such as abiraterone (Zytiga®).

In one embodiment, this invention provides a method of treating, suppressing, reducing the incidence, reducing the severity, increasing the survival, or inhibiting an antiandrogen-resistant prostate cancer. In another embodiment, the antiandrogen is bicalutamide, hydroxyflutamide, flutamide, or enzalutamide.

In one embodiment, this invention provides a method of treating, suppressing, reducing the incidence, reducing the severity, increasing the survival, or inhibiting an abiraterone-resistant prostate cancer.

Muscle atrophy (MA) is characterized by wasting away or diminution of muscle and a decrease in muscle mass. For example, post-polio MA is a muscle wasting that occurs as part of the post-polio syndrome (PPS). The atrophy includes weakness, muscle fatigue, and pain.

Another type of MA is X-linked spinal-bulbar muscular atrophy (SBMA—also known as Kennedy's Disease). This disease arises from a defect in the androgen receptor gene on the X chromosome, affects only males, and its onset is in late adolescence to adulthood. Proximal limb and bulbar muscle weakness results in physical limitations including dependence on a wheelchair in some cases. The mutation results in an extended polyglutamine tract at the N-terminal domain of the androgen receptor (polyQ AR). Binding and activation of the polyQ AR by endogeneous androgens (testosterone and DHT) results in unfolding and nuclear translocation of the mutant androgen receptor. These steps are required for pathogenesis and results in partial loss of transactivation function (i.e., an androgen insensitivity) and a poorly understood neuromuscular degeneration. Currently there are no disease-modifying treatments but rather only symptom directed treatments. Efforts to target the polyQ AR as the proximal mediator of toxicity by harnessing cellular machinery to promote its degradation hold promise for therapeutic intervention. Selective androgen receptor degraders such as those reported herein bind to and degrade a variety of androgen receptors (full length, splice variant, antiandrogen resistance mutants, etc.), indicating that they are promising leads for treatment of SBMA. This view is supported by the observation that peripheral polyQ AR anti-sense therapy rescues disease in mouse models of SBMA (Cell Reports 7, 774-784, May 8, 2014).

In one embodiment, this invention is directed to a method of treating, suppressing, reducing the incidence, reducing the severity, or inhibiting the progression of the Kennedy's disease comprising administering therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

As used herein, "androgen receptor associated conditions" or "androgen sensitive diseases or disorders" are conditions, diseases, or disorders that are modulated by or whose pathogenesis is dependent upon the activity of the androgen receptor. The androgen receptor is expressed in most tissues of the body however it is overexpressed in, inter alia, the prostate and skin. ADT has been the mainstay of prostate cancer treatment for many years, and SARD may also be useful also in treating various prostate cancers, benign prostatic hypertrophy, prostamegaly, and other maladies of the prostate.

In one embodiment, this invention is directed to a method of treating, suppressing, reducing the incidence, reducing the severity, or inhibiting the progression of benign prostatic hypertrophy comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of prostamegaly comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of hyperproliferative prostatic disorders and diseases comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

The effect of the AR on the skin is apparent in the gender dimorphism and puberty related dermatological problems common to teens and early adults. The hyperandrogenism of puberty stimulates terminal hair growth, sebum production, and predisposes male teens to acne, acne vulgaris, seborrhea, excess sebum, hidradenitis suppurativa, hirsutism, hypertrichosis, hyperpilosity, androgenic alopecia, male pattern baldness, and other dermatological maladies. Although antiandrogens theoretically should prevent the hyperandrogenic dermatological diseases discussed, they are limited by toxicities, sexual side effects, and lack of efficacy when topically applied. The SARDs of this invention potently inhibit ligand-dependent and ligand-independent AR activation, and have short biological half-lives in the serum, suggesting that topically formulated SARDs of this invention could be applied to the areas affected by acne, seborrheic dermatitis, and/or hirsutism without risk of systemic side effects.

In one embodiment, this invention is directed to a method of treating, suppressing, reducing the incidence, reducing the severity, or inhibiting the progression of acne comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of acne vulgaris comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of seborrhea comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of seborrheic dermatitis comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of hidradenitis supporativa comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of hirsutism comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of hypertrichosis comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of hyperpilosity comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of alopecia comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In some embodiments, the compounds as described herein and/or compositions may be used for applications in or treating hair loss, alopecia, androgenic alopecia, alopecia areata, alopecia secondary to chemotherapy, alopecia secondary to radiation therapy, alopecia induced by scarring or alopecia induced by stress. In one embodiment, "hair loss", or "alopecia", refers to baldness as in the very common type of male-pattern baldness. Baldness typically begins with patch hair loss on the scalp and sometimes progresses to complete baldness and even loss of body hair. Hair loss affects both males and females.

In one embodiment, this invention is directed to a method of treating, suppressing, reducing the incidence, reducing the severity, or inhibiting the progression of androgenic alopecia comprising administering a therapeutically effective amount of a compound of formula I-VII or its isomer, pharmaceutically acceptable salt, pharmaceutical product, polymorph, hydrate or any combination thereof. In another embodiment, the compound is any one of compounds 13-21, 49, 50 and 17a.

SARDs of this invention may also be useful in the treatment of hormonal conditions in females such as precocious puberty, early puberty, dysmenorrhea, amenorrhea, multilocular uterus syndrome, endometriosis, hysteromyoma, abnormal uterine bleeding, early menarche, fibrocystic breast disease, fibroids of the uterus, ovarian cysts, polycystic ovary syndrome, pre-eclampsia, eclampsia of pregnancy, preterm labor, premenstrual syndrome, and vaginal dryness.

In one embodiment, this invention is directed to a method of treating, suppressing, reducing the incidence, reducing the severity, or inhibiting the progression of precocious puberty or early puberty comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of dysmenorrhea or amenorrhea comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of multilocular uterus syndrome, endometriosis, hysteromyoma, or abnormal uterine bleeding comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of any hyperandrogenic diseases (for example polycystic ovary syndrome (PCOS)) comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of fibrocystic breast disease, fibroids of the uterus, ovarian cysts, or polycystic ovary syndrome comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of pre-eclampsia, eclampsia of pregnancy, preterm labor, premenstrual syndrome, or vaginal dryness comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

SARDS of this invention may also find utility in treatment of sexual perversion, hypersexuality, paraphilias, androgen psychosis, virilization, androgen insensitivity syndromes (AIS) such as complete AIS (CAIS) and partial AIS (PAIS), and improving ovulation in an animal.

In one embodiment, this invention is directed to a method of treating, suppressing, reducing the incidence, reducing the severity, or inhibiting the progression of sexual perversion, hypersexuality, or paraphilias comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of androgen psychosis comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of virilization comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of androgen insensitivity syndromes comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a. In one embodiment, the androgen insensitivity syndrome is a complete androgen insensitivity syndrome. In another embodiment, the androgen insensitivity syndrome is a partial androgen insensitivity syndrome.

In one embodiment, this invention is directed to a method of increasing, modulating, or improving ovulation in an animal comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

SARDs of this invention may also be useful for the treating of hormone-dependent cancers such as prostate cancer, breast cancer, testicular cancer, ovarian cancer, hepatocellular carcinoma, urogenital cancer, etc. Further, local or systemic SARD administration may be useful for treatment of precursors of hormone dependent cancers such as prostatic intraepithelial neoplasia (PIN) and atypical small acinar proliferation (ASAP).

In one embodiment, this invention is directed to a method of treating, suppressing, reducing the incidence, reducing the severity, or inhibiting the progression of breast cancer comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of testicular cancer comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of uterine cancer comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of ovarian cancer comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of urogenital cancer comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of precursors of prostate cancer comprising local or systemic administration of a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a. In one embodiment, the precursor of prostate cancers is prostatic intraepithelial neoplasia (PIN). In another embodiment, the precursor of prostate cancer is atypical small acinar proliferation (ASAP).

In one embodiment, this invention is directed to a method of treating, suppressing, reducing the incidence, reducing the severity, or inhibiting the progression of AR related solid tumors. In another embodiment, the tumor is hepatocellular carcinoma (HCC). In another embodiment, the tumor is bladder cancer. Serum testosterone may be positively linked to the development of HCC. Based on epidemiologic, experimental observations, and notably the fact that men have a substantially higher risk of bladder cancer than women, androgens and/or the AR also play a role in bladder cancer initiation.

SARD of this invention may also be useful for the treating other cancers containing AR such as breast, brain, skin, ovarian, bladder, lymphoma, liver, kidney, pancreas, endometrium, lung (e.g., NSCLC), colon, perianal adenoma, osteosarcoma, CNS, melanoma, hypercalcemia of malignancy and metastatic bone disease etc.

In one embodiment, this invention is directed to a method of treating, suppressing, reducing the incidence, reducing the severity, or inhibiting the progression of hypercalcemia of malignancy comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of metastatic bone disease comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of brain cancer comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of skin cancer comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of ovarian cancer comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of bladder cancer comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of lymphoma comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of liver cancer comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of renal cancer comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of osteosarcoma comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of pancreatic cancer comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of endometrial cancer comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of lung cancer comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a. In one embodiment, the lung cancer is non-small cell lung cancer (NSCLC).

In one embodiment, this invention is directed to a method of treating, suppressing, reducing the incidence, reducing the severity, or inhibiting the progression of a central nervous system cancer comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of colon cancer comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of melanoma comprising administering a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of amyotrophic lateral sclerosis (ALS) in a subject, comprising administering a therapeutically effective amount of the compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention is directed to a method of treating, suppressing, reducing the incidence, reducing the severity, or inhibiting the progression of uterine fibroids in a subject, comprising administering a therapeutically effective amount of the compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention provides a method of treating a subject suffering from a wound, or reducing the incidence of, or mitigating the severity of, or enhancing or hastening healing of a wound in a subject, the method comprises administering to said subject a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

In one embodiment, this invention provides a method of treating a subject suffering from a burn, or reducing the incidence of, or mitigating the severity of, or enhancing or hastening healing of a burn in a subject, the method comprises administering to said subject a therapeutically effective amount of a compound of formulas I-VII or its isomer, pharmaceutically acceptable salt, pharmaceutical product, polymorph, hydrate or any combination thereof. In another embodiment, the compound is any one of compounds 13-21, 49, 50 and 17a.

Wounds and/or ulcers are normally found protruding from the skin or on a mucosal surface or as a result of an infarction in an organ. A wound may be a result of a soft tissue defect or a lesion or of an underlying condition. In one embodiment, the term "wound" denotes a bodily injury with disruption of the normal integrity of tissue structures. The term is also intended to encompass the terms "sore", "lesion", "necrosis" and "ulcer". In one embodiment, the term "sore" refers to any lesion of the skin or mucous membranes and the term "ulcer" refers to a local defect, or excavation, of the surface of an organ or tissue, which is produced by the sloughing of necrotic tissue. Lesion generally relates to any tissue defect. Necrosis is related to dead tissue resulting from infection, injury, inflammation or infarctions. All of these are encompassed by the term "wound", which denotes any wound at any particular stage in the healing process including the stage before any healing has initiated or even before a specific wound like a surgical incision is made (prophylactic treatment).

Examples of wounds which can be prevented and/or treated in accordance with the present invention are, e.g., aseptic wounds, contused wounds, incised wounds, lacerated wounds, non-penetrating wounds (i.e. wounds in which there is no disruption of the skin but there is injury to underlying structures), open wounds, penetrating wounds, perforating wounds, puncture wounds, septic wounds, subcutaneous wounds, etc. Examples of sores are bed sores, canker sores, chrome sores, cold sores, pressure sores etc. Examples of ulcers are, e.g., peptic ulcer, duodenal ulcer, gastric ulcer, gouty ulcer, diabetic ulcer, hypertensive ischemic ulcer, stasis ulcer, ulcus cruris (venous ulcer), sublingual ulcer, submucous ulcer, symptomatic ulcer, trophic ulcer, tropical ulcer, veneral ulcer, e.g. caused by gonorrhoea (including urethritis, endocervicitis and proctitis). Conditions related to wounds or sores which may be successfully treated according to the invention are burns, anthrax, tetanus, gas gangrene, scalatina, erysipelas, sycosis barbae, folliculitis, impetigo contagiosa, or impetigo bullosa, etc. There is often a certain overlap between the use of the terms "wound" and "ulcer" and "wound" and "sore" and, furthermore, the terms are often used at random. Therefore as mentioned above, in the present context the term "wounds" encompasses the term "ulcer", "lesion", "sore" and "infarction", and the terms are indiscriminately used unless otherwise indicated.

The kinds of wounds to be treated according to the invention include also i) general wounds such as, e.g., surgical, traumatic, infectious, ischemic, thermal, chemical and bullous wounds; ii) wounds specific for the oral cavity such as, e.g., post-extraction wounds, endodontic wounds especially in connection with treatment of cysts and abscesses, ulcers and lesions of bacterial, viral or autoimmunological origin, mechanical, chemical, thermal, infectious and lichenoid wounds; herpes ulcers, stomatitis aphthosa, acute necrotising ulcerative gingivitis and burning mouth syndrome are specific examples; and iii) wounds on the skin such as, e.g., neoplasm, burns (e.g. chemical, thermal), lesions (bacterial, viral, autoimmunological), bites and surgical incisions. Another way of classifying wounds is as i) small tissue loss due to surgical incisions, minor abrasions and minor bites, or as ii) significant tissue loss. The latter group includes ischemic ulcers, pressure sores, fistulae, lacerations, severe bites, thermal burns and donor site wounds (in soft and hard tissues) and infarctions.

In other aspects of the invention, the wound to be prevented and/or treated is selected from the group consisting of aseptic wounds, infarctions, contused wounds, incised wounds, lacerated wounds, non-penetrating wounds, open wounds, penetrating wounds, perforating wounds, puncture wounds, septic wounds and subcutaneous wounds.

Other wounds which are of importance in connection with the present invention are wounds like ischemic ulcers, pressure sores, fistulae, severe bites, thermal burns and donor site wounds.

Ischemic ulcers and pressure sores are wounds, which normally only heal very slowly and especially in such cases an improved and more rapid healing is of course of great importance for the patient. Furthermore, the costs involved in the treatment of patients suffering from such wounds are markedly reduced when the healing is improved and takes place more rapidly.

Donor site wounds are wounds which e.g. occur in connection with removal of hard tissue from one part of the body to another part of the body e.g. in connection with transplantation. The wounds resulting from such operations are very painful and an improved healing is therefore most valuable.

The term "skin" is used in a very broad sense embracing the epidermal layer of the skin and in those cases where the skin surface is more or less injured also the dermal layer of the skin. Apart from the stratum corneum, the epidermal layer of the skin is the outer (epithelial) layer and the deeper connective tissue layer of the skin is called the dermis.

Since the skin is the most exposed part of the body, it is particularly susceptible to various kinds of injuries such as, e.g., ruptures, cuts, abrasions, burns and frostbites or injuries arising from various diseases. Furthermore, much skin is often destroyed in accidents. However, due to the important barrier and physiologic function of the skin, the integrity of the skin is important to the well-being of the individual, and any breach or rupture represents a threat that must be met by the body in order to protect its continued existence.

Apart from injuries on the skin, injuries may also be present in all kinds of tissues (i.e. soft and hard tissues). Injuries on soft tissues including mucosal membranes and/or skin are especially relevant in connection with the present invention.

Healing of a wound on the skin or on a mucosal membrane undergoes a series of stages that results either in repair or regeneration of the skin or mucosal membrane. In recent years, regeneration and repair have been distinguished as the two types of healing that may occur. Regeneration may be defined as a biological process whereby the architecture and function of lost tissue are completely renewed. Repair, on the other hand, is a biological process whereby continuity of disrupted tissue is restored by new tissues which do not replicate the structure and function of the lost ones.

The majority of wounds heal through repair, meaning that the new tissue formed is structurally and chemically unlike the original tissue (scar tissue). In the early stage of the tissue repair, one process which is almost always involved is the formation of a transient connective tissue in the area of tissue injury. This process starts by formation of a new extracellular collagen matrix by fibroblasts. This new extracellular collagen matrix is then the support for a connective tissue during the final healing process. The final healing is, in most tissues, a scar formation containing connective tissue. In tissues which have regenerative properties, such as, e.g., skin and bone, the final healing includes regeneration of the original tissue. This regenerated tissue has frequently also some scar characteristics, e.g. a thickening of a healed bone fracture.

Under normal circumstances, the body provides mechanisms for healing injured skin or mucosa in order to restore the integrity of the skin barrier or the mucosa. The repair process for even minor ruptures or wounds may take a period of time extending from hours and days to weeks. However, in ulceration, the healing can be very slow and the wound may persist for an extended period of time, i.e. months or even years.

Burns are associated with reduced testosterone levels, and hypogonadism is associated with delayed wound healing. In one embodiment, the methods of this invention, provide for treating a subject suffering from a wound or a burn via the administration of a SARD according to this invention. In one embodiment, the SARD promotes resolving of the burn or wound, or in another embodiment, participates in the healing process of a burn or a wound, or in another embodiment, treats a secondary complication of a burn or wound.

In one embodiment, the treatment of burns or wounds further incorporates the use of additional growth factors like epidermal growth factor (EGF), transforming growth factor-α (TGF-α), platelet derived growth factor (PDGF), fibroblast growth factors (FGFs) including acidic fibroblast growth factor (α-FGF) and basic fibroblast growth factor (β-FGF), transforming growth factor-β (TGF-β) and insulin like growth factors (IGF-1 and IGF-2), or any combination thereof, which are promoters of wound healing.

Wound healing may be measured by many procedures known in the art, including wound tensile strength, hydroxyproline or collagen content, procollagen expression, and re-epithelialization. As an example, a SARD as described herein is administered orally or topically, at a dosage of about 0.1-1 mg per day. Therapeutic effectiveness is measured as effectiveness in enhancing wound healing. Enhanced wound healing may be measured by known techniques such as decrease in healing time, increase in collagen density, increase in hydroxyproline, reduction in complications, increase in tensile strength, and increased cellularity of scar tissue.

In one embodiment, the terms "treating" or "treatment" includes preventative as well as disorder remitative treatment. The terms "reducing", "suppressing" and "inhibiting" have their commonly understood meaning of lessening or decreasing, in another embodiment, or delaying, in another embodiment, or reducing, in another embodiment the incidence, severity or pathogenesis of a disease, disorder or condition. In some embodiments, the term treatment refers to delayed progression of, prolonged remission of, reduced incidence of, or amelioration of symptoms associated with the disease, disorder or condition. In one embodiment, the terms "treating" "reducing", "suppressing" or "inhibiting" refer to a reduction in morbidity, mortality, or a combination thereof, in association with the indicated disease, disorder or condition. In one embodiment, the term "progression" refers to an increasing in scope or severity, advancing, growing or becoming worse. The term "recurrence" means, in another embodiment, the return of a disease after a remission. In one embodiment, the methods of treatment of the invention reduce the severity of the disease, or in another embodiment, symptoms associated with the disease, or in another embodiment, reduces the number of biomarkers expressed during disease.

In one embodiment, the term "treating" and its included aspects, refers to the administration to a subject with the indicated disease, disorder or condition, or in some embodiments, to a subject predisposed to the indicated disease, disorder or condition. The term "predisposed to" is to be considered to refer to, inter alia, a genetic profile or familial relationship which is associated with a trend or statistical increase in incidence, severity, etc. of the indicated disease. In some embodiments, the term "predisposed to" is to be considered to refer to inter alia, a lifestyle which is associated with increased risk of the indicated disease. In some embodiments, the term "predisposed to" is to be considered to refer to inter alia, the presence of biomarkers which are associated with the indicated disease, for example, in cancer, the term "predisposed to" the cancer may comprise the presence of precancerous precursors for the indicated cancer.

In some embodiments, the term "reducing the pathogenesis" is to be understood to encompass reducing tissue damage, or organ damage associated with a particular disease, disorder or condition. In another embodiment, the term "reducing the pathogenesis" is to be understood to encompass reducing the incidence or severity of an associated disease, disorder or condition, with that in question. In another embodiment, the term "reducing the pathogenesis" is to be understood to encompass reducing the number of associated diseases, disorders or conditions with the indicated, or symptoms associated thereto.

Pharmaceutical Compositions

In some embodiments, this invention provides methods of use which comprise administering a composition comprising the described compounds. As used herein, "pharmaceutical composition" means a "therapeutically effective amount" of the active ingredient, i.e. the compound of this invention, together with a pharmaceutically acceptable carrier or diluent. A "therapeutically effective amount" as used herein refers to that amount which provides a therapeutic effect for a given condition and administration regimen.

As used herein, the term "administering" refers to bringing a subject in contact with a compound of the present invention. As used herein, administration can be accomplished in vitro, i.e. in a test tube, or in vivo, i.e. in cells or tissues of living organisms, for example humans. In one embodiment, the present invention encompasses administering the compounds of the present invention to a male subject. In one embodiment, the present invention encompasses administering the compounds of the present invention to a female subject.

This invention provides, in other embodiments, pharmaceutical products of the compounds described herein. The term "pharmaceutical product" refers, in other embodiments, to a composition suitable for pharmaceutical use (pharmaceutical composition), for example, as described herein.

The compounds of the invention can be administered alone or as an active ingredient of a formulation. Thus, the present invention also includes pharmaceutical compositions of compounds of formulas I-VII, containing, for example, one or more pharmaceutically acceptable carriers.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

The mode of administration and dosage form are closely related to the therapeutic amounts of the compounds or compositions which are desirable and efficacious for the given treatment application.

The pharmaceutical compositions containing a compound of this invention can be administered to a subject by any method known to a person skilled in the art, such as orally, parenterally, intravascularly, paracancerally, transmucosally, transdermally, intramuscularly, intranasally, intravenously, intradermally, subcutaneously, sublingually, intraperitoneally, intraventricularly, intracranially, intravaginally, by inhalation, rectally, intratumorally, or by any means in which the composition can be delivered to tissue (e.g., needle or catheter). Alternatively, topical administration may be desired for application to dermal, ocular, or mucosal surfaces. Another method of administration is via aspiration or aerosol formulation. Further, in another embodiment, the pharmaceutical compositions may be administered topically to body surfaces, and are thus formulated in a form suitable for topical administration. Suitable topical formulations include gels, ointments, creams, lotions, drops and the like. For topical administrations, the compounds of this invention or their physiologically tolerated derivatives such as salts, esters, N-oxides, and the like are prepared and applied as solutions, suspensions, or emulsions in a physiologically acceptable diluent with or without a pharmaceutical carrier.

Suitable dosage forms include but are not limited to oral, rectal, sub-lingual, mucosal, nasal, ophthalmic, subcutaneous, intramuscular, intravenous, transdermal, spinal, intrathecal, intra-articular, intra-arterial, sub-arachinoid, bronchial, lymphatic, and intra-uterile administration, and other dosage forms for systemic delivery of active ingredients. In some embodiments, formulations suitable for oral administration are preferred. In some applications, formulations suitable for topical administration are preferred.

Topical Administration:

In a typical embodiment, the compounds of formulas I-VII are administered topically. Topical administration is especially appropriate for hirsutism, alopecia, acne and excess sebum. The dose will vary, but as a general guideline, the compound will be present in a dermatologically acceptable carrier in an amount of from about 0.01 to 50 w/w %, and more typically from about 0.1 to 10 w/w %. Typically, the dermatological preparation will be applied to the affected area from 1 to 4 times daily. "Dermatologically acceptable" refers to a carrier which may be applied to the skin or hair, and which will allows the drug to diffuse to the site of action. More specifically, it refers to a site where inhibition of androgen receptor or degradation of androgen receptor is desired.

In a further embodiment, the compounds of formulas I-VII are used topically to relieve alopecia, especially androgenic alopecia. Androgens have a profound effect on both hair growth and hair loss. In most body sites, such as the beard and pubic skin, androgens stimulate hair growth by prolonging the growth phase of the hair cycle (anagen) and increasing follicle size. Hair growth on the scalp does not require androgens but, paradoxically, androgens are necessary for the balding on the scalp in genetically predisposed individuals (androgenic alopecia) where there is a progressive decline in the duration of anagen and in hair follicle size. Androgenic alopecia is also common in women where it usually presents as a diffuse hair loss rather than showing the patterning seen in men.

While the compounds of formulas I-VII will most typically be used to alleviate androgenic alopecia, the invention is not limited to this specific condition. The compounds of formulas I-VII may be used to alleviate any type of alopecia. Examples of non-androgenic alopecia include alopecia areata, alopecia due to radiotherapy or chemotherapy, scarring alopecia, stress related alopecia, etc. As used in this application "alopecia" refers to partial or complete hair loss on the scalp.

Thus, the compounds of formulas I-VII can be applied topically to the scalp and hair to prevent, or alleviate balding. Further, the compound of formulas I-VII can be applied topically in order to induce or promote the growth or regrowth of hair on the scalp.

In a further embodiment of the invention, a compound of formulas I-VII is applied topically in order to prevent the growth of hair in areas where such hair growth in not desired. One such use will be to alleviate hirsutism. Hirsutism is excessive hair growth in areas that typically do not have hair (i.e., a female face). Such inappropriate hair growth occurs most commonly in women and is frequently seen at menopause. The topical administration of the compounds of formulas I-VII will alleviate this condition leading to a reduction, or elimination of this inappropriate, or undesired, hair growth.

The compounds of formulas I-VII may also be used topically to decrease sebum production. Sebum is composed of triglycerides, wax esters, fatty acids, sterol esters and squalene. Sebum is produced in the acinar cells of the sebaceous glands and accumulates as these cells age. At maturation, the acinar cells lyse, releasing sebum into the luminal duct so that it may be deposited on the surface of the skin.

In some individuals, an excessive quantity of sebum is secreted onto the skin. This can have a number of adverse consequences. It can exacerbate acne, since sebum is the primary food source for *Propionbacterium acnes*, the causative agent of acne. It can cause the skin to have a greasy appearance, typically considered cosmetically unappealing.

Formation of sebum is regulated by growth factors and a variety of hormones including androgens. The cellular and molecular mechanism by which androgens exert their influence on the sebaceous gland has not been fully elucidated. However, clinical experience documents the impact androgens have on sebum production. Sebum production is significantly increased during puberty, when androgen levels are their highest. Thus the compounds of formulas I-VII inhibit the secretion of sebum and thus reduce the amount of sebum on the surface of the skin. The compounds of formulas I-VII can be used to treat a variety of dermal diseases such as acne or seborrheic dermatitis.

In addition to treating diseases associated with excess sebum production, the compounds of formulas I-VII can also be used to achieve a cosmetic effect. Some consumers believe that they are afflicted with overactive sebaceous glands. They feel that their skin is oily and thus unattractive. These individuals can utilize the compounds of formulas I-VII to decrease the amount of sebum on their skin. Decreasing the secretion of sebum will alleviate oily skin in individuals afflicted with such conditions.

The compounds of formulas I-VII of this invention will typically be administered topically. As used herein, topical refers to application of the compounds of formulas I-VII (and optional carrier) directly to the skin and/or hair. The topical composition according to the present invention can be in the form of solutions, lotions, salves, creams, ointments, liposomes, sprays, gels, foams, roller sticks, and any other formulation routinely used in dermatology.

Thus, a further embodiment relates to cosmetic or pharmaceutical compositions, in particular dermatological compositions, which comprise at least one of the compounds corresponding to formulas I-VII above. Such dermatological compositions will contain from 0.001% to 10% w/w % of the compounds in admixture with a dermatologically acceptable carrier, and more typically, from 0.1 to 5 w/w % of the compounds. Such compositions will typically be applied from 1 to 4 times daily. The reader's attention is directed to Remington's Pharmaceutical Science, Edition 17, Mark Publishing Co., Easton, Pa. for a discussion of how to prepare such formulations.

The compositions according to the invention can also consist of solid preparations constituting cleansing soaps or bars. These compositions are prepared according to the usual methods.

The compounds of formulas I-VII can also be used for the hair in the form of aqueous, alcoholic or aqueous-alcoholic solutions, or in the form of creams, gels, emulsions or mousses, or alternatively in the form of aerosol compositions also comprising a propellant under pressure. The composition according to the invention can also be a hair care composition, and in particular a shampoo, a hair-setting lotion, a treating lotion, a styling cream or gel, a dye composition, a lotion or gel for preventing hair loss, etc. The amounts of the various constituents in the dermatological compositions according to the invention are those conventionally used in the fields considered.

The medicinal and cosmetics containing the compounds of formulas I-VII will typically be packaged for retail distribution (i.e., an article of manufacture). Such articles will be labeled and packaged in a manner to instruct the patient how to use the product. Such instructions will include the condition to be treated, duration of treatment, dosing schedule, etc.

Antiandrogens, such as finasteride or flutamide, have been shown to decrease androgen levels or block androgen action in the skin to some extent but suffer from undesirable systemic effects. An alternative approach is to topically apply a selective androgen receptor degrader (SARD) compound to the affected areas. In one embodiment, such a SARD compound would exhibit potent but local inhibition of AR activity. In another embodiment, the SARD compound would exhibit potent but local degradation of AR activity. In another embodiment, the SARD compound would not penetrate to the systemic circulation of the subject. In another embodiment, the SARD compound would be rapidly metabolized upon entry into the blood, limiting systemic exposure.

To prepare such pharmaceutical dosage forms, the active ingredient may be mixed with a pharmaceutical carrier according to conventional pharmaceutical compounding techniques. The carrier may take a wide variety of forms depending on the form of preparation desired for administration.

As used herein "pharmaceutically acceptable carriers or diluents" are well known to those skilled in the art. The carrier or diluent may be a solid carrier or diluent for solid formulations, a liquid carrier or diluent for liquid formulations, or mixtures thereof.

Solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

Oral Administration and Parenteral:

In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like. For solid oral preparations such as, for example, powders, capsules and tablets, suitable carriers and additives include starches, sugars, diluents, granulating agents, lubricants, binders, disintegrating agents and the like. Due to their ease in administration, tablets and capsules represent the most advantageous oral dosage unit form. If desired, tablets may be sugar coated or enteric coated by standard techniques.

For parenteral formulations, the carrier will usually comprise sterile water, though other ingredients, for example, ingredients that aid solubility or for preservation, may be included. Injectable solutions may also be prepared in which case appropriate stabilizing agents may be employed.

In some applications, it may be advantageous to utilize the active agent in a "vectorized" form, such as by encapsulation of the active agent in a liposome or other encapsulant medium, or by fixation of the active agent, e.g., by covalent bonding, chelation, or associative coordination, on a suitable biomolecule, such as those selected from proteins, lipoproteins, glycoproteins, and polysaccharides.

Treatment methods of the present invention using formulations suitable for oral administration may be presented as discrete units such as capsules, cachets, tablets, or lozenges, each containing a predetermined amount of the active ingredient as, for example, a powder or granules. Optionally, a suspension in an aqueous liquor or a non-aqueous liquid may be employed, such as a syrup, an elixir, an emulsion, or a draught.

A tablet may be made by compression or molding, or wet granulation, optionally with one or more accessory ingredients. Compressed tablets may be prepared by compressing in a suitable machine, with the active compound being in a free-flowing form such as a powder or granules which optionally is mixed with, for example, a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration may comprise a sterile aqueous preparation of the active compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Parenteral administration may comprise any suitable form of systemic delivery. Administration may for example be intravenous, intra-arterial, intrathecal, intramuscular, subcutaneous, intramuscular, intra-abdominal (e.g., intraperitoneal), etc., and may be effected by infusion pumps (external or implantable) or any other suitable means appropriate to the desired administration modality.

Nasal and other mucosal spray formulations (e.g. inhalable forms) can comprise purified aqueous solutions of the active compounds with preservative agents and isotonic agents. Such formulations are preferably adjusted to a pH and isotonic state compatible with the nasal or other mucous membranes. Alternatively, they can be in the form of finely divided solid powders suspended in a gas carrier. Such formulations may be delivered by any suitable means or method, e.g., by nebulizer, atomizer, metered dose inhaler, or the like.

Formulations for rectal administration may be presented as a suppository with a suitable carrier such as cocoa butter, hydrogenated fats, or hydrogenated fatty carboxylic acids.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations of this invention may further include one or more accessory ingredient(s) selected from, for example, diluents, buffers, flavoring agents, binders, disintegrants, surface active agents, thickeners, lubricants, preservatives (including antioxidants), and the like.

The formulations of the present invention can have immediate release, sustained release, delayed-onset release or any other release profile known to one skilled in the art.

It is to be understood that this invention encompasses any embodiment of a compound as described herein, which in some embodiments is referred to as "a compound of this invention".

For administration to mammals, and particularly humans, it is expected that the physician will determine the actual dosage and duration of treatment, which will be most suitable for an individual and can vary with the age, weight and response of the particular individual.

In one embodiment, the methods of this invention may comprise administration of a compound of this invention at various dosages. In one embodiment, a compound of this invention is administered at a dosage of 1-3000 mg per day. In additional embodiments, a compound of this invention is administered at a dose of 1-10 mg per day, 3-26 mg per day, 3-60 mg per day, 3-16 mg per day, 3-30 mg per day, 10-26 mg per day, 15-60 mg, 50-100 mg per day, 50-200 mg per day, 100-250 mg per day, 125-300 mg per day, 20-50 mg per day, 5-50 mg per day, 200-500 mg per day, 125-500 mg per day, 500-1000 mg per day, 200-1000 mg per day, 1000-2000 mg per day, 1000-3000 mg per day, 125-3000 mg per day, 2000-3000 mg per day, 300-1500 mg per day or 100-1000 mg per day. In one embodiment, a compound of this invention is administered at a dosage of 25 mg per day. In one embodiment, a compound of this invention is administered at a dosage of 40 mg per day. In one embodiment, a compound of this invention is administered at a dosage of 50 mg per day. In one embodiment, a compound of this invention is administered at a dosage of 67.5 mg per day. In one embodiment, a compound of this invention is administered at a dosage of 75 mg per day. In one embodiment, a compound of this invention is administered at a dosage of 80 mg per day. In one embodiment, a compound of this invention is administered at a dosage of 100 mg per day. In one embodiment, a compound of this invention is administered at a dosage of 125 mg per day. In one embodiment, a compound of this invention is administered at a dosage of 250 mg per day. In one embodiment, a compound of this invention is administered at a dosage of 300 mg per day. In one embodiment, a compound of this invention is administered at a dosage of 500 mg per day. In one embodiment, a compound of this invention is administered at a dosage of 600 mg per day. In one embodiment, a compound of this invention is administered at a dosage of 1000 mg per day. In one embodiment, a compound of this invention is administered at a dosage of 1500 mg per day. In one embodiment, a compound of this invention is administered at a dosage of 2000 mg per day. In one embodiment, a compound of this invention is administered at a dosage of 2500 mg per day. In one embodiment, a compound of this invention is administered at a dosage of 3000 mg per day. In another embodiment, the compound is any one of compounds 13-21, 49, 50 and 17a.

In one embodiment, the methods of this invention may comprise administration of a compound of this invention at various dosages. In one embodiment, a compound of this invention is administered at a dosage of 3 mg. In additional embodiments, a compound of this invention is administered at a dosage of 10 mg, 30 mg, 40 mg, 50 mg, 80 mg, 100 mg, 120 mg, 125 mg, 200 mg, 250 mg, 300 mg, 450 mg, 500 mg, 600 mg, 900 mg, 1000 mg, 1500 mg, 2000 mg, 2500 mg or 3000 mg. In another embodiment, the compound is any one of compounds 13-21, 49, 50 and 17a.

In one embodiment, the methods of this invention may comprise administration of a compound of this invention at various dosages. In one embodiment, a compound of this invention is administered at a dosage of 0.1 mg/kg/day. In additional embodiments, a compound of this invention is administered at a dosage between 0.2 to 30 mg/kg/day, or 0.2 mg/kg/day, 0.3 mg/kg/day, 1 mg/kg/day, 3 mg/kg/day, 5 mg/kg/day, 10 mg/kg/day, 20 mg/kg/day, 30 mg/kg/day, 50 mg/kg/day or 100 mg/kg/day.

In one embodiment, the methods of this invention provide for the use of a pharmaceutical composition comprising a compound of formulas I-VII. In additional embodiments, the methods of this invention are provided for use of a pharmaceutical composition comprising a compound of formula I, formula II, formula III, formula IV, or formula V, formula VI, or formula VII, or any one of compounds 13-21, 49, 50 and 17a.

In certain embodiment, the pharmaceutical composition is a solid dosage form. In another embodiment, the pharmaceutical composition is a tablet. In another embodiment, the pharmaceutical composition is a capsule. In another embodiment, the pharmaceutical composition is a solution. In another embodiment, the pharmaceutical composition is a transdermal patch.

In one embodiment, use of a compound of this invention or a composition comprising the same, will have utility in inhibiting, suppressing, enhancing or stimulating a desired response in a subject, as will be understood by one skilled in the art. In another embodiment, the compositions may further comprise additional active ingredients, whose activity is useful for the particular application for which the compound of this invention is being administered.

For administration to mammals, and particularly humans, it is expected that the physician will determine the actual dosage and duration of treatment, which will be most suitable for an individual and can vary with the age, weight, genetics and/or response of the particular individual.

In some embodiments, any of the compositions of this invention will comprise a compound of this invention, in any form or embodiment as described herein. In some embodiments, any of the compositions of this invention will consist of a compound of this invention, in any form or embodiment as described herein. In some embodiments, of the compositions of this invention will consist essentially of a compound of this invention, in any form or embodiment as described herein. In some embodiments, the term "comprise" refers to the inclusion of the indicated active agent, such as the compound of this invention, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" may refer to components which facilitate the release of the active ingredient. In some embodiments, the term "consisting" refers to a composition, which contains the active ingredient and a pharmaceutically acceptable carrier or excipient.

It is to be understood that any use of any of the compounds as herein described may be used in the treatment of any disease, disorder or condition as described herein, and represents an embodiment of this invention. In one embodiment, the compounds are a free base, free acid, non charged or non-complexed compound.

The following examples are presented in order to more fully illustrate the preferred embodiments of the invention. They should in no way, however, be construed as limiting the broad scope of the invention.

EXAMPLES

Example 1

Synthesis of (S)-3-(Substituted phenyl amino)-N-(4-nitro- or 4-cyano-3-(trifluoromethyl) phenyl)-2-hydroxy-2-methylpropanamides (Compounds 12-19)

Scheme 1. Synthesis of (S)-3-(substituted phenyl amino)-N-(4-nitro- or 4-cyano-3-(trifluoromethyl)phenyl)-2-hydroxy-2-methylpropanamides (12~19).

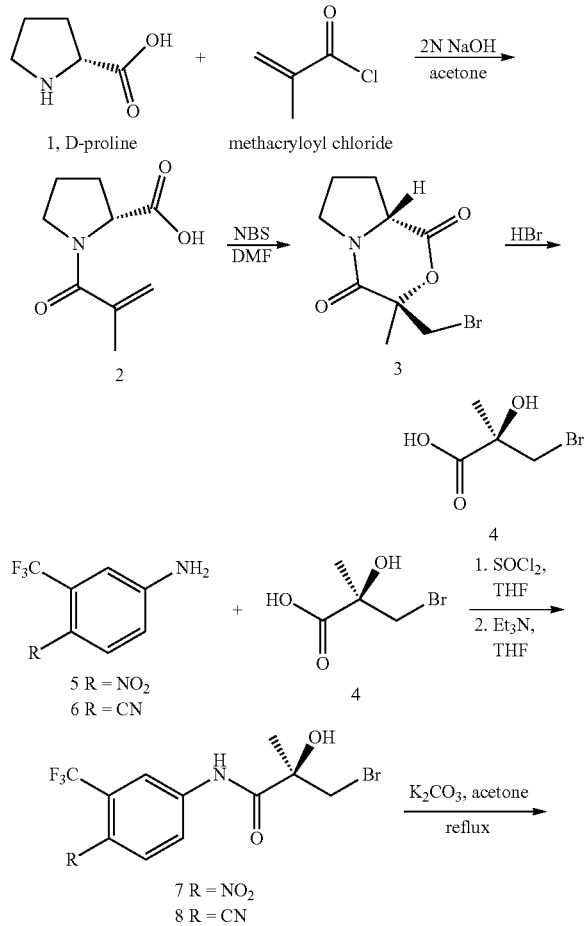

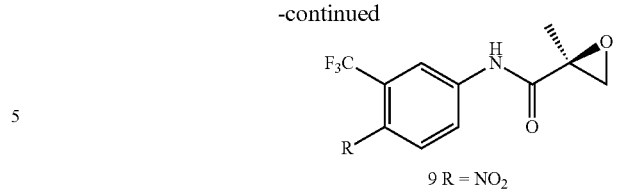

9 R = $NO_2$
10 R = CN

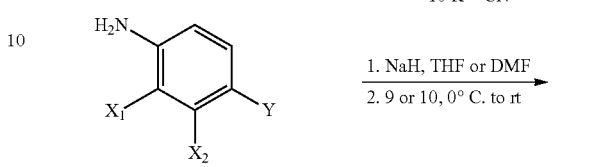

1. NaH, THF or DMF
2. 9 or 10, 0° C. to rt

11
$X_1$ or/and $X_2$ = H, Ph, 4-fluorophenyl-
Y = H, CN

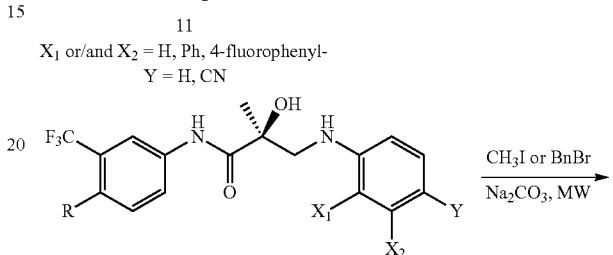

CH$_3$I or BnBr
Na$_2$CO$_3$, MW

12 R = CN, $X_1$ = H, $X_2$ = H, Y = CN
13 R = CN, $X_1$ = $X_2$ = Ph, Y = CN
14 R = CN, $X_1$ = H, $X_2$ = Ph, Y = CN
15 R = CN, $X_1$ = Ph, $X_2$ = H, Y = CN
16 R = CN, $X_1$ = H, $X_2$ = 4-fluorophenyl, Y = CN

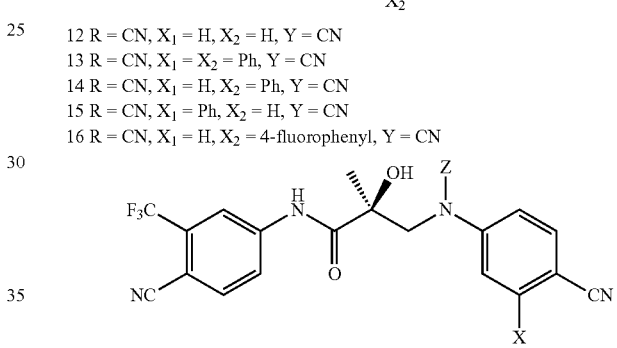

17 ~ 19
X = H, Ph, 4-fluorophenyl-
Z = CH$_3$, Bn (2R)-1-Methacryloylpyrrolidin-2-carboxylic acid (2)

D-Proline (14.93 g, 0.13 mol) was dissolved in 71 mL of 2 N NaOH and cooled in an ice bath. The resulting alkaline solution was diluted with acetone (71 mL). An acetone solution (71 mL) of methacryloyl chloride (13.56 g, 0.13 mol) and 2 N NaOH solution (71 mL) were simultaneously added over 40 min to the aqueous solution of D-proline in an ice bath. The temperature of the mixture was kept at 10-11° C. during the addition of the methacryloyl chloride. After stirring (3 h, room temperature (RT)), the mixture was evaporated in vacuo at a temperature at 35-45° C. to remove acetone. The resulting solution was washed with ethyl ether and was acidified to pH 2 with concentrated HCl. The acidic mixture was saturated with NaCl and was extracted with EtOAc (100 mL×3). The combined extracts were dried over Na$_2$SO$_4$, filtered through Celite®, and evaporated in vacuo to give the crude product as a colorless oil. Recrystallization of the oil from ethyl ether and hexanes afforded 16.2 g (68%) of the desired compound as colorless crystals: mp 102.1-103.4° C. (lit. mp 102.5-103.5° C.); the NMR spectrum of this compound demonstrated the existence of two rotamers of the title compound.

$^1$H NMR (300 MHz, DMSO-d$_6$) δ 5.28 (s) and 5.15 (s) for the first rotamer, 5.15 (s) and 5.03 (s) for the second rotamer (totally 2H for both rotamers, vinyl CH$_2$), 4.48-4.44 for the first rotamer, 4.24-4.20 (m) for the second rotamer (totally 1H for both rotamers, CH at the chiral center), 3.57-3.38 (m, 2H, CH$_2$), 2.27-2.12 (1H, CH), 1.97-1.72 (m, 6H, CH$_2$, CH, Me); 13C NMR (75 MHz, DMSO-d$_6$) δ for major rotamer 173.3, 169.1, 140.9, 116.4, 58.3, 48.7, 28.9, 24.7, 19.5: for minor rotamer 174.0, 170.0, 141.6, 115.2, 60.3, 45.9, 31.0, 22.3, 19.7; IR (KBr) 3437 (OH), 1737 (C=O), 1647 (CO, COOH), 1584, 1508, 1459, 1369, 1348, 1178 cm$^{-1}$; [α]$_D^{26}$+80.8° (c=1, MeOH); Anal. Calcd. for C$_9$H$_{13}$NO$_3$: C, 59.00; H, 7.15; N, 7.65. Found: C, 59.13; H, 7.19; N, 7.61.

(3R,8aR)-3-Bromomethyl-3-methyl-tetrahydro-pyrrolo[2,1-c][1,4]oxazine-1,4-dione (3)

A solution of NBS (23.5 g, 0.132 mol) in 100 mL of DMF was added dropwise to a stirred solution of the (methylacryloyl)-pyrrolidine (16.1 g, 88 mmol) in 70 mL of DMF under argon at RT, and the resulting mixture was stirred 3 days. The solvent was removed in vacuo, and a yellow solid was precipitated. The solid was suspended in water, stirred overnight at RT, filtered, and dried to give 18.6 g (81%) (smaller weight when dried ~34%) of the title compound as a yellow solid: mp 158.1-160.3° C.;

$^1$H NMR (300 MHz, DMSO-d$_6$) δ 4.69 (dd, J=9.6 Hz, J=6.7 Hz, 1H, CH at the chiral center), 4.02 (d, J=11.4 Hz, 1H, CHH$_a$), 3.86 (d, J=11.4 Hz, 1H, CHH$_b$), 3.53-3.24 (m, 4H, CH$_2$), 2.30-2.20 (m, 1H, CH), 2.04-1.72 (m, 3H, CH$_2$ and CH), 1.56 (s, 2H, Me); 13C NMR (75 MHz, DMSO-d$_6$) δ 167.3, 163.1, 83.9, 57.2, 45.4, 37.8, 29.0, 22.9, 21.6; IR (KBr) 3474, 1745 (C=O), 1687 (C=O), 1448, 1377, 1360, 1308, 1227, 1159, 1062 cm$^{-1}$; [α]$_D^{26}$+124.5° (c=1.3, chloroform); Anal. Calcd. for C$_9$H$_{12}$BrNO$_3$: C, 41.24; H, 4.61; N, 5.34. Found: C, 41.46; H, 4.64; N, 5.32.

(2R)-3-Bromo-2-hydroxy-2-methylpropanoic acid (4)

A mixture of bromolactone (18.5 g, 71 mmol) in 300 mL of 24% HBr was heated at reflux for 1 h. The resulting solution was diluted with brine (200 mL), and was extracted with ethyl acetate (100 mL×4). The combined extracts were washed with saturated NaHCO$_3$ (100 mL×4). The aqueous solution was acidified with concentrated HCl to pH=1, which, in turn, was extracted with ethyl acetate (100 mL×4). The combined organic solution was dried over Na$_2$SO$_4$, filtered through Celite®, and evaporated in vacuo to dryness. Recrystallization from toluene afforded 10.2 g (86%) of the desired compound as colorless crystals: mp 110.3-113.8° C.;

$^1$H NMR (300 MHz, DMSO-d$_6$) δ 3.63 (d, J=10.1 Hz, 1H, CHH$_a$), 3.52 (d, J=10.1 Hz, 1H, CHH$_b$), 1.35 (s, 3H, Me); IR (KBr) 3434 (OH), 3300-2500 (COOH), 1730 (C=O), 1449, 1421, 1380, 1292, 1193, 1085 cm$^{-1}$; [α]$_D^{26}$+10.5° (c=2.6, MeOH); Anal. Calcd. for C$_4$H$_7$BrO$_3$: C, 26.25; H, 3.86. Found: C, 26.28; H, 3.75.

(2R)-3-Bromo-N-[4-cyano-3-(trifluoromethyl)phenyl]-2-hydroxy-2-methylpropanamide (8)

Thionyl chloride (46.02 g, 0.39 mol) was added dropwise to a cooled solution (less than 4° C.) of (R)-3-bromo-2-hydroxy-2-methylpropanoic acid (51.13 g, 0.28 mol) in 300 mL of THF under an argon atmosphere. The resulting mixture was stirred for 3 h under the same condition. To this was added Et$_3$N (39.14 g, 0.39 mol) and stirred for 20 min under the same condition. After 20 min, 5-amino-2-cyanobenzotrifluoride (40.0 g, 0.21 mol), 400 mL of THF were added and then the mixture was allowed to stir overnight at RT. The solvent was removed under reduced pressure to give a solid which was treated with 300 mL of H$_2$O, extracted with EtOAc (2×400 mL). The combined organic extracts were washed with saturated NaHCO$_3$ solution (2×300 mL) and brine (300 mL). The organic layer was dried over MgSO$_4$ and concentrated under reduced pressure to give a solid which was purified from column chromatography using CH$_2$Cl$_2$/EtOAc (80:20) to give a solid. This solid was recrystallized from CH$_2$Cl$_2$/hexane to give 55.8 g (73.9%) of (2R)-3-bromo-N-[4-cyano-3-(trifluoromethyl)phenyl]-2-hydroxy-2-methylpropanamide as a light-yellow solid. Mp 134.0-136.5° C.;

$^1$H NMR (CDCl$_3$/TMS) δ 1.66 (s, 3H, CH$_3$), 3.11 (s, 1H, OH), 3.63 (d, J=10.8 Hz, 1H, CH$_2$), 4.05 (d, J=10.8 Hz, 1H, CH$_2$), 7.85 (d, J=8.4 Hz, 1H, ArH), 7.99 (dd, J=2.1, 8.4 Hz, 1H, ArH), 8.12 (d, J=2.1 Hz, 1H, ArH), 9.04 (bs, 1H, NH). MS (ESI) 349.0 [M-H]$^-$; M.p.: 124-126° C.

Preparation of 4-Cyano 2,3-Substituted Anilines (26-28)

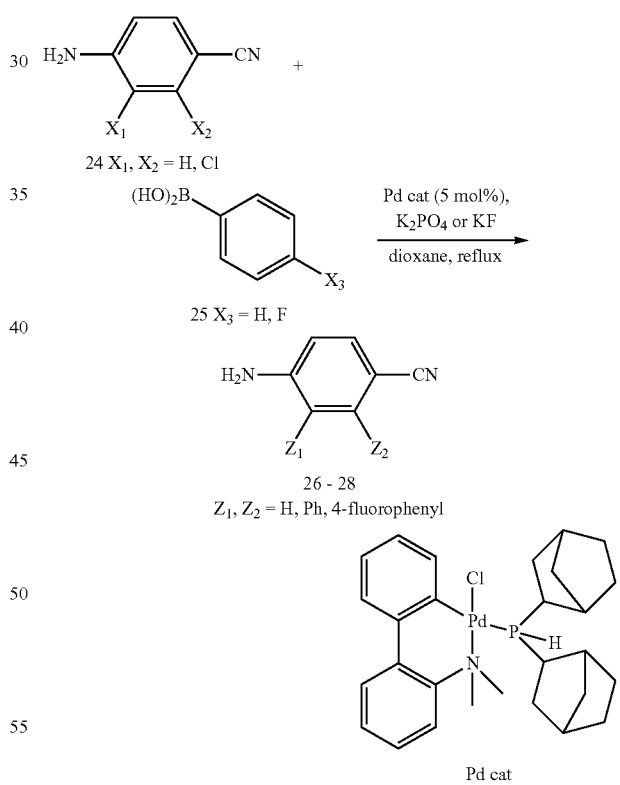

Scheme 2. Preparation of 4-cyano 2,3-substituted anilines (26-28).

General Procedure I:

Arylaniline 24 (4.46 mmol), boric acid 25 (4.46 mmol), Pd cat (0.224 mmol, the structure as shown in Scheme 2) and K$_2$PO$_4$ (8.92 mmol) in 10 mL of 1,4-dioxane were heated to reflux under argon overnight. The mixture was cooled to RT and poured into DCM, which was washed with water, dried over anhydrous MgSO$_4$, and evaporated to dryness. The mixture was purified with flash column chromatography as an eluent EtOAc/hexane and then the condensed compounds were then recrystallized at EtOAc/hexane to give a target products (26~28).

5-Amino-[1,1'-biphenyl]-2-carbonitrile (26)

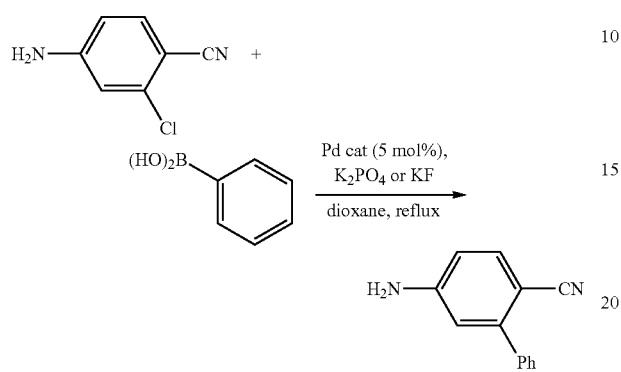

Yield 80%; Brown solid; MS (ESI) 192.8 [M-H]⁻; 217.1 [M+Na]⁺; ¹H NMR (CDCl₃, 400 MHz) δ 7.54-7.42 (m, 6H), 6.71 (d, J=3.2 Hz, 1H), 6.66 (dd, J=11.2, 3.2 Hz, 1H), 4.22 (bs, 2H, NH₂).

6-Amino-[1,1'-biphenyl]-3-carbonitrile (27)

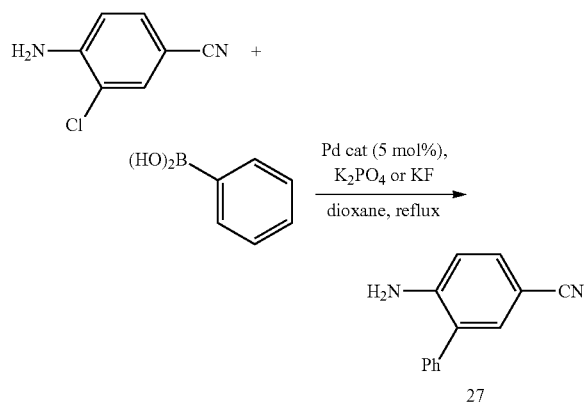

Yield 79%; Brown solid; MS (ESI) 192.8 [M-H]⁻; 217.1 [M+Na]⁺; ¹H NMR (CDCl₃, 400 MHz) δ 7.50-7.30 (m, 7H), 6.76 (dd, J=11.2, 6.0 Hz, 1H), 4.27 (bs, 2H, NH₂).

5-Amino-4'-fluoro-[1,1'-biphenyl]-2-carbonitrile (28)

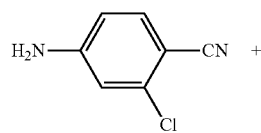

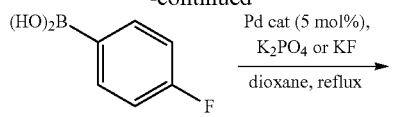

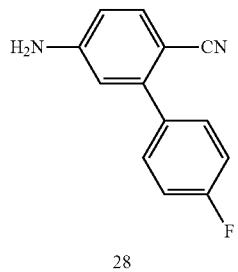

Yield 98%; Brown solid; MS (ESI) 200.8 [M-H]⁻; ¹H NMR (DMSO-d₆, 400 MHz) δ 7.50-7.48 (m, 3H), 7.34-7.30 (m, 2H), 6.63 (m, 2H), 6.26 (bs, 2H, NH₂).

Preparation of several 2-hydroxy-2-methylpropanamides (12-19)

General Procedure II:

Step 1.

Preparation of (S)—N-(4-cyano-3-(trifluoromethyl)phenyl)-2-methyloxirane-2-carboxamide (10) in THF: a mixture of hydroxylbromide 8 (1.0 g, 2.84 mmol) and potassium carbonate (790 mg, 5.70 mmol) in 60 mL acetone was heated to reflux for 30 min. After complete conversion of starting bromide 8 to desired epoxide 10 as monitored by TLC, the solvent was evaporated under reduced pressure to give yellowish residue, which was poured into 20 mL of anhydrous EtOAc. The solution was filtered through Celite® pad to remove K₂CO₃ residue and condensed under reduced pressure to give a yellowish solid of epoxide 10, which was dissolved in 5 mL of anhydrous THF to prepare a solution of epoxide 10 in THF. The resulting solution was directly used as next reactant without analysis.

Step 2.

NaH of 60% dispersion in mineral oil (228 mg, 5.7 mmol) was added in 30 mL of anhydrous THF solvent in 100 mL dried two necked round bottom flask equipped with a dropping funnel. Substituted aniline 11 (2.84 mmol) was added to the solution under argon atmosphere at ice-water bath, and the resulting solution was stirred for 30 min at the ice-water bath. Into the flask, the prepared solution of epoxide 9 or 10 (2.84 mmol in THF) was added through dropping funnel under argon atmosphere at the ice-water bath and stirred overnight at RT. After adding 1 mL of H₂O, the reaction mixture was condensed under reduced pressure, and then dispersed into 50 mL of EtOAc, washed with 50 mL (×2) water, brine, dried over anhydrous MgSO₄, and evaporated to dryness. The mixture was purified with flash column chromatography with EtOAc/hexane as eluent, and then the condensed compounds were then recrystallized at EtOAc/hexane to give the respective target products 12~19.

Preparation of SARDs 12-19

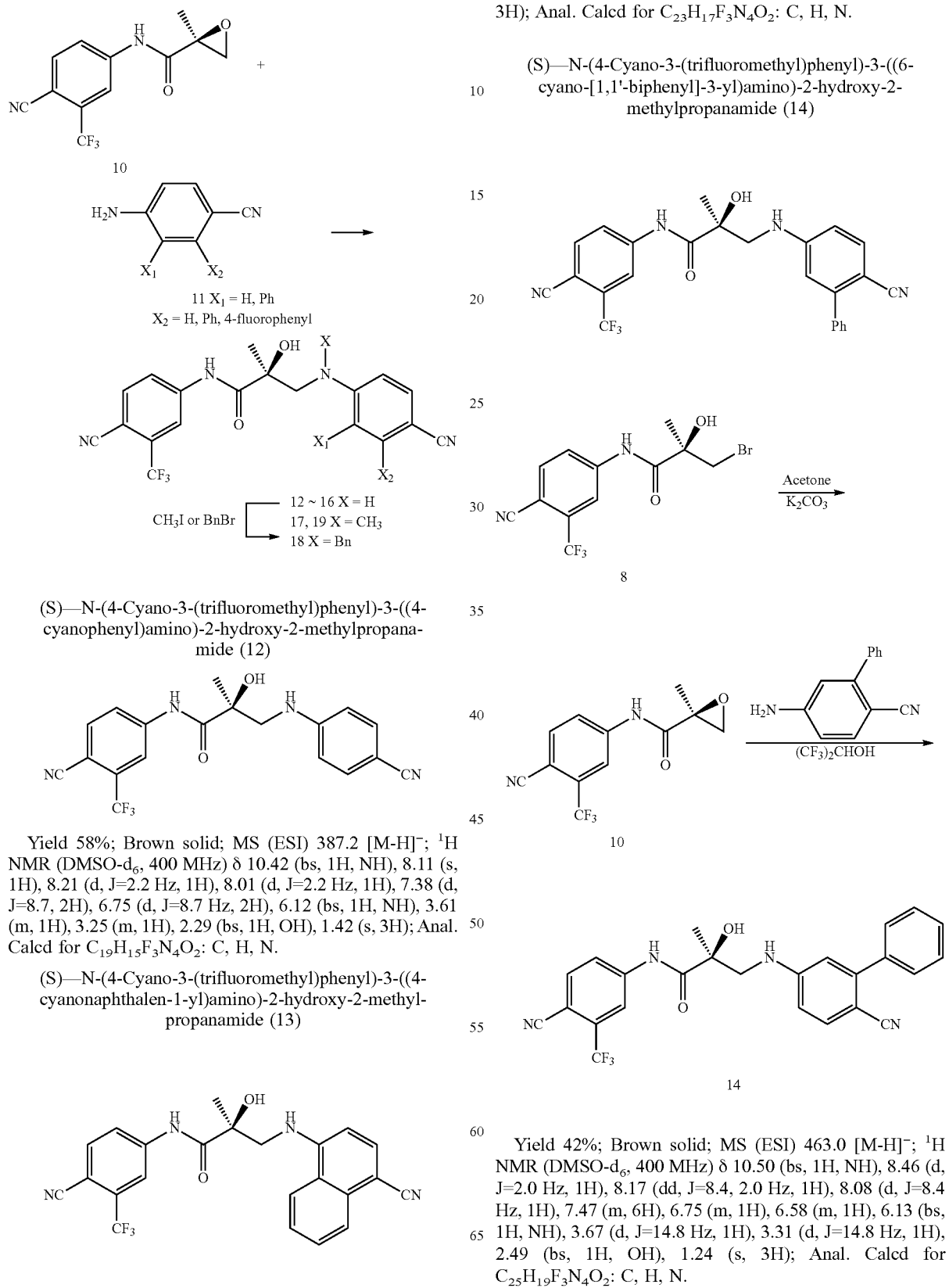

Scheme 3. Preparation of SARDs 12-19.

11 X$_1$ = H, Ph
X$_2$ = H, Ph, 4-fluorophenyl

CH$_3$I or BnBr
12 ~ 16 X = H
17, 19 X = CH$_3$
18 X = Bn (S)—N-(4-Cyano-3-(trifluoromethyl)phenyl)-3-((4-cyanophenyl)amino)-2-hydroxy-2-methylpropanamide (12)

Yield 58%; Brown solid; MS (ESI) 387.2 [M-H]$^-$; $^1$H NMR (DMSO-d$_6$, 400 MHz) δ 10.42 (bs, 1H, NH), 8.11 (s, 1H), 8.21 (d, J=2.2 Hz, 1H), 8.01 (d, J=2.2 Hz, 1H), 7.38 (d, J=8.7 Hz, 2H), 6.75 (d, J=8.7 Hz, 2H), 6.12 (bs, 1H, NH), 3.61 (m, 1H), 3.25 (m, 1H), 2.29 (bs, 1H, OH), 1.42 (s, 3H); Anal. Calcd for C$_{19}$H$_{15}$F$_3$N$_4$O$_2$: C, H, N.

(S)—N-(4-Cyano-3-(trifluoromethyl)phenyl)-3-((4-cyanonaphthalen-1-yl)amino)-2-hydroxy-2-methylpropanamide (13)

Yield 39%; Brown solid; MS (ESI) 437.2 [M-H]$^-$; $^1$H NMR (CDCl$_3$, 400 MHz) δ 9.14 (bs, 1H, NH), 8.15 (d, J=8.3 Hz, 1H), 8.06 (d, J=1.8 Hz, 1H), 7.98 (dd, J=8.3, 1.8 Hz, 1H), 7.82-7.71 (m, 5H), 6.70 (d, J=8.1 Hz, 1H), 5.51 (bs, 1H, NH), 3.95 (m, 1H), 3.57 (m, 1H), 2.29 (bs, 1H, OH), 1.74 (s, 3H); Anal. Calcd for C$_{23}$H$_{17}$F$_3$N$_4$O$_2$: C, H, N.

(S)—N-(4-Cyano-3-(trifluoromethyl)phenyl)-3-((6-cyano-[1,1'-biphenyl]-3-yl)amino)-2-hydroxy-2-methylpropanamide (14)

Yield 42%; Brown solid; MS (ESI) 463.0 [M-H]$^-$; $^1$H NMR (DMSO-d$_6$, 400 MHz) δ 10.50 (bs, 1H, NH), 8.46 (d, J=2.0 Hz, 1H), 8.17 (dd, J=8.4, 2.0 Hz, 1H), 8.08 (d, J=8.4 Hz, 1H), 7.47 (m, 6H), 6.75 (m, 1H), 6.58 (m, 1H), 6.13 (bs, 1H, NH), 3.67 (d, J=14.8 Hz, 1H), 3.31 (d, J=14.8 Hz, 1H), 2.49 (bs, 1H, OH), 1.24 (s, 3H); Anal. Calcd for C$_{25}$H$_{19}$F$_3$N$_4$O$_2$: C, H, N.

(S)—N-(4-Cyano-3-(trifluoromethyl)phenyl)-3-((5-cyano-[1,1'-biphenyl]-2-yl)amino)-2-hydroxy-2-methylpropanamide (15)

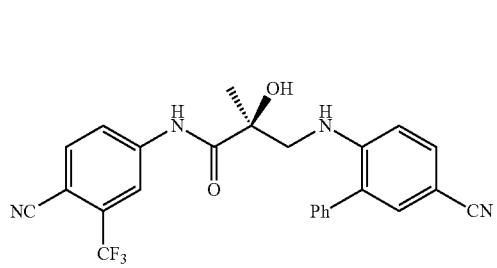 [SMILES: C[C@](O)(CNc1ccc(C#N)cc1-c1ccccc1)C(=O)Nc1ccc(C#N)c(C(F)(F)F)c1]

Yield 32%; Brown solid; MS (ESI) 462.9 [M-H]$^-$; 487.1 [M+Na]$^+$; $^1$H NMR (CDCl$_3$, 400 MHz) δ 10.49 (bs, 1H, NH), 8.45 (m, 1H), 8.17-7.43 (m, 7H), 7.23 (m, 2H), 6.52 (m, 1H), 6.18 (bs, 1H, NH), 3.67 (d, J=14.8 Hz, 1H), 3.31 (d, J=14.8 Hz, 1H), 2.47 (bs, 1H, OH), 1.23 (s, 3H); Anal. Calcd for C$_{25}$H$_{19}$F$_3$N$_4$O$_2$: C, H, N.

Scheme 4. Preparation of SARDs 17-19 and 17a.

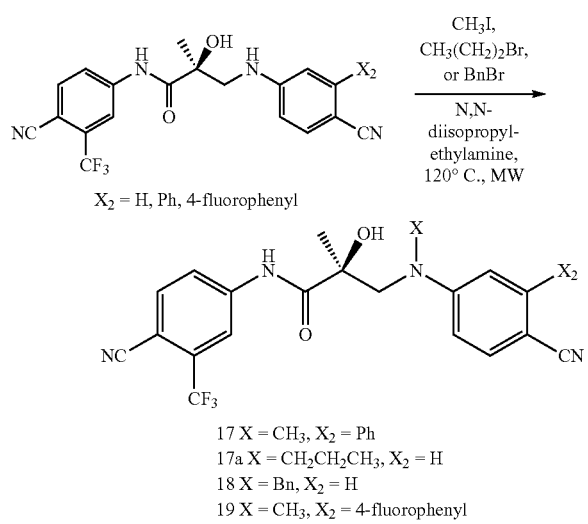

17 X = CH$_3$, X$_2$ = Ph
17a X = CH$_2$CH$_2$CH$_3$, X$_2$ = H
18 X = Bn, X$_2$ = H
19 X = CH$_3$, X$_2$ = 4-fluorophenyl

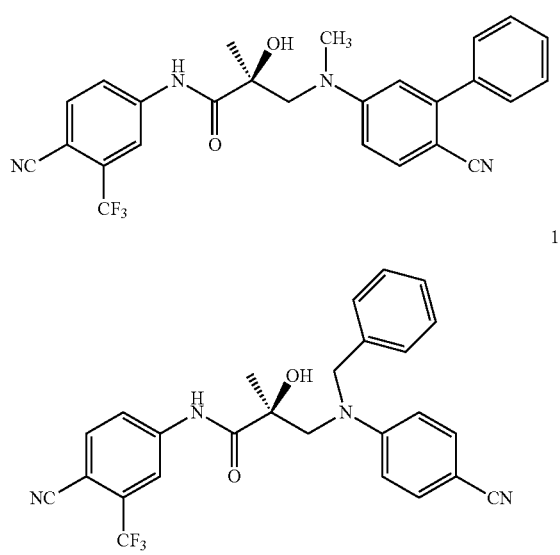

-continued

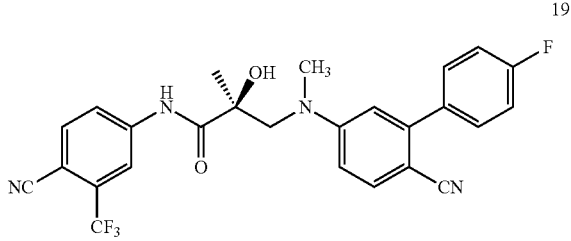

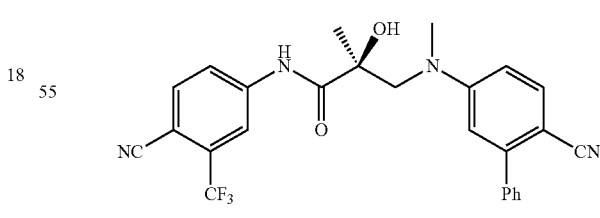

General Procedure III:

A mixture of compounds 12 or 14 (0.15 mmol) and 0.5 mL of alkylhalide (methyl iodide, n-propylbromide or benzyl bromide) with 1 mL of N,N-diisopropylethylamine (DIPEA, Hünig's base) was loaded into a vessel with a cap. The reaction vessels were placed in a reactor block in the microwave. A programmable microwave irradiation cycle of 30 min on (300 W) at 150° C. and 25 min off (fan-cooled) was executed (irradiation time, 30 min). The mixture was transferred to round bottom flask to be concentrated under reduced pressure and poured into EtOAc, which was washed with water and dried over anhydrous MgSO$_4$, concentrated, purified by silica gel chromatography (EtOAc/n-hexane) to afford to desired products (17, 17a, 18 and 19).

(S)—N-(4-Cyano-3-(trifluoromethyl)phenyl)-3-((6-cyano-[1,1'-biphenyl]-3-yl)(methyl)amino)-2-hydroxy-2-methylpropanamide (17)

Yield 42%; Yellowish solid; MS (ESI) 501.1 [M+Na]$^+$; $^1$H NMR (CDCl$_3$, 400 MHz) δ 9.09 (bs, 1H, NH), 8.06 (s, 1H), 7.93 (d, J=2.0 Hz, 1H), 7.90 (d, J=2.0 Hz, 1H), 7.79-7.28 (m, 7H), 6.88 (m, 2H), 3.98 (d, J=15.6 Hz, 1H), 3.75 (d, J=15.6 Hz, 1H), 3.01 (s, 3H), 2.06 (s, 1H, OH), 1.63 (s, 3H); Anal. Calcd for C$_{26}$H$_{21}$F$_3$N$_4$O$_2$: C, H, N.

(S)-3-(Benzyl(4-cyanophenyl)amino)-N-(4-cyano-3-(trifluoromethyl)phenyl)-2-hydroxy-2-methylpropanamide (18)

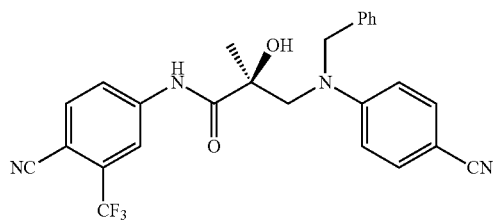 [SMILES: C[C@](O)(CN(Cc1ccccc1)c1ccc(C#N)cc1)C(=O)Nc1ccc(C#N)c(C(F)(F)F)c1]

Yield 32%; Brown solid; MS (ESI) 476.9 [M-H]⁻; 501.1 [M+Na]⁺; ¹H NMR (CDCl₃, 400 MHz) δ 10.22 (bs, 1H, NH), 8.35 (s, 1H), 8.17 (d, J=8.2 Hz, 1H), 8.08 (d, J=8.2 Hz, 1H), 7.20-7.11 (m, 5H), 6.75 (m, 1H), 6.91 (m, 2H), 6.23 (s, 1H), 4.90 (s, 2H), 3.99 (d, J=14.8 Hz, 1H), 3.89 (d, J=14.8 Hz, 1H), 3.42 (bs, 1H, OH), 1.41 (s, 3H); Anal. Calcd for $C_{26}H_{21}F_3N_4O_2$: C, H, N.

(S)—N-(4-Cyano-3-(trifluoromethyl)phenyl)-3-((6-cyano-4'-fluoro-[1,1'-biphenyl]-3-yl)(methyl)amino)-2-hydroxy-2-methylpropanamide (19)

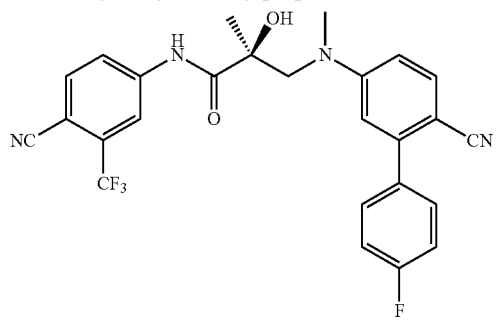 [SMILES: CN(C[C@](C)(O)C(=O)Nc1ccc(C#N)c(C(F)(F)F)c1)c1ccc(C#N)c(-c2ccc(F)cc2)c1]

Yield 38%; Brown solid; MS (ESI) 495.2 [M-H]⁻; ¹H NMR (CDCl₃, 400 MHz) δ 10.17 (bs, 1H, NH), 8.15 (s, 1H), 8.00 (d, J=2.0 Hz, 1H), 8.08 (d, J=2.0 Hz, 1H), 7.49-7.48 (m, 4H), 7.34-7.30 (m, 2H), 6.75 (m, 1H), 3.99 (d, J=14.8 Hz, 1H), 3.79 (d, J=14.8 Hz, 1H), 3.09 (s, 3H), 2.11 (bs, 1H, OH), 1.61 (s, 3H); Anal. Calcd for $C_{26}H_{20}F_4N_4O_2$: C, H, N.

Example 1A

Synthesis of Compounds 14 and 17

Synthetic Scheme of SARDs 14 and 17

Scheme 5. Preparation of SARDs 14 and 17. Resgents and conditions: (a) NaH, THF, 0° C. ~ RT; (b) CH₃I, N,N-diisopropylethylamine, 120° C., MW.

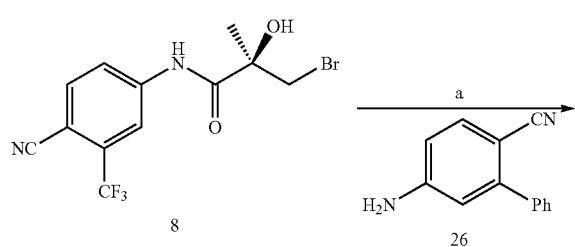

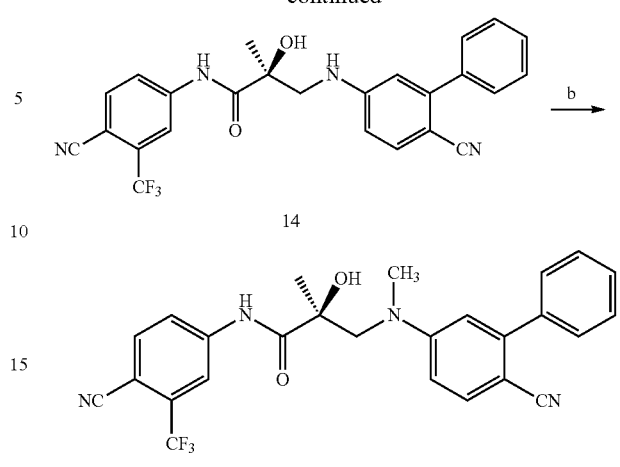

Hydroxybromide 8 was used as an important intermediate which was reacted with aniline 26 after activating by NaH in THF solvent to produce 14. N-Alkylation of 14 was a microwave assisted reaction and performed under a basic conditions in using N,N-diisopropylethylamine (Hünig's base) to generate 17.

Example 1B

Synthesis of Compounds 49 and 50

General Procedure:

Preparation of Compounds 49 and 50

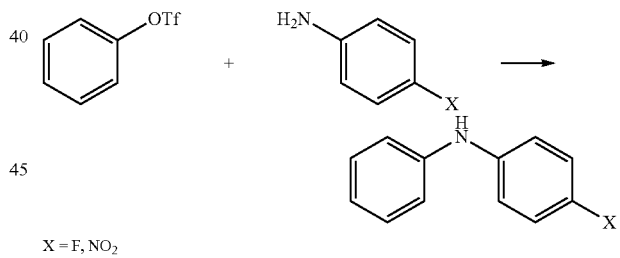

X = F, NO₂

A mixture of phenyl trifluoromethanesulfonate (500 mg, 2.21 mmol), palladium acetate (II) (50 mg, 0.22 mmol), (±) 2,2'-bis(diphenylphosphino)-1,1'-binaphthyl (317 mg, 0.66 mmol) and cesium carbonate (1.09 g, 3.31 mmol) in 50 mL of toluene were inertized with argon. Then, 4-nitroaniline (331 mg, 2.43 mmol) or 4-fluoroaniline (2.43 mmol) was added and the mixture was heated at 110° C. overnight. The reaction mixture was allowed to cool to room temperature and filtered through a pad of Celite®. The filtrate was diluted with CH₂Cl₂ and water. The phases were separated and the aqueous phase was re-extracted 2 times with CH₂Cl₂. The combined organic phases were dried over Na₂SO₄ and the resulting solution was dried over anhydrous Na₂SO₄ and purified with flash column chromatography as an eluent EtOAc/hexane (1/6, v/v) to give 4-nitro-N-phenylaniline or 4-fluoro-N-phenylaniline.

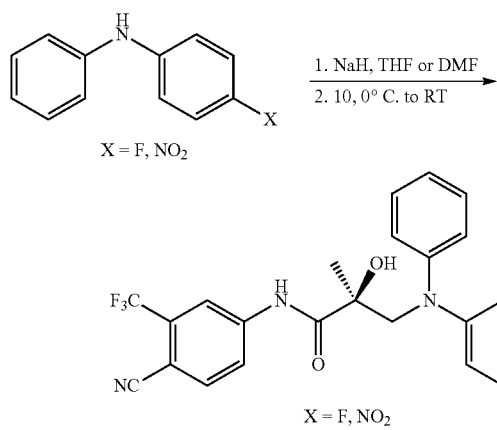

X = F, NO₂

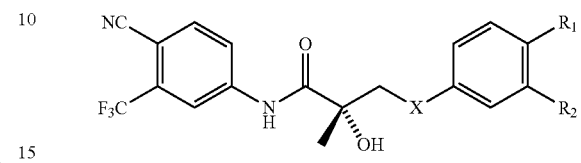

X = F, NO₂

NaH of 60% dispersion in mineral oil (228 mg, 5.7 mmol) was added in 20 mL of anhydrous THF solvent into a 100 mL dried two necked round bottom flask equipped with a dropping funnel and NH(Ph)(Ar) [Ar=4-fluorophenyl; 4-nitrophenyl] (2.84 mmol) was added to the solution under argon atmosphere in ice-water bath, and the resulting solution was stirred for 30 min at the ice-water bath. Into the flask, epoxide 10 (2.84 mmol in THF) was added through dropping funnel under argon atmosphere at the ice-water bath and stirred overnight at room temperature. After adding 1 mL of H₂O, the reaction mixture was condensed under reduced pressure, and then dispersed into 50 mL of EtOAc, washed with 50 mL (×2) water, brine, dried over anhydrous MgSO₄, and evaporated to dryness. The mixture was purified with flash column chromatography as an eluent EtOAc/hexane, and then the condensed compounds were then recrystallized in EtOAc/hexane to give a target product 49 or 50.

(S)—N-(4-Cyano-3-(trifluoromethyl)phenyl)-3-((4-fluorophenyl)(phenyl)amino)-2-hydroxy-2-methyl-propanamide (49)

Yield; 67%; MS (ESI) m/z 456.1 [M-H]⁻; ¹H NMR (400 MHz, CDCl₃) δ 8.85 (bs, 1H, NH), 7.87 (m, 1H), 7.81-7.73 (m, 2H), 7.65 (dd, J=8.4, 1.8 Hz, 1H), 7.20 (m, 2H), 7.05-7.00 (m, 2H), 6.94-6.89 (m, 5H), 4.54 (d, J=15.2 Hz, 1H), 3.84 (d, J=15.2 Hz, 1H), 3.61 (s, 1H), 1.53 (s, 3H).

Example 2

Novel AR Antagonists

The target of this research is:
(a) To synthesize and optimize orally bioavailable SARDs, and deduce structure-activity relationship (SAR).
(b) Characterize SARDs in vitro in AR ligand binding, transactivation, and AR degradation and proliferation assays in PCa cells that are dependent on AR-FL and AR-SV for growth.
(c) Determine the pharmacokinetic (PK) properties, develop appropriate formulation, and characterize SARDs in vivo in LNCaP and 22RV-1 androgen-dependent and CRPC PCa xenografts, respectively.

The preliminary results are generated with two lead molecules, compounds 17 and 14, selected from a library.

Several molecules were synthesized and characterized with the intention to develop next generation AR antagonists. Interestingly, several of these AR antagonists exhibited degradation activity at concentrations comparable to their binding and antagonistic activity. These results provided an impetus to explore the degradation activity of these molecules.

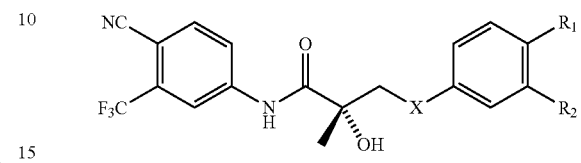

TABLE 1

SARDs of this invention, binding and AR antagonistic activities

| | X | R₁ | R₂ | $K_i$ (nM) |
|---|---|---|---|---|
| DHT | n/a | n/a | n/a | 6.62 |
| MDV-3100 | n/a | n/a | n/a | 1075.3 |
| bicalutamide | SO₂ | F | H | 545.5 |
| Cmpd 17 | N(CH₃) | CN | phenyl | 148.7 |
| Cmpd 14 | NH | CN | phenyl | 198.5 |

| | | Transcriptional Activation (Antagonist Mode) | | | |
|---|---|---|---|---|---|
| | binding | Wildtype | | W741L | |
| Compound | $K_i$ (nM) | $IC_{50}$ (nM) | % inhibition at 1 μM | $IC_{50}$ (nM) | % inhibition at 1 μM |
| DHT | 5.85 | | | | |
| bicalutamide | 545.5 | 420 | 91 | — | — |
| MDV-3100 | 1075.3 | 489 | 93 | 939 | 53 |
| ARN-509 | | 297 | | 1939.4 | |
| ASC-J9 | | 1008 | | 3487.6 | |
| 14 | 198.5 | 77 | 92 | >1000 | 48 |
| 17 | 270.7 | 95 | 98 | 101.7 | 87 |

TABLE 2

| | | Transcriptional Activation | | | DMPK (mouse liver microsomes) $T_{1/2}$ (min) $CL_{int}$ (ml/min/kg) |
|---|---|---|---|---|---|
| Compound | Binding $K_i$ (nM) | Wt. $IC_{50}$ (nM) | W741L $IC_{50}$ (nM) | T877A $IC_{50}$ (nM) | |
| DHT | 1 | | | | |
| Bicalutamide | 545.5 | 420 | — | 557 | |
| Enzalutamide | 1075.3 | 489 | 939 | 331.94 | |
| ARN-509 | | 297.0 | 1939.4 | 390.52 | |
| ASC-J9 | | 1008 | 3487.6 | | |
| 14 | 198.5 | 77 | >1000 | 48 | See Example 6 |
| 17 | 28.4 | 95 | 101.7 | 153.51 | See Example 6 |
| 49 | 275.41 | 172.22 | | | 5.069 min 136.8 ml/min/mg# | see MLM method below:

Metabolism Studies with Mouse Liver Microsomes (MLM)

Objective:
To determine the relative stability of SARDs to metabolism by liver microsomal enzyme using MLM.

Method:
Determination of metabolic stability (in vitro $CL_{int}$) of test compounds with regard to Phase I and Phase I+II metabolic pathways.

Metabolic Stability to Phase I Pathways:

The assay was done in a final volume of 0.5 ml in duplicates (n=2). Test compound (1 μM) was pre-incubated for 10 minutes at 37° C. in 100 mM Tris-HCl, pH 7.5 containing 0.5 mg/ml liver microsomal protein. After pre-incubation, reaction was started by addition of 1 mM NADPH (pre-incubated at 37° C.). Incubations were carried out in triplicate and at various time-points (0, 5, 10, 15, 30 and 60 minutes), 100 μl aliquots were removed and quenched with 100 μl of acetonitrile containing internal standard. Samples were vortex mixed and centrifuged at 4000 rpm for 10 minutes. The supernatants were transferred to 96 well plates and submitted for LC-MS/MS analysis. As control, sample incubations done in absence of NADPH were also included. From % PCR (% Parent Compound Remaining), rate of compound disappearance is determined (slope) and in vitro $CL_{int}$ (μl/min/mg protein) was calculated.

Metabolic Stability in Phase I & Phase II Pathways:

In this assay, test compound was incubated with liver microsomes and disappearance of drug was determined using discovery grade LC-MS/MS. To stimulate Phase II metabolic pathway (glucuronidation), UDPGA and alamethicin (a pore-forming peptide to increase microsomal activity) were included in the assay.

LC-MS/MS Analysis:

The analysis of the compounds under investigation was performed using LC-MS/MS system consisting of Agilent 1100 HPLC with an MDS/Sciex 4000 Q-Trap™ mass spectrometer. The separation was achieved using a C18 analytical column (Alltima™, 2.1×100 mm, 3 μm) protected by a C18 guard cartridge system (SecurityGuard™ ULTRA Cartridges UHPLC for 4.6 mm ID columns, Phenomenex). Mobile phase was consisting of channel A (95% acetonitrile+5% water+0.1% formic acid) and channel C (95% water+5% acetonitrile+0.1% formic acid) and was delivered at a flow rate of 0.4 mL/min. The volume ratio of acetonitrile and water was optimized for each of the analytes. Multiple reaction monitoring (MRM) scans were made with curtain gas, collision gas, nebulizer gas, and auxiliary gas optimized for each compound, and source temperature at 550° C. Molecular ions were formed using an ion spray voltage (IS) of −4200 V (negative mode). Declustering potential (DP), entrance potential (EP), collision energy (CE), product ion mass, and cell exit potential (CXP) were optimized for each compound.

As shown in Table 1, the first-generation SARDs were generated with amino linkers. Their binding and AR antagonistic activities were compared to standard molecules such as bicalutamide, enzalutamide (MDV3100), ARN-509, and ASC-J9.

As shown in Table 1 and Table 2, the SARDs of the invention bound to AR with higher affinity than the reference standards. Interestingly, two molecules in the list, compounds 14 and 17 robustly bound to AR by displacing the radiolabeled mibolerone from LBD in an AR-LBD binding assay. They bound at a much higher affinity than the reference standards. Consistent with potent binding, the two molecules effectively antagonized the R1881 stimulated wild type AR transcriptional activity by potencies at least five-fold greater than MDV-3100 and bicalutamide (77 nM and 95 nM for 14 and 17, respectively, compared to 420 nM and 489 nM for bicalutamide and MDV-3100, respectively) (Table 1 and Table 2).

Bicalutamide is a known agonist of AR containing W741L mutation, whereas MDV-3100 retains antagonist activity though its potency is somewhat reduced (939 nM). While 14 demonstrated reduced effectiveness in the W741L mutant (>1 μM), 17 retained the ability to antagonize agonist activated W741L AR (101.7 nM). The W741L mutation was selected due to the structural similarity of SARDs to bicalutamide (aryl propanamide). The antagonist activity of 17 was selective for the AR and did not cross-react with progesterone receptor (PR), mineralocorticoid receptor (MR) or glucocorticoid receptors (GR) (data not shown).

TABLE 3

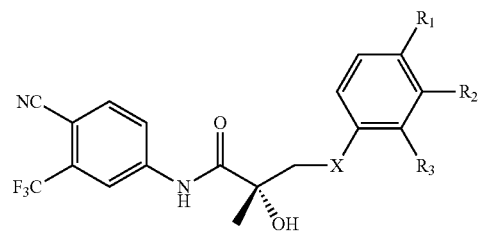

| Compound | X | $R_1$ | $R_2$ | $R_3$ | RBA | WT Agonist $EC_{50}$ (nM) | $E_{max}$ (nM) | WT Antagonist $IC_{50}$ (nM) | % inhibition at 1 μM |
|---|---|---|---|---|---|---|---|---|---|
| S-22 | O | CN | H | H | 5.8 ± 1.8 | 1.4 | 140 ± 15.1 | NA | NA |
| Bicalutamide | $SO_2$ | F | H | H | 0.62 ± 0.06 | NA | NA | 22.4 ± 6.7 | 90.9 ± 0.83 |
| 12 | NH | CN | H | H | 0.16 ± 0.01 | 626 | 156 ± 213.4 | 119 | 89.9 ± 0.4 |
| 13 | NH | CN | —(CH)$_4$— | | 1.5 ± 0.05 | >1000 | 48.3 ± 7.4 | 193 | 63.0 ± 1.2 |
| 14 | NH | CN | Ph | H | 0.56 ± 0.03 | NA | NA | 20.5 | 88.2 ± 1.1 |
| 15 | NH | CN | H | Ph | 0.65 ± 0.06 | >1000 | 22.6 ± 6.4 | 81.3 | 92.2 ± 1.0 |
| 18 | $NCH_2$ ($C_6H_6$) | CN | H | H | ND | NA | NA | 118.6 | 92.7 ± 1.8 |
| 17 | $NCH_3$ | CH | Ph | H | | NA | NA | 6 | 94.8 |

TABLE 4

| Compound | X | $R_1$ | $R_2$ | $R_3$ | W741L Agonist $EC_{50}$ (nM) | W741L Agonist $E_{max}$ (nM) | W741L Antagonist $IC_{50}$ (nM) | W741L Antagonist % inhibition at 1 μM | T877A Agonist $EC_{50}$ (nM) | T877A Agonist $E_{max}$ (nM) | T877A Antagonist $IC_{50}$ (nM) | T877A Antagonist % inhibition at 1 μM |
|---|---|---|---|---|---|---|---|---|---|---|---|---|
| Bicalutamide | $SO_2$ | F | H | H | 1.1 ± 3.4 | 273 ± 37.9 | NA | NA | NA | NA | 229 | 73.7 ± 7.4 |
| 12 | NH | CN | H | H | >1000 | 24.8 ± 7.2 | >1000 | 20.9 ± 9.1 | 47 | 122 ± 26.4 | NA | NA |
| 13 | NH | CN | —$(CH)_4$— | | 2.4 | 93.1 ± 10.8 | NA | NA | 3.4 | 56.1 ± 9.9 | 784.4 | 60.5 ± 7.8 |
| 14 | NH | CN | Ph | H | >1000 | 26.8 ± 1.6 | >1000 | 48.3 ± 4.7 | >1000 | 20.6 ± 3.6 | 79.1 | 85.6 ± 2.0 |
| 15 | NH | CN | H | Ph | 1.9 | 76.7 ± 15.1 | 305 | 63.8 ± 13.8 | >1000 | 18.6 ± 0.1 | 34.3 | 94.0 ± 0.7 |
| 18 | $NCH_2(C_6H_6)$ | CN | H | H | >1000 | 26.1 ± 1.7 | >1000 | 47.6 ± 10.0 | >1000 | 17.4 ± 5.4 | 470 | 74.8 ± 8.7 |
| 17 | $NCH_3$ | CH | Ph | H | NA | NA | 101.7 | 87 | NA | NA | 33.1 | 95.6 |

In general, compounds 12-21 acted as antagonists of wildtype androgen receptor (wt-AR) with some residual agonism for 12, 13, and 15. Notably, 17 was the most potent antagonist with an $IC_{50}$ value of 6 nM (Table 3). Mutant AR's W741L and T877A confer resistance to bicalutamide and hydroxyflutamide, respectively. Most of the compounds 12-21 displayed mixed agonist/antagonist activity in in vitro transcriptional activation assays. However, 17 retains potent pure antagonism in wildtype and both mutations (Table 3 and Table 4), demonstrating potential to overcome resistance to bicalutamide and/or hydroxyflutamide, independent of its SARD activity (described below). 14 also demonstrated antagonist activity in wildtype and mutant AR's, but was not a potent antagonist in all the mutants tested.

Example 3

AR Degradation Activity

Figure 2A:
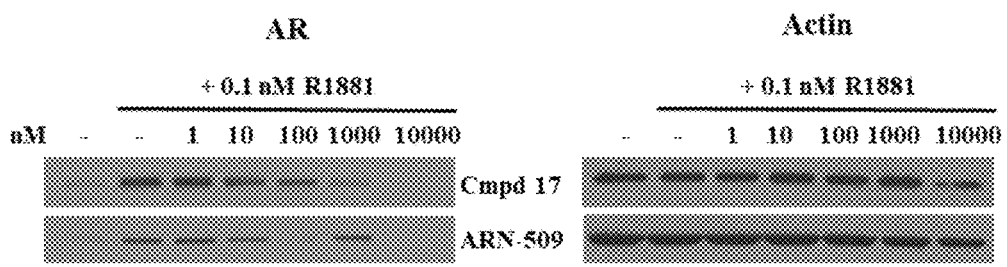
FIG. 2A and FIG. 2B depict the AR degradation by SARD compound 17 in LNCaP cells. (A) LNCaP cells were plated in serum free medium and treated with the indicated concentrations of compound 17 and ARN-509 in the presence or absence of R1881. Cells were harvested, protein extracted and Western blotted for AR and actin. (B) LNCaP cells were plated in 96 well plates at 10,000 cells/well in RPMI+1% csFBS without phenol red. Cells were treated as indicated above in combination with 0.1 nM R1881 for 6 days with medium change on day 3. At the end of 6 days, the cells were fixed and stained with sulphorhodamine blue stain to measure cell growth. Enzalutamide and ARN-509 are other AR antagonists reported to degrade AR.
Figure 4:
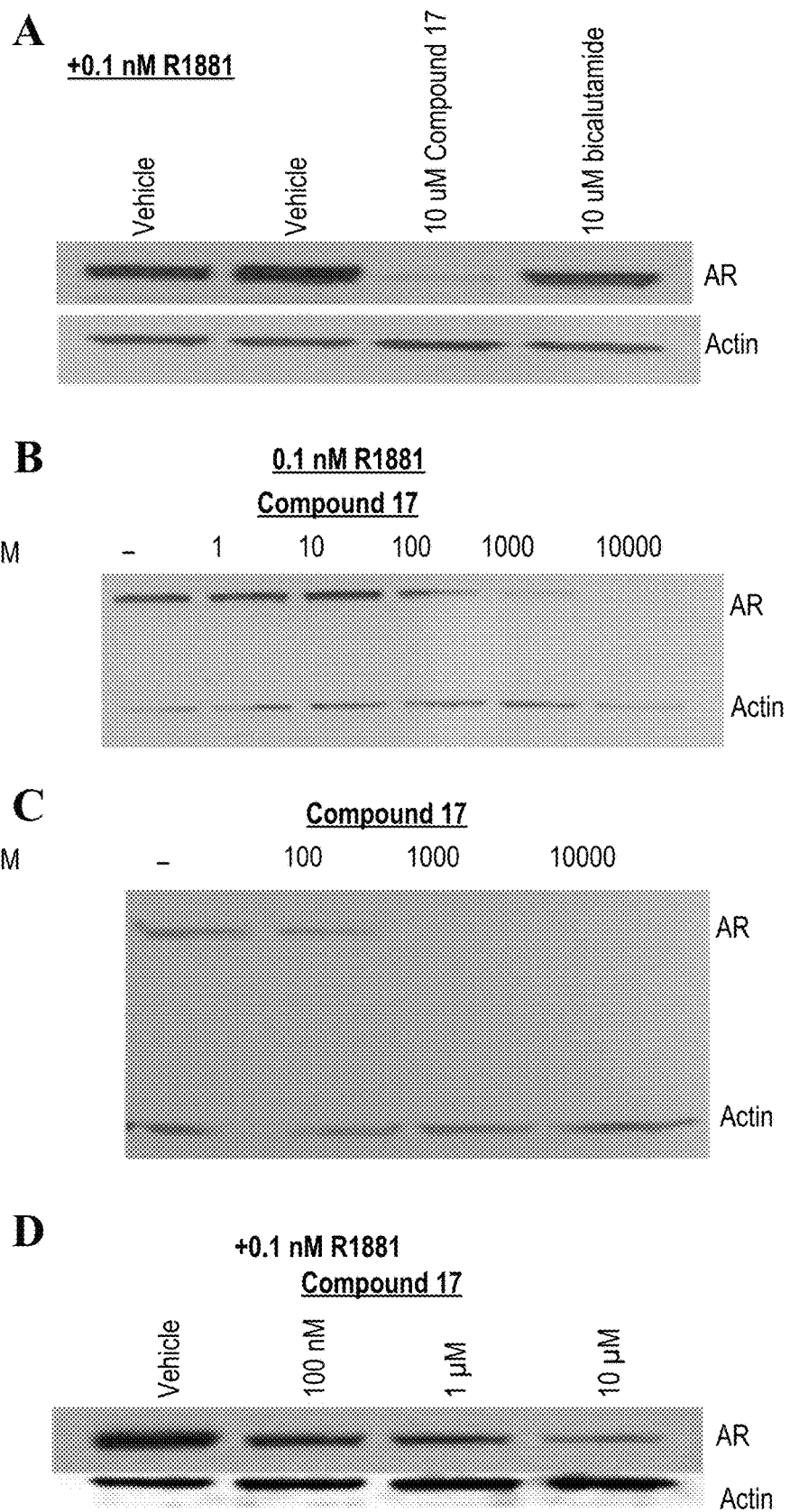
FIG. 4 depicts degradation of AR by SARDs under varying conditions (A-D), without degradation of other receptors (E-F). (A) and (B) LNCaP cells were serum starved and treated with compound 17 (10 uM in panel A and a dose response in panel B) in the presence or absence of R1881. Bicalutamide was used as a negative control. Cells were harvested, protein extracted, and Western blotted for AR and actin. (C) LNCaP cells were plated in full serum and treated with compound 17 (dose response). Cells were harvested, protein extracted, and Western blotted for AR and actin. (D) HeLa cells were infected with adenovirus containing AR and were treated with compound 17 in the presence or absence of R1881. Cells were harvested, protein extracted, and Western blotted for AR and actin. (E) and (F) SARDs do not degrade other nuclear receptors. T47D (left panel) and MCF-7 (right panel) cells were plated in full serum and treated with compound 17 (dose response). Cells were harvested, protein extracted, and Western blotted for PR (progesterone receptor) or ER-α (estrogen receptor-alpha) and actin.
Figure 4:
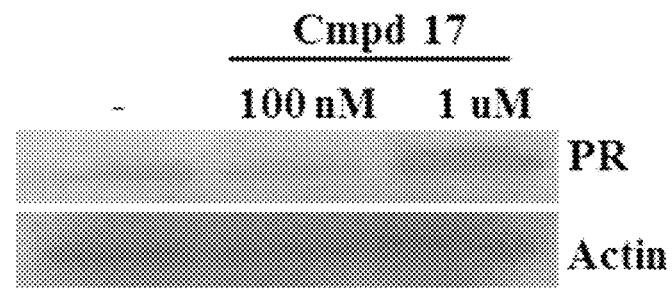
Figure 4:
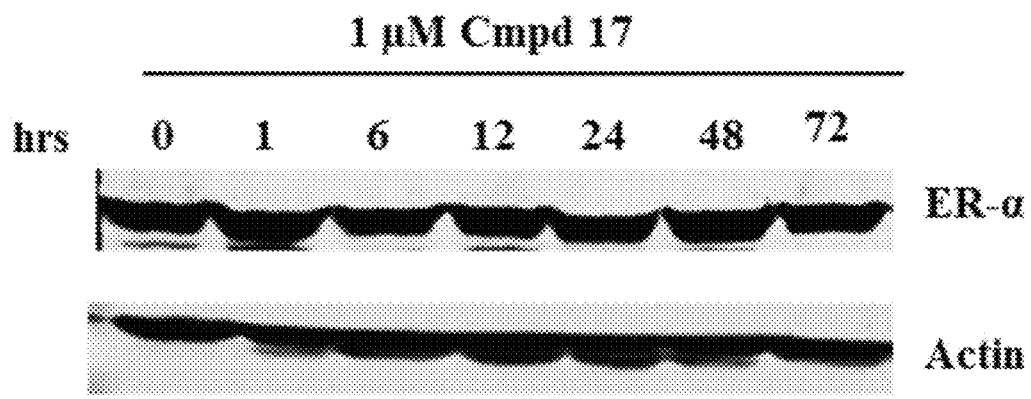

Compounds 17 and 14 were tested for their effect on AR protein expression. While 17 drastically reduced the levels of AR protein following 24 hours of treatment in LNCaP cells (serum starved and treated with 0.1 nM R1881) as measured by Western blot (FIG. 1A), bicalutamide or enzalutamide (MDV-3100) had no effect at an equal concentration (FIGS. 1E (VCaP) and 1F (LNCaP)). Under identical conditions, the lowest concentration of 17 that was capable of reducing AR protein levels in LNCaP cells was 100 nM (FIG. 1B). Similar AR protein down-regulation was observed under hormone replete conditions in LNCaP (FIG. 1C), in HeLa cells infected with an adenovirus expressing high levels of wt-AR (FIG. 1D; suggesting activity in CPRC where AR gene has been activated) as well as in wt-AR expressing VCaP cells 14 (FIG. 1E). 14 also similarly reduced the AR levels in LNCaP cells, requiring as little as 2 hours of treatment and matching closely the time course of 17-AAG (FIG. 1F). Neither bicalutamide nor MDV-3100 (enzalutamide) had any effect on AR protein levels even after 24 hours of treatment. Likewise 17 demonstrated more potent and complete AR degradation in LNCaP cells than the reported SARDs ASC-J9 (not shown) and ARN-509 (FIG. 2A), and AR antagonist enzalutamide (not shown) (FIG. 2A). 17 and 14 treatment in LNCaP cells resulted in small reductions in AR mRNA levels, but only at 10 μM and not at 1 μM. Unlike the HSP-90 inhibitor 17-AAG, 17 treatment did not affect PR (FIG. 4E), GR (not shown) and ERα (FIG. 4F) protein levels (FIG. 4).

Figure 9:
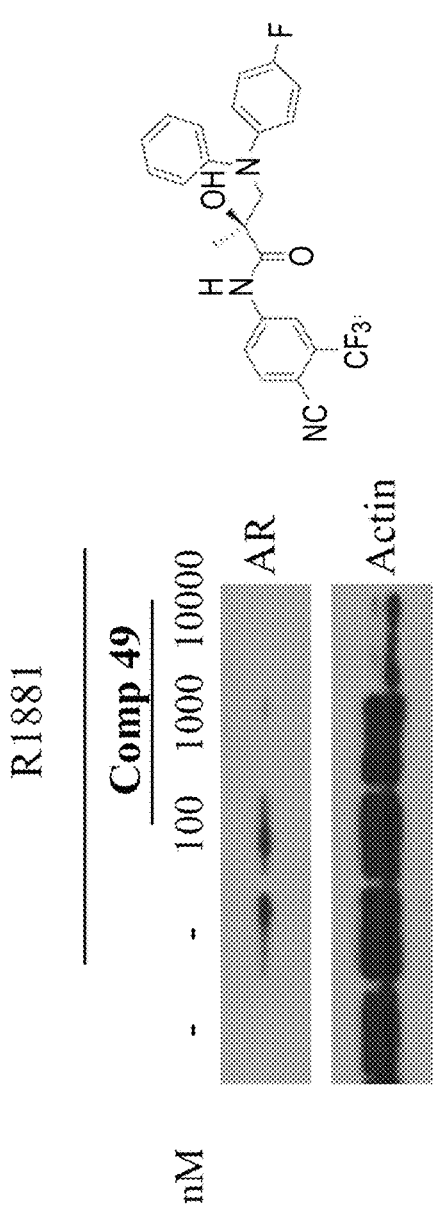
FIG. 9 depicts that 49 in the presence of R1881 degrades AR in LNCaP cells. LNCaP cells were plated in 6 well plates at 1 million cells/well. The cells were maintained in serum free conditions for 3 days. The cells were treated as indicated in the figure, harvested, protein extracted, and Western blotted for AR. 49 (and other SARDs disclosed herein) demonstrated selective degradation of AR (i.e., SARD activity) in the nM range, i.e., at concentrations comparable to their antagonist $IC_{50}$ values. LNCaP cells are known to express the AR mutant T877A, demonstrating the ability of SARDs of this invention to degrade antiandrogen resistance conferring mutant androgen receptors.

FIG. 9 depicts that 49 in the presence of R1881 degrades AR in LNCaP cells. LNCaP cells were plated in 6 well plates at 1 million cells/well. The cells were maintained in serum free conditions for 3 days. The cells were treated as indicated in the figure, harvested, protein extracted, and Western blotted for AR. 49 and other SARDs of this invention demonstrated selective degradation of AR (i.e., SARD activity) in the nM range, i.e., at concentrations comparable to their antagonist $IC_{50}$ values. LNCaP cells are known to express the AR mutant T877A, demonstrating the ability to degrade antiandrogen resistance conferring mutant androgen receptors.

Figure 10:
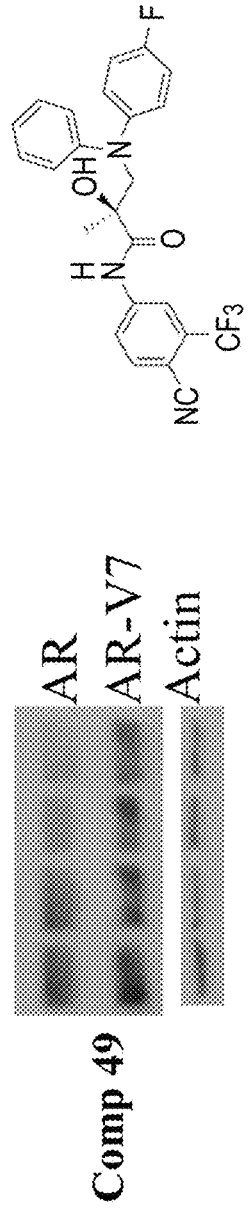
FIG. 10 depicts that 49 degrades AR in RV22-1 cells. 22RV-1 cells were plated in a 6 well plate at 1-1.5 million cells/well in growth medium (RPMI+10% FBS). Next day, medium was changed and treated with vehicle or a dose response of 49. After overnight treatment (12-16 hrs), cells were washed in ice cold PBS and harvested by scrapping in 1 mL PBS. Cells were pelleted, protein extracted, quantified using BCA assay, and equal quantity of protein was fractionated on a SDS-PAGE. The proteins were transferred to nylon membrane and Western blotted with AR antibody (N20 from SCBT) and actin antibody. 49 (and other SARDs disclosed herein) was capable of degrading full length androgen receptor (AR-FL) and truncated AR (AR-SV) in 22RV-1 cells, suggesting that SARDs of this invention may be able to overcome AR-V7 dependent prostate cancers.

FIG. 10 depicts that 49 degrades AR in RV22-1 cells. 22RV-1 cells were plated in 6 well plate at 1-1.5 million cells/well in growth medium (RPMI+10% FBS). Next day, medium was changed and treated with vehicle or a dose response of 49. After overnight treatment (12-16 hrs), cells were washed in ice cold PBS and harvested by scrapping in 1 mL PBS. Cells were pelleted, protein extracted, quantified using BCA assay, and equal quantity of protein was fractionated on a SDS-PAGE. The proteins were transferred to nylon membrane and Western blotted with AR antibody (N20 from SCBT) and actin antibody. 49 was capable of degrading full length androgen receptor (AR-FL) and truncated AR (AR-SV) in 22RV-1 cells, suggesting that SARDs will be able to overcome AR-V7 dependent prostate cancers.

LNCaP cells are known to express the AR mutant T877A, demonstrating the ability of the SARDs of this invention to degrade antiandrogen resistance conferring mutant androgen receptors (i.e., advanced prostate cancers and CRPC). 14, 17 and 49 were capable of degrading full length androgen receptor (AR-FL) and truncated AR (AR-V7) in 22RV-1 cells, suggesting that SARDs will be able to overcome AR-V7 dependent prostate cancers (i.e., CRPC).

These SARD activity demonstrations suggest the compounds of this invention are able to degrade a variety of AR variants, and hence should provide the ability to inhibit the AR-axis activity whether it is androgen-dependent or androgen-independent. Degradation of the AR removes the possibility of promiscuous activation of mutant ARs, activation by intracellular processes such as signal transduction and kinase activation, etc.; and suggests that the SARDs should also degrade the polyQ polymorphism in hyperandrogenic dermatologic disorders (shortened polyQ) or Kennedy's disease (extended polyQ), providing a rationale for treating either type of diseases by destroying the AR in the affected tissues (skin and neuromuscular system, respectively).

Example 4

Effect on PCa Gene Expression and Cell Growth

The ability of these novel antagonists to inhibit AR-regulated gene expression was measured in LNCaP, a PCa cell line known to harbor a T877A mutation (Table 5).

TABLE 5

Effect of antagonists on AR-target gene expression and growth in LNCaP cells.

| | Gene Expression + 0.1 nM R1881 ($IC_{50}$ nM) | | |
|---|---|---|---|
| Gene | Bicalutamide | MDV-3100 | Cmpd 17 |
| PSA | 783.7 | 1,019.3 | 198.5 |
| NKx3.1 | 755.8 | 1,142.8 | 176.0 |
| FKBP51 | 270.9 | 76.8 | 51.8 |
| TMPRSS2 | 831.4 | 823.7 | 128.1 |
| Growth | | 872 | 469 |

Consistent with binding and transcriptional activation assays, 17 significantly inhibited agonist-stimulated expression of PSA, NKx3.1, FKBP51, and TMPRSS2 genes ($IC_{50}$ values of 198.5, 176.0, 51.8, and 128.1 nM, respectively).

TABLE 6

| Cell Line/ | Cmpd 17 7 Day Growth ($IC_{50}$, µM) | | | | 17-AAG 7 Day Growth ($IC_{50}$, µM) | | | | Enzalutamide 7 Day Growth ($IC_{50}$, µM) | | | |
|---|---|---|---|---|---|---|---|---|---|---|---|---|
| R1881 | Veh | 0.01 | 0.1 | 10 | Veh | 0.01 | 0.1 | 10 | Veh | 0.01 | 0.1 | 10 |
| VCaP | 2.99 | 2.92 | 2.48 | 3.82 | 0.657 | 0.414 | 0.778 | 1.06 | 0.742 | 1.53 | >3 | >10 |
| LNCaP | 0.78 | 0.49 | 0.47 | — | 0.260 | 0.292 | 0.157 | — | 0.281 | 0.656 | 3.02 | — |
| PC-3 | >10 | >10 | >10 | >10 | 0.307 | 0.221 | 0.257 | 0.542 | >10 | >10 | >10 | >10 |

Figure 2B:
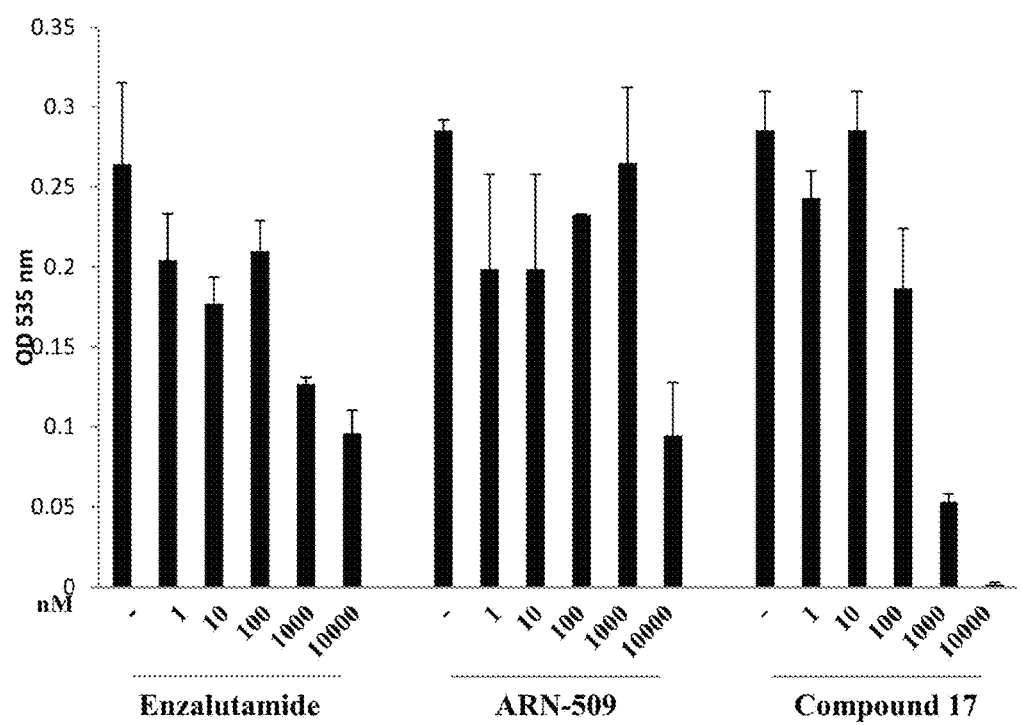

Similar activity was demonstrated in LNCaP cells with 14 (not shown). Consistent with inhibition of gene expression, 17 inhibited growth of AR-positive, androgen-dependent PCa cells (LNCaP and VCaP) in both the hormone-deplete and hormone-replete states (Table 6). Unlike the HSP-90 inhibitor 17-AAG, 17 had no effects in the AR negative PC cell line, PC-3 (Table 6). See also FIG. 2B for a bar graph that depicts that 17 inhibited growth of LNCaP cells with comparable efficacy and potency as enzalutamide and ARN-509.

Example 5

SARDs Degrade AR-SV in 22RV-1 Cells

Figure 3:
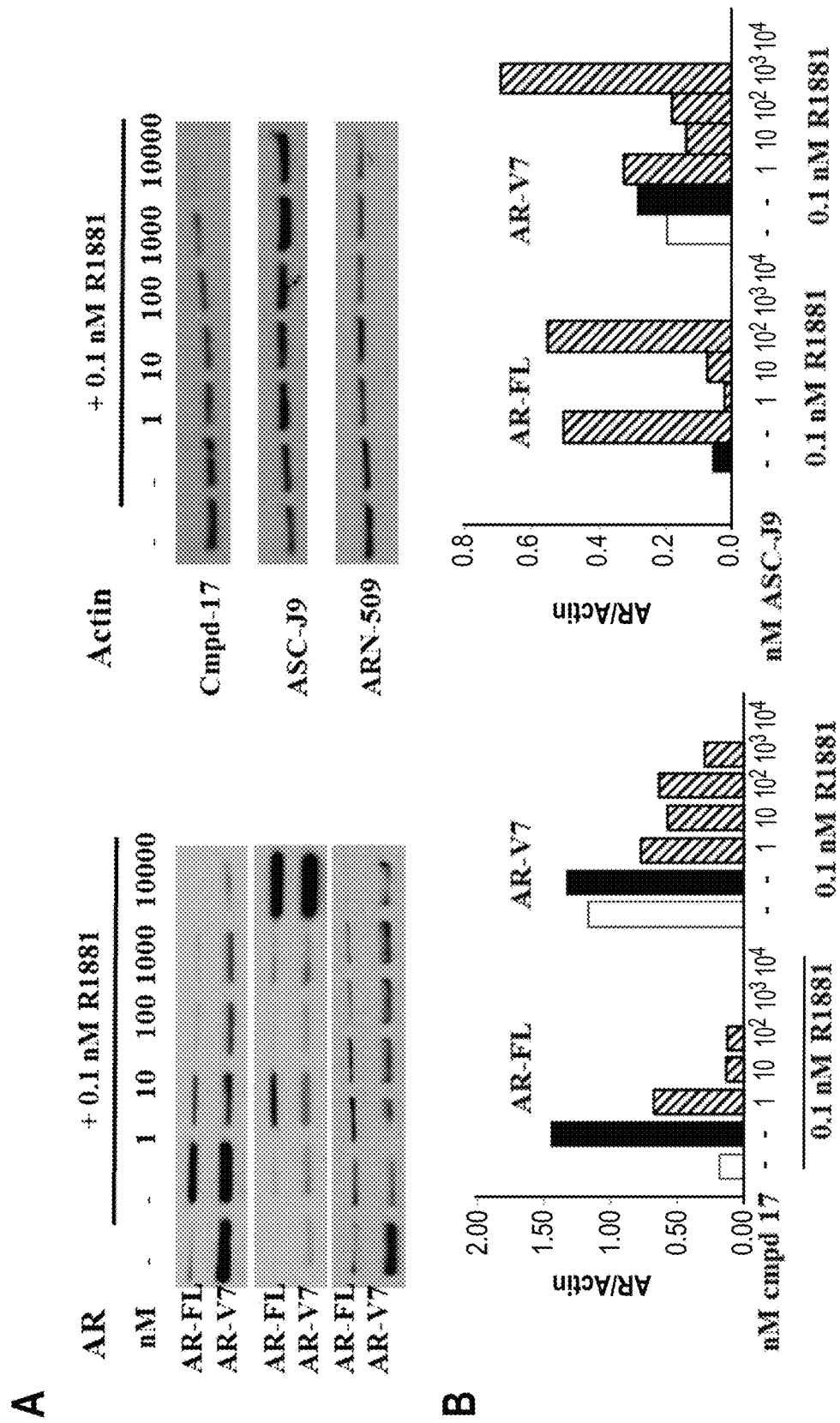
FIG. 3 depicts the effect of SARDs on AR-FL and AR-SV protein levels. (A) and (B) SARD 17 degrades AR full length and splice variant in 22RV-1 cells. 22RV-1 cells were plated in serum free medium and treated with the indicated concentrations of compound 17, ARN-509 or ASC-J9 in the presence or absence of R1881. Cells were harvested, protein extracted and Western blotted for AR and actin. Blots were quantified using Image-J (panel B). (C) Same experiment repeated with compound 14. AR-FL—androgen receptor-full length; AR-V7—androgen receptor splice variant 7 (lacks ligand binding domain); ARN-509 and ASC-J9 are other AR antagonists reported to degrade AR.
Figure 3:
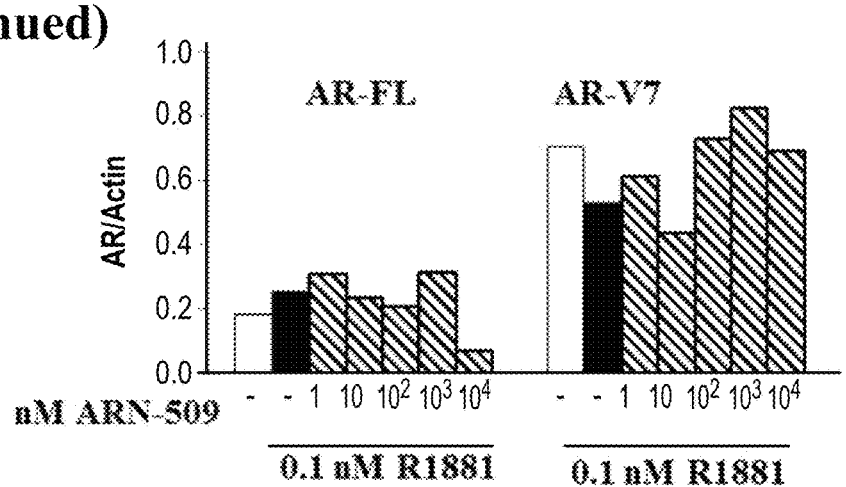
Figure 3:
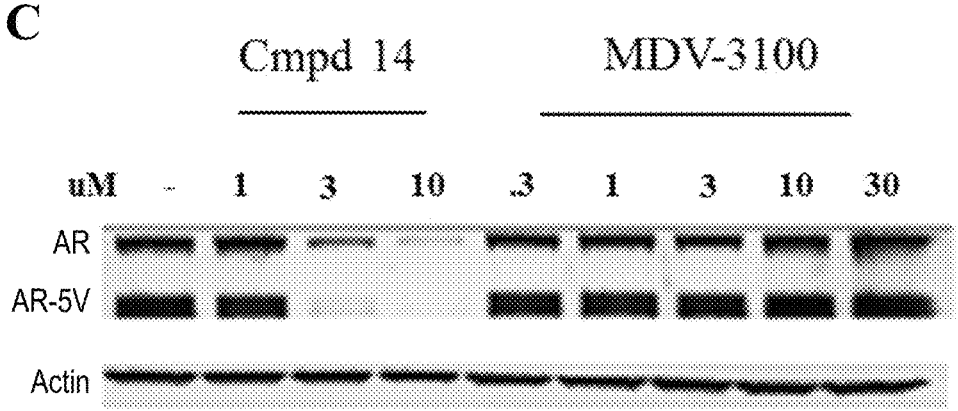

The effect of SARD treatment on the AR levels was also measured in androgen-refractory 22RV-1 PCa cells. These cells express both AR-FL and the low molecular weight splice variant species of the AR (AR-SV) and depend on the AR-SV for growth. 17 (FIGS. 3A and 3B) and 14 (FIG. 3C) completely down regulated both AR-FL and AR-SV species (FIG. 3) in contrast to the limited effects of 17-AAG only on AR-FL (not shown). MDV-3100 treatment did not affect levels of either AR species (FIG. 3C), and ASC-J9 and ARN-509 did not reduce AR-V7 levels. Growth assay performed in 22RV-1 cells treated with SARDs in the presence or absence of 0.1 nM R1881 demonstrated that SARDs, but not MDV-3100, bicalutamide, enzalutamide, or ARN-509, markedly suppressed the growth of 22RV-1 cells (Table 7). The AR-SV variant (e.g., AR-V7; *Cancer Res.* 2013 Jan. 15; 73(2): 483-489) lacks the LBD and so SARD activity against AR-SV must operate through an alternative binding and degradation domain (BDD).

TABLE 7

Effect of SARDs on AR transactivation and growth in 22RV-1 cells.

| Compound | Transactivation $IC_{50}$ (nM) | Growth $IC_{50}$ (nM) |
|---|---|---|
| Bicalutamide | 3133.52 | >10,000 |
| Enzalutamide | 101.87 | >10,000 |
| Cmpd 17 | 56.36 | 2642 |
| ARN-509 | 64.54 | >10,000 |
| ASC-J9 | 1026.91 | >10,000 |

FIG. 4 depicts degradation of AR by SARDs under varying conditions (A-D), without degradation of other receptors (E-F). (A.) and (B.) LNCaP cells were serum starved and treated with compound 17 (10 uM in panel A and a dose response in panel B) in the presence or absence of R1881. Bicalutamide was used as a negative control. Cells were harvested, protein extracted, and Western blotted for AR and actin. (C.) LNCaP cells were plated in full serum and treated with compound 17 (dose response). Cells were harvested, protein extracted, and Western blotted for AR and actin. (D.) HeLa cells were infected with adenovirus containing AR and were treated with compound 17 in the presence or absence of R1881. Cells were harvested, protein extracted, and Western blotted for AR and actin. (E.) and (F.) SARDs do not degrade other nuclear receptors. T47D (left panel) and MCF-7 (right panel) cells were plated in full serum and treated with compound 17 (dose response). Cells were harvested, protein extracted, and Western blotted for PR (progesterone receptor) or ER-α (estrogen receptor-alpha) and actin.

Example 6

Liver Metabolism and Pharmacokinetic (PK) Properties of SARDs

To evaluate the metabolic stability parameters such as half-life and clearance, human, rat, and dog liver microsomes were incubated with 17 and 14 for 60 min. Both molecules had very short half-lives between 5 and 10 min and high clearance (Table 8).

TABLE 8

DMPK studies with SARDs of the invention.

| SARD | Rat PK | | | Rat LM - P1 Half Life (min) | Rat LM - P1 CL (µL/min/mg) | Rat LM - P1 Half Life (min) | Rat LM - P1 CL (µL/min/mg) |
|---|---|---|---|---|---|---|---|
| | CL_obs (mL/min/kg) | IV AUC all (min* µg/mL) | PO_F % | | | | |
| 17 | 30.4 | 323.4 | 0.7 | 4.6 | 150.9 | 2.5 | 281.4 |
| 14 | 9.4 | 1067.9 | 0.4 | 7.0 | 99.5 | 2.6 | 266.0 |

PK studies in rats to follow up the metabolism data also demonstrated that the SARDs have very low bioavailability and area under the curve (AUC) (Table 8), indicating that their PK properties need to be improved by structural modifications and optimal formulation in order to obtain systemic exposures necessary for oral administration and efficacy for, e.g., prostate cancer. However, the high potency and efficacy of the selective androgen receptor degradation coupled with the low half-lives and high metabolic clearances suggest that topical administration of the compounds of this invention could exert strong (high potency and high efficacy) antiandrogenic effects when applied topically directly to affected areas. E.g., topical administration to localized skin lesions such as in acne, seborrheic dermatitis, hirsutism, etc. could degrade the AR in these tissues, thereby countering the hyperandrogenism, without risk of significant systemic exposures that could result in untoward anti-anabolic or sexual side effects.

Example 7

Effects on Androgen-Dependent Tissues in Intact Male Rats

Figure 5:
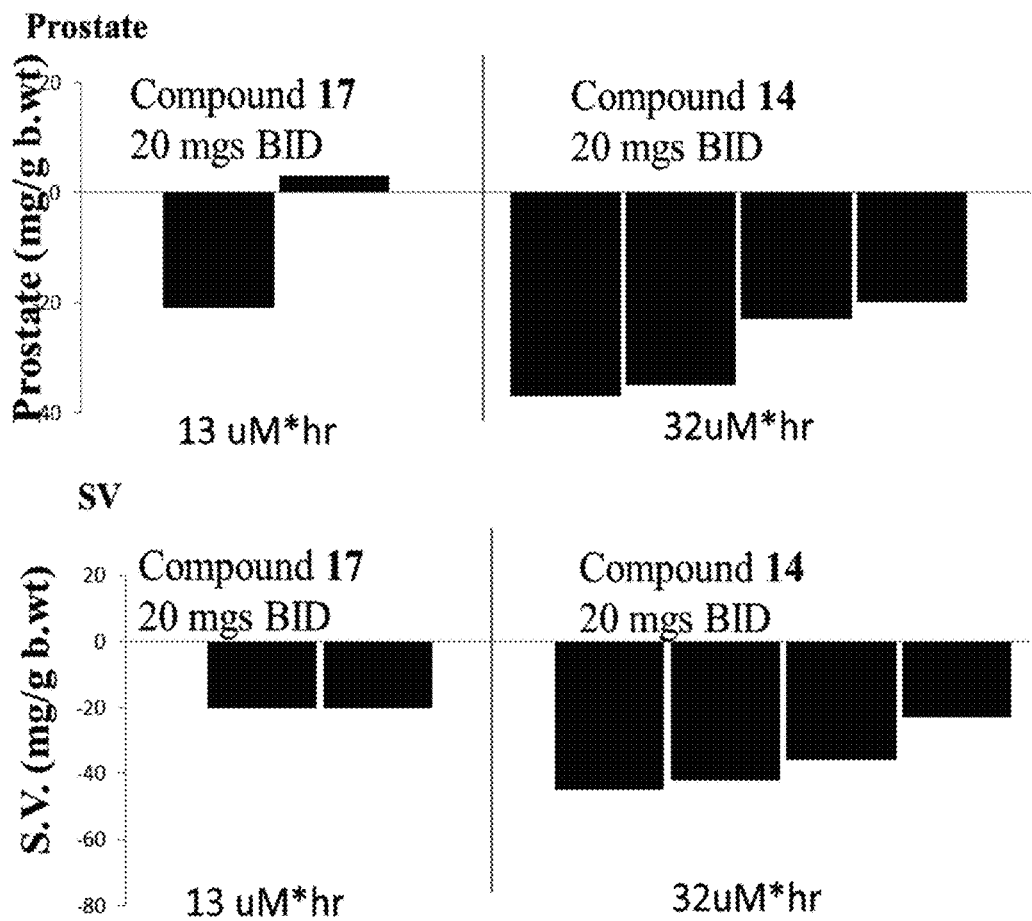
FIG. 5 depicts the effect of SARDs 17 and 14 on AR-target tissues (SV or S.V.—seminal vesicles and prostate) in the Hershberger assay. The numbers at the bottom of the graphs are the area under the curve (AUC) for drug concentration.

To measure in vivo antagonist activity, 17 and 14 were administered to intact male rats via intravenous (i.v.) bolus injection (FIG. 5). Due to high clearance, studies with oral administration of these molecules failed to significantly affect any androgen-dependent tissues such as prostate, seminal vesicles, or levator ani. Hence, the study was conducted with i.v. administration to derive evidence of in vivo activity. Following 3 days of therapy, reductions in prostate weight normalized to body weight were observed in 1 of 2 17-treated animals, and 3 of 4 14-treated animals as compared to vehicle-treated controls. Reductions of greater magnitude in seminal vesicle weight were observed in 4 of 4 animals treated with 14 with no changes in 17 animals. Both compounds tested varied greatly in the exposures following 23 mpk 14 and 23 mpk 17 doses resulting in 32 and 13 µM*hr exposures, respectively. These studies indicate the requirement for molecules with better bioavailability or formulation that will enhance the oral bioavailability and efficacy in achieving systemic antiandrogenic effects.

Example 8

SARDs do not Inhibit Transactivation of Other Receptors

Figure 6:
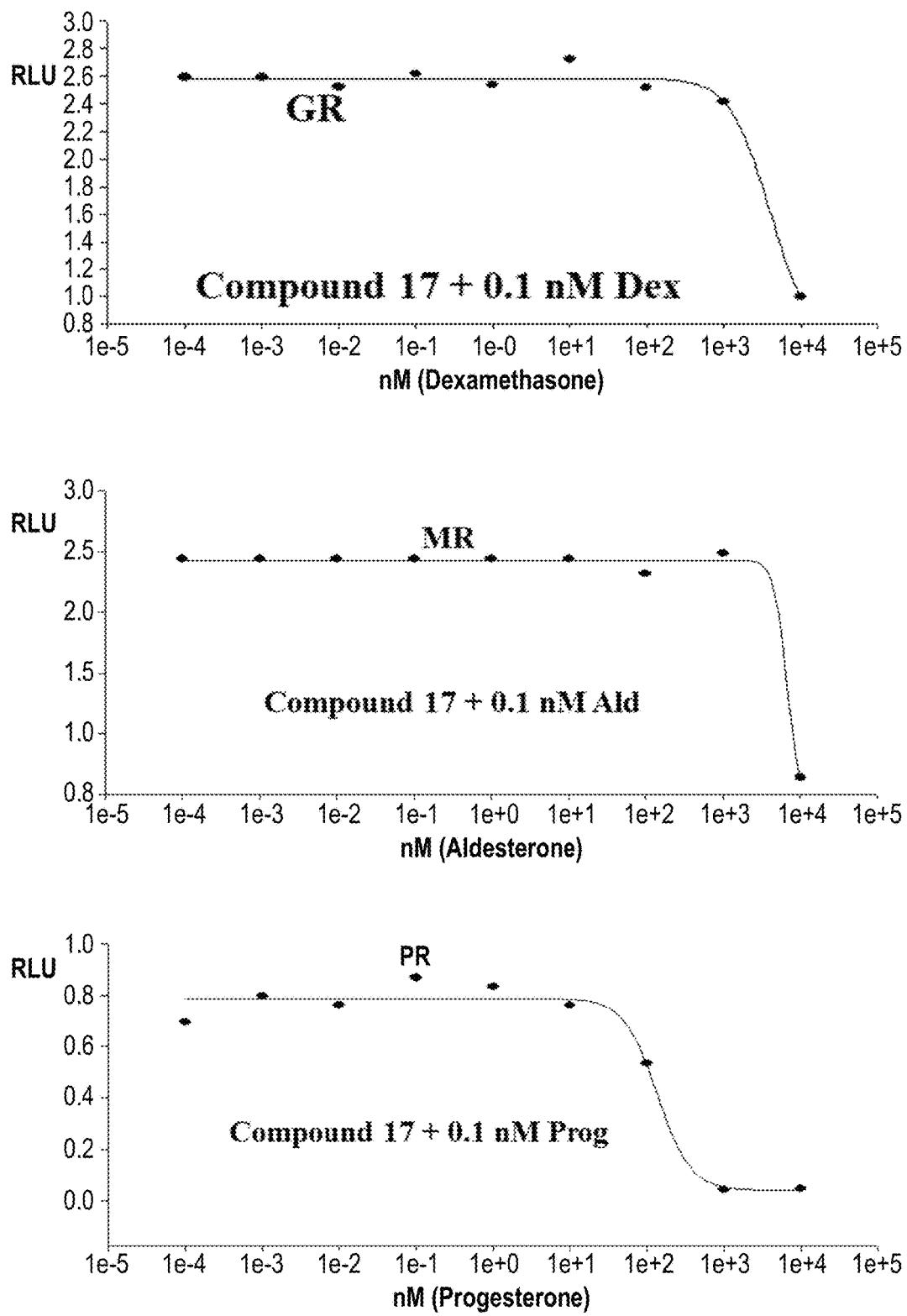
FIG. 6 depicts that SARDs do not inhibit transactivation of other receptors until 10 uM. HEK-293 cells were transfected with the indicated receptors and GRE-LUC and CMV-renilla luc. Cells were treated with 17 for 24 hrs after transfection and luciferase assay performed 48 hrs after transfection. GR—glucocorticoid receptor; Dex—dexamethasone; MR—mineralocorticoid receptor; Ald—aldosterone; PR—progesterone receptor; and Prog—progesterone.

HEK-293 cells were transfected with the indicated receptors and GRE-LUC and CMV-*renilla* luc. Cells were treated 24 hrs after transfection and luciferase assay performed 48 hrs after transfection. SARDs did not inhibit transactivation of other receptors until 10 uM (FIG. 6).

Example 9

Figure 7:
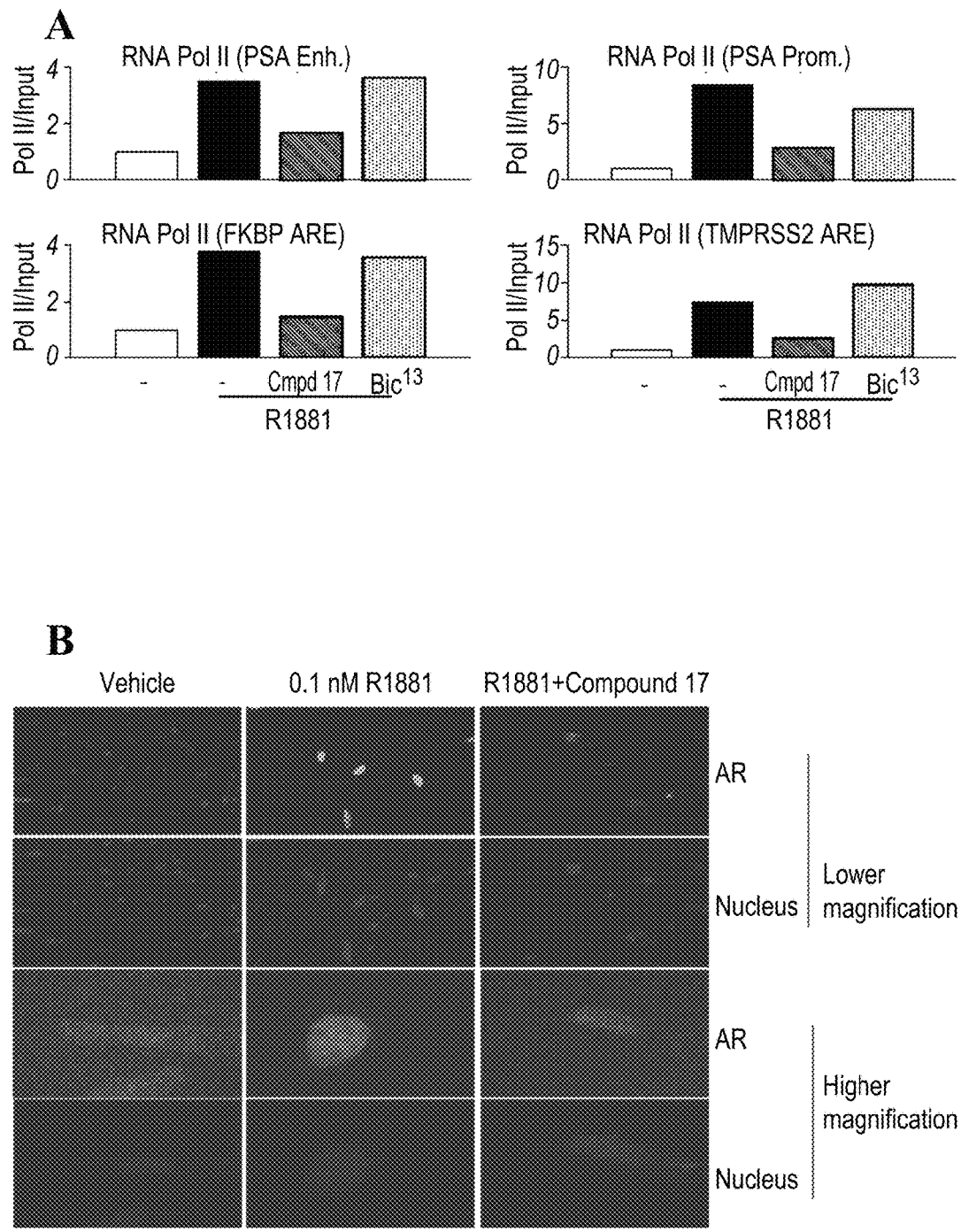
FIG. 7 depicts that SARD treatment inhibited AR recruitment to the promoter of androgen responsive genes (PSA, FKBP, & TMPRSS2) and lowered AR levels in the nucleus in R1881 treated animals. (A) LNCaP cells were serum starved for 3 days and treated as indicated above with SARD (17) or bicalutamide at 10 uM in the presence or absence of 0.1 nM R1881. Proteins were cross-linked to DNA and chromatin immunoprecipitation studies were conducted with AR and RNA-Pol II antibodies. (B) SARDs degrade AR. LNCaP cells were serum starved for 3 days and treated as indicated above with SARD (17) at 10 uM in the presence or absence of 0.1 nM R1881. Cells were fixed and immunofluorescence for AR performed. Nucleus was stained with DAPI.

SARDs Inhibit Recruitment of AR to the Promoter and Enhancer Elements of Androgen Responsive Genes LNCaP cells were serum starved for 3 days and treated as indicated above with SARD (compound 17) or bicalutamide at 10 uM in the presence or absence of 0.1 nM R1881. Proteins were cross-linked to DNA and chromatin immunoprecipitation studies were conducted with AR and RNA-Pol II antibodies. 17 inhibited recruitment to the promoter or enhancer elements of androgen responsive genes such as PSA, FKBP, and TMPRSS2 (FIG. 7A). SARDs degrade AR. LNCaP cells were serum starved for 3 days and treated as indicated above with SARD (17) at 10 uM in the presence or absence of 0.1 nM R1881. Cells were fixed and immunofluorescence for AR performed. Nucleus was stained with DAPI. SARDs did not abrogate AR translocation to the nucleus but did decrease levels of AR in the nucleus upon treatment with an agonist R1881 (FIG. 7B).

Example 10

SARDs Inhibited LNCaP Cell Growth by Non-Competitive Binding to AR

Figure 8:
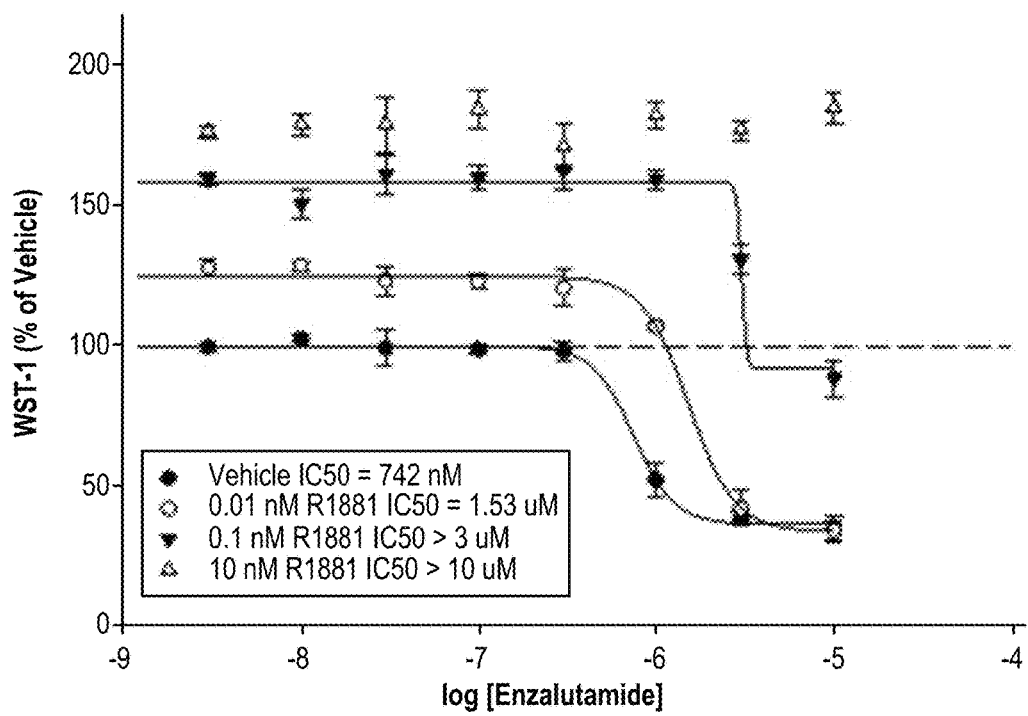
FIG. 8 depicts that SARDs inhibit LNCaP cell growth by non-competitive binding of AR. LNCaP cells were plated in serum free medium and were treated with increasing concentrations of enzalutamide or compound 17 in the presence of a dose range of R1881. Seven days after treatment, cells were fixed and growth measured by WST-1 assay.
Figure 8:
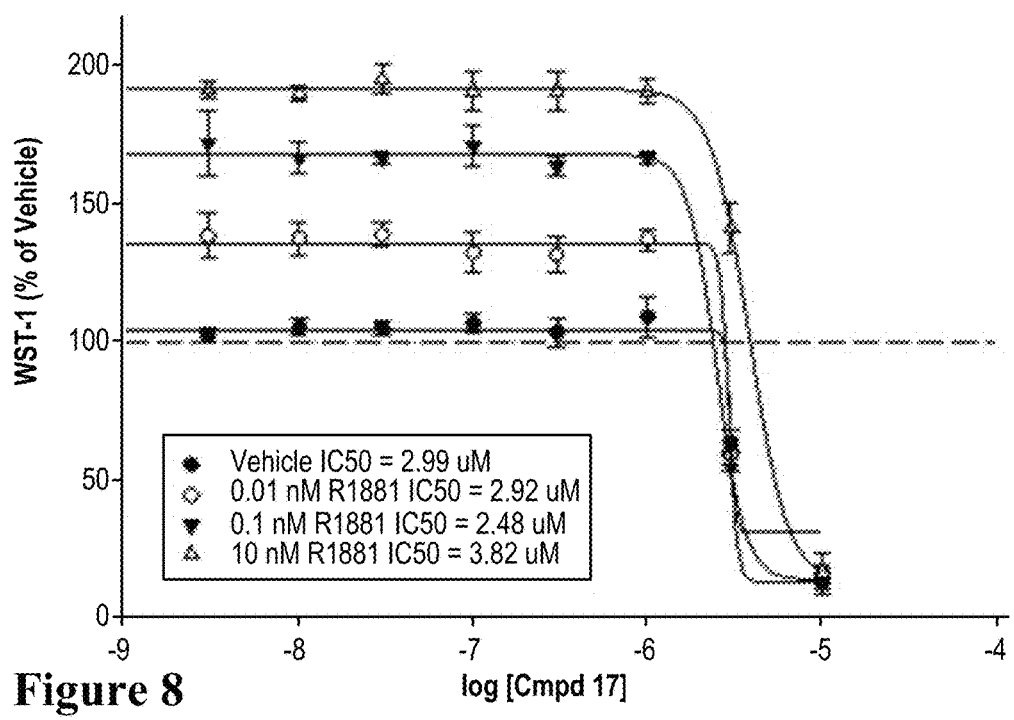

LNCaP cells were plated in serum free medium and were treated with increasing concentrations of enzalutamide or 17 in the presence of a dose range of R1881. Seven days after treatment, cells were fixed and growth measured by WST-1 assay. SARDs inhibited LNCaP cell growth by an apparent non-competitive binding to AR (FIG. 8). As expected, enzalutamide $IC_{50}$ values for cell growth inhibition increased with increased amounts of R1881. However, the $IC_{50}$ values for cell growth inhibition for 17 did not increase with amounts of R1881, possibly indicating that R1881 and 17 were not competing for the same binding site on AR.

Example 11

SARDs Bind to the AR-AF1

There are two tryptophan residues and up to 12 tyrosine residues in the AF1 of the AR. This has allowed the study of the folding properties of this domain using intrinsic steady state fluorescence emission spectra. Excitation at 287 nm excites both tyrosine and tryptophan residues. The emission maximum (Xmax) for the tryptophan is sensitive to the exposure to solvent. In the presence of the natural osmolyte TMAO there is a characteristic 'blue shift' consistent with the tryptophan residues being less solvent exposed and a loss of the shoulder (~307 nm) for tyrosine as there is increased energy transfer to tryptophan as the polypeptide folds. To test if the compounds, enobosarm (negative control), and 17 interact with AF-1 and/or alter the folding of this domain the steady state fluorescence was measured for each compound with AR-AF1 alone or the presence of TMAO (3 M) or urea (4 or 6 M). 1 µM of AR-AF1 and 5 µM of the individual compounds were used, and preincubated for at least 30 minutes prior to measuring the emission spectra. The emission spectra were all corrected for buffer alone or buffer with TMAO/urea/compounds as necessary.

Figure 11:
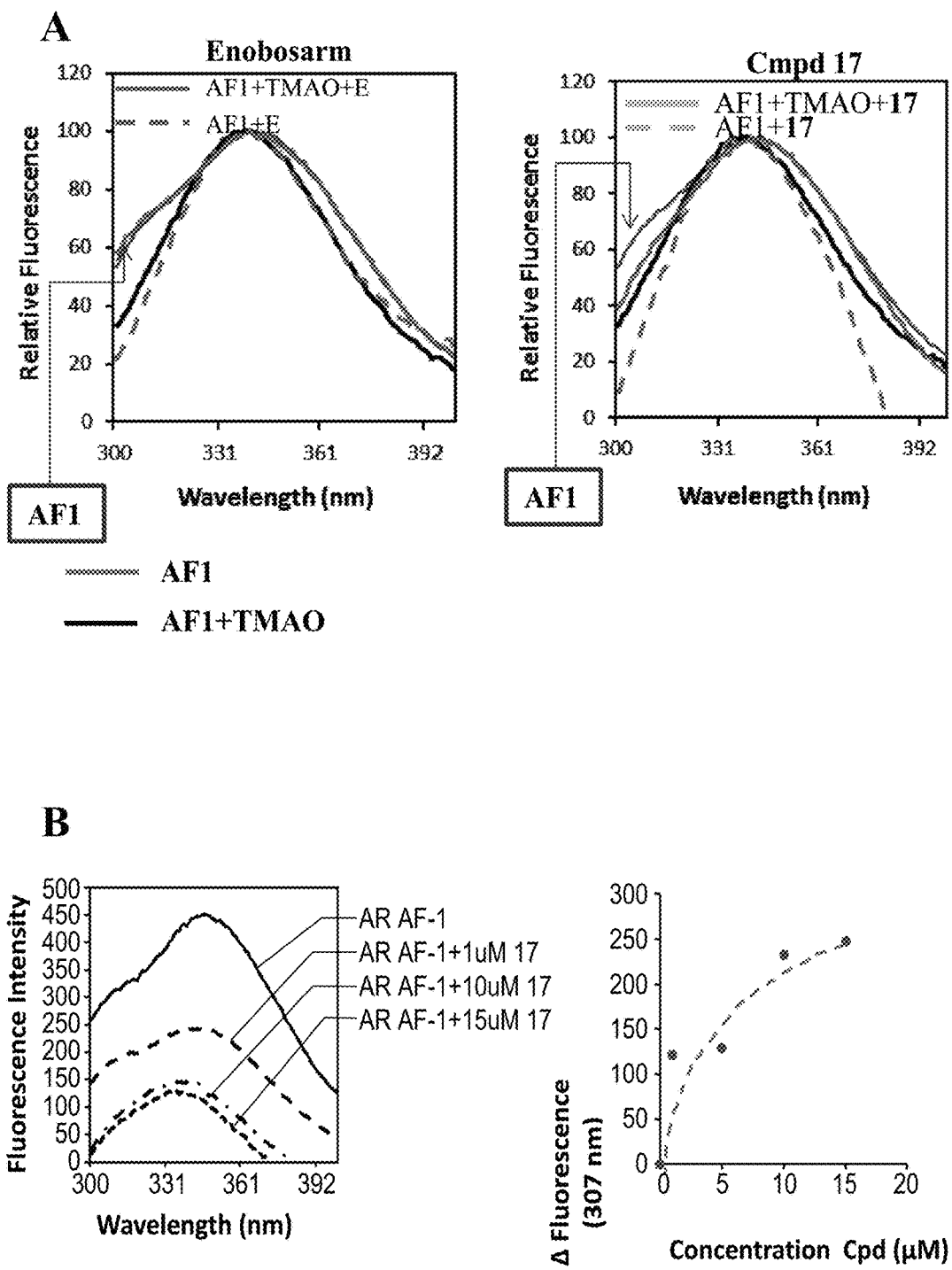
FIG. 11 depicts that SARDs bind to the N-terminal activation function 1 of AR (AR-AF1) in addition to the C-terminal ligand binding domain (LBD) which contains the AR-AF2.

FIG. 11 depicts that SARDs bind to the AR-AF1. FIG. 11A: The emission spectra were all corrected for buffer alone or buffer with TMAO/urea/compounds as necessary. There was no dramatic effect of enobosarm (left panel) on the $\lambda_{max}$ for tryptophan, while 17 (right panel) reduces the wavelength (i.e., a 'blue shift'), indicating that 17 binds to the AF-1 and enobosarm does not bind to AF-1. FIG. 11B: Left Panel: Dose-dependent shift in the fluorescence intensity, i.e., fluorescent quenching, by 17 when incubated with AR AF-1. The fluorescence shoulder observed at 307 nm, which corresponds to tyrosine residues in the AF-1, is shifted by 17. The overall fluorescence is also markedly altered by 17.

Right Panel: Data shown in the left panel was plotted as difference in fluorescence between control and compound 17 treated samples (fluorescence in the absence of compound—fluorescence in the presence of compound). A dose dependent increase was observed in the presence of 17 indicating interaction between 17 and AF1.

Example 12

AF1 Binding—External Validation (VIB)

Target Molecule:

Compound 17 was delivered dissolved in DMSO at 10 µM.

Experimental Setup

Purified H6-AF1 was biotinylated with N-hydroxysuccinimide (NHS)-PEG4-biotin at an estimated protein-biotylation ratio of 1:1. Bio-layer interferometry (BLI) was used to screen for binding of small molecule to biotinylated protein using the Octet 96RED system (FortéBio®). Biotinylated H6-AF1 was immobilized on super streptavidin (SSA) biosensors at full saturation level in order to detect signals from binding of small molecule. Biosensors loaded with AF1 were used in parallel to screen for binding of 17.

Results

Figure 12:
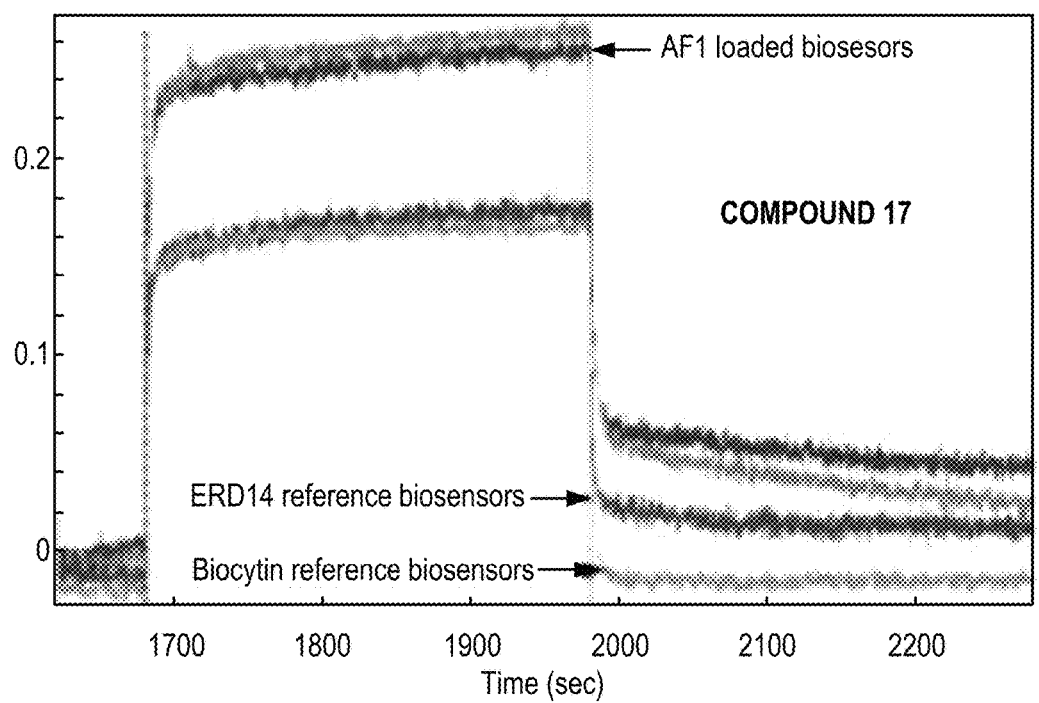
FIG. 12 depicts biolayer—interferometry (BLI) raw data measurements of AF1 binding to compound 17 at the concentration of 50 nM. The first 60 seconds are baseline (does not start at 0), followed by 300 seconds of an association and dissociation phase (~1650-1950 on y-axis). AF1 loaded biosensors are the top two traces. Addition of 17 to AF-1 loaded sheets causes a stronger shift as compared to controls loaded with ERD14 and biocytin (bottom two traces) as reference sensors suggesting that 17 has a direct interaction with AF-1 at concentrations as low as 50 nM.

Raw data measurements from binding of Compound 17 to AF1 are shown in FIG. 12. The data shows the AF1 loaded biosensors gave a stronger signal than any of the reference sensors at 50 nM concentrations. At higher concentration measurements were not possible because of the solubility issue with the compound.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A selective androgen receptor degrader (SARD) compound represented by the structure of formula I:

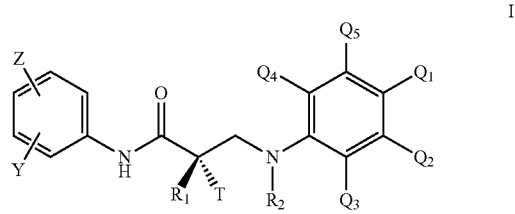

wherein

T is OH, OR, —NHCOCH$_3$, or NHCOR;

Z is NO$_2$, CN, COOH, COR, NHCOR or CONHR;

Y is CF$_3$, F, I, Br, Cl, CN, C(R)$_3$ or Sn(R)$_3$;

R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH;

R$_1$ is CH$_3$, CH$_2$F, CHF$_2$, CF$_3$, CH$_2$CH$_3$, or CF$_2$CF$_3$;

R$_2$ is hydrogen, C$_1$-C$_{12}$-alkyl, —SO$_2$-aryl, —SO$_2$-phenyl, —CO-aryl, arylalkyl, benzyl, aryl, or C$_3$-C$_7$-cycloalkyl;

Q$_1$, Q$_4$, and Q$_5$ are each independently selected from hydrogen, substituted or unsubstituted linear or branched alkyl, substituted aryl, F, Cl, Br, I, CF$_3$, CN, NO$_2$, substituted or unsubstituted cycloalkyl, substituted or unsubstituted heterocycloalkyl, substituted or unsubstituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO, or OCN;

Q$_2$ and Q$_3$, are each independently selected from hydrogen, substituted or unsubstituted linear or branched alkyl, substituted aryl, F, Cl, Br, I, CF$_3$, CN, NO$_2$, substituted or unsubstituted cycloalkyl, substituted or unsubstituted heterocycloalkyl, substituted or unsubstituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO, or OCN;

wherein at least two of Q$_1$, Q$_2$, Q$_3$, Q$_4$, and Q$_5$ are not hydrogens; or Q$_1$ and Q$_2$ are joined together to form a substituted or unsubstituted C$_5$-C$_8$ carbocyclic or heterocyclic ring, and Q$_3$, Q$_4$, and Q$_5$ are as defined above; or Q$_2$ and Q$_3$ are joined together to form a substituted or unsubstituted C$_5$-C$_8$ non-aromatic carbocyclic ring or C$_5$-C$_8$ substituted or unsubstituted heterocyclic ring, and Q$_1$, Q$_4$, and Q$_5$ are as defined above; and wherein said formed carbocyclic or heterocyclic ring is not dihydropyridin-2(1H)-one, pyridin-2(1H)-one or 1H-pyrrole.

2. The SARD compound according to claim 1, represented by the structure of formula III:

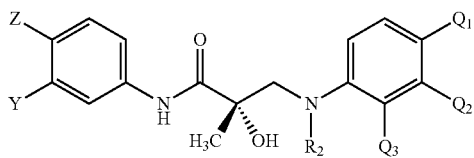

wherein
  Z is $NO_2$ or CN;
  Y is $CF_3$, F, I, Br, Cl, or CN;
  $R_2$ is hydrogen, $C_1$-$C_{12}$-alkyl, —$SO_2$-aryl, —$SO_2$-phenyl, —CO-aryl, substituted or unsubstituted arylalkyl, substituted or unsubstituted benzyl, substituted or unsubstituted aryl, or substituted or unsubstituted $C_3$-$C_7$-cycloalkyl;
  $Q_1$ is selected from hydrogen, substituted or unsubstituted aryl, substituted or unsubstituted phenyl, substituted or unsubstituted arylalkyl, F, Cl, Br, I, $CF_3$, CN, $NO_2$, substituted or unsubstituted cycloalkyl, or substituted or unsubstituted heterocycloalkyl;
  $Q_2$ and $Q_3$ are each independently selected from hydrogen, substituted or unsubstituted aryl, substituted or unsubstituted phenyl, substituted or unsubstituted arylalkyl, F, Cl, Br, I, $CF_3$, CN, $NO_2$, substituted or unsubstituted cycloalkyl, or substituted or unsubstituted heterocycloalkyl;
  wherein at least one of $Q_1$, $Q_2$ and $Q_3$ is a substituted aryl, substituted or unsubstituted arylalkyl, or substituted phenyl;
  or
  $Q_1$ and $Q_2$ are joined together to form a substituted or unsubstituted $C_5$-$C_8$ carbocyclic or heterocyclic ring and $Q_3$ is as defined above;
  or
  $Q_2$ and $Q_3$ are joined together to form a substituted or unsubstituted $C_5$-$C_8$ non-aromatic carbocyclic ring or a $C_5$-$C_8$ heterocyclic ring and $Q_1$ is as defined above; and
  wherein said formed carbocyclic or heterocyclic ring is not dihydropyridin-2(1H)-one, pyridin-2(1H)-one or 1H-pyrrole.

3. The SARD compound of claim 1, wherein $Q_1$ is CN.

4. The SARD compound of claim 1 wherein $Q_2$ and $Q_3$ are joined together to form a substituted or unsubstituted $C_5$-$C_8$ non-aromatic carbocyclic or a substituted or unsubstituted $C_5$-$C_8$ heterocyclic ring.

5. The SARD compound of claim 1, represented by the structure of any one of the following compounds:

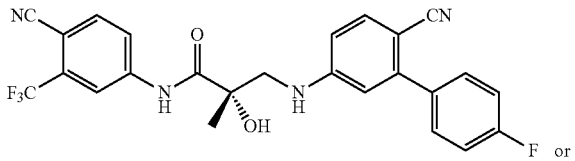

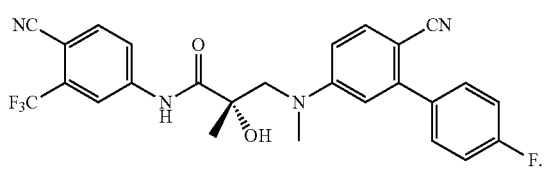

6. A pharmaceutical composition comprising a SARD compound according to claim 1, or its isomer, pharmaceutically acceptable salt, pharmaceutical product, polymorph, hydrate or any combination thereof, and a pharmaceutically acceptable carrier.

7. The pharmaceutical composition of claim 6, wherein said composition is formulated for topical use.

8. The pharmaceutical composition of claim 7, wherein said composition is in the form of a solution, lotion, salve, cream, ointment, liposome, spray, gel, foam, roller stick, cleansing soap or bar, emulsion, mousse, aerosol, shampoo, or any combination thereof.

9. A method of treating, suppressing, reducing the incidence, reducing the severity, or inhibiting the progression of prostate cancer (PCa) and its symptoms, or increasing the survival of a male subject suffering from prostate cancer comprising administering to said subject a therapeutically effective amount of a compound according to claim 1, or its isomer, pharmaceutically acceptable salt, pharmaceutical product, polymorph, hydrate or any combination thereof.

10. The method of claim 9, wherein the prostate cancer is advanced prostate cancer, castration resistant prostate cancer (CRPC), metastatic CRPC (mCRPC), non-metastatic CRPC (nmCRPC), high-risk nmCRPC or any combination thereof.

11. The method of claim 9, wherein said subject further receives androgen deprivation therapy (ADT).

12. The method of claim 9, wherein said subject has failed androgen deprivation therapy (ADT).

13. The method of claim 9, wherein said cancer is resistant to treatment with an androgen receptor antagonist.

14. The method of claim 9, wherein said administering reduces the levels of AR, AR-full length (AR-FL), AR with antiandrogen resistance-conferring AR-LBD mutations, AR-splice variant (AR-SV), or any combination thereof, in said subject.

15. A method of treating, suppressing, reducing the incidence, reducing the severity, or inhibiting the progression of acne in a subject, comprising administering to said subject a therapeutically effective amount of the compound of claim 1, or its isomer, pharmaceutically acceptable salt, pharmaceutical product, polymorph, hydrate or any combination thereof.

16. The method of claim 15, wherein said acne is acne vulgaris.

17. A method of decreasing sebum production in a subject, comprising administering to said subject a therapeutically effective amount of a compound of claim 1, or its isomer, pharmaceutically acceptable salt, pharmaceutical product, polymorph, hydrate or any combination thereof.

18. The method of claim 17, wherein said subject suffers from a dermal disease.

19. The method of claim 18, wherein said dermal disease is seborrhea, seborrheic dermatitis, acne, or any combination thereof.

20. The method of claim 18, wherein said subject suffers from overactive sebaceous glands and/or is during the age of puberty.

21. A method of treating, suppressing, reducing the incidence, reducing the severity, or inhibiting the progression of hirsutism in a subject, comprising administering to said subject a therapeutically effective amount of a compound of claim 1, or its isomer, pharmaceutically acceptable salt, pharmaceutical product, polymorph, hydrate or any combination thereof.

22. A method of treating, suppressing, reducing the incidence, reducing the severity, or inhibiting the progression of alopecia in a subject, comprising administering to said subject a therapeutically effective amount of a compound of claim 1, or its isomer, pharmaceutically acceptable salt, pharmaceutical product, polymorph, hydrate or any combination thereof.

23. The method of claim 22, wherein said alopecia is androgenic alopecia, alopecia areata, alopecia secondary to chemotherapy, alopecia secondary to radiation therapy, alopecia induced by scarring, alopecia induced by stress or any combination thereof.

24. The method of claim 22, wherein said composition is applied topically to the scalp and/or hair.

25. A method of treating, suppressing, reducing the incidence, reducing the severity, or inhibiting the progression of a hormonal condition in a female, comprising administering to said subject a therapeutically effective amount of a compound of claim 1, or its isomer, pharmaceutically acceptable salt, pharmaceutical product, polymorph, hydrate or any combination thereof.

26. The method of claim 25, wherein said hormonal condition is precocious puberty, early puberty, dysmenorrhea, amenorrhea, multilocular uterus syndrome, endometriosis, hysteromyoma, abnormal uterine bleeding, early menarche, fibrocystic breast disease, fibroids of the uterus, ovarian cysts, polycystic ovary syndrome, pre-eclampsia, eclampsia of pregnancy, preterm labor, premenstrual syndrome, and/or vaginal dryness.

27. A method of treating, suppressing, reducing the incidence, reducing the severity, or inhibiting the progression of sexual perversion, hypersexuality, or paraphilias in a subject, comprising administering to said subject a therapeutically effective amount of the compound of claim 1, or its isomer, pharmaceutically acceptable salt, pharmaceutical product, polymorph, hydrate or any combination thereof.

28. A method of treating, suppressing, reducing the incidence, reducing the severity, or inhibiting the progression of androgen psychosis in a subject, comprising administering to said subject a therapeutically effective amount of the compound of claim 1, or its isomer, pharmaceutically acceptable salt, pharmaceutical product, polymorph, hydrate or any combination thereof.

29. A method of treating, suppressing, reducing the incidence, reducing the severity, or inhibiting the progression of virilization in a subject, comprising administering to said subject a therapeutically effective amount of the compound of claim 1, or its isomer, pharmaceutically acceptable salt, pharmaceutical product, polymorph, hydrate or any combination thereof.

30. A method of treating, suppressing, reducing the incidence, reducing the severity, or inhibiting the progression of androgen insensitivity syndrome in a subject, comprising administering to said subject a therapeutically effective amount of the compound of claim 1, or its isomer, pharmaceutically acceptable salt, pharmaceutical product, polymorph, hydrate or any combination thereof.

31. A method of increasing, modulating, or improving ovulation in an animal, comprising administering to said animal a therapeutically effective amount of the compound of claim 1, or its isomer, pharmaceutically acceptable salt, pharmaceutical product, polymorph, hydrate or any combination thereof.

32. A method of treating, suppressing, reducing the incidence, reducing the severity, or inhibiting the progression of cancer in a subject, comprising administering to said subject a therapeutically effective amount of the compound of claim 1, or its isomer, pharmaceutically acceptable salt, pharmaceutical product, polymorph, hydrate or any combination thereof.

33. The method of claim 32, wherein said cancer is breast cancer, testicular cancer, uterine cancer, ovarian cancer, urogenital cancer, brain cancer, skin cancer, lymphoma, liver cancer, renal cancer, osteosarcoma, pancreatic cancer, endometrial cancer, lung cancer, non-small cell lung cancer (NSCLC), colon cancer, perianal adenoma, central nervous system cancer, or any combination thereof.

34. A method of reducing the levels of polyglutamine (polyQ) AR polymorphs in a subject, comprising administering to said subject a therapeutically effective amount of a compound according to claim 1, or its isomer, pharmaceutically acceptable salt, pharmaceutical product, polymorph, hydrate or any combination thereof.

35. The method according to claim 34, wherein said reduction is achieved by degradation, inhibition, or dual degradation and inhibitory function of said polyglutamine (polyQ) AR polymorphs (polyQ-AR).

36. The method according to claim 34, wherein said polyQ-AR is a short polyQ polymorph or a long polyQ polymorph.

37. The method according to claim 34, wherein the polyQ-AR is a short polyQ polymorph, and said method further treats dermal disease.

38. The method of claim 37, wherein said dermal disease is seborrhea, seborrheic dermatitis, acne, or any combination thereof.

39. The method according to claim 34, wherein the polyQ-AR is a long polyQ polymorph, and said method further treats Kennedy's disease.

40. A method of treating, suppressing, reducing the incidence, reducing the severity, or inhibiting the progression of uterine fibroids in a subject, comprising administering to said subject a therapeutically effective amount of the compound of claim 1, or its isomer, pharmaceutically acceptable salt, pharmaceutical product, polymorph, hydrate or any combination thereof.

41. A selective androgen receptor degrader (SARD) compound of formula 17, 20, or 21:

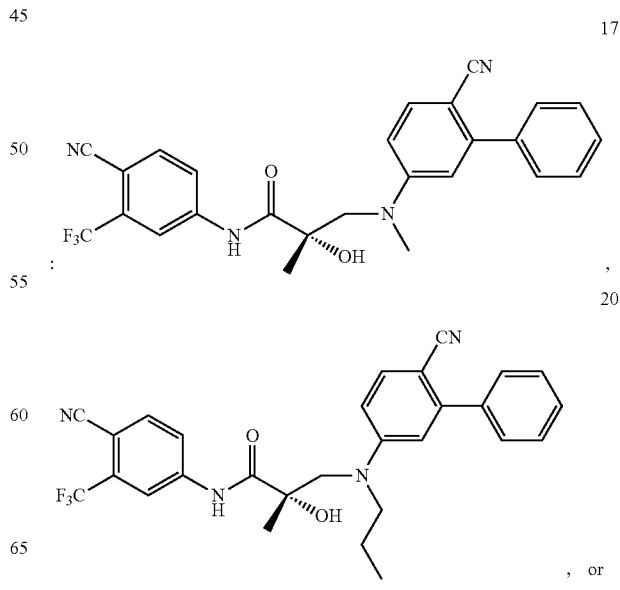

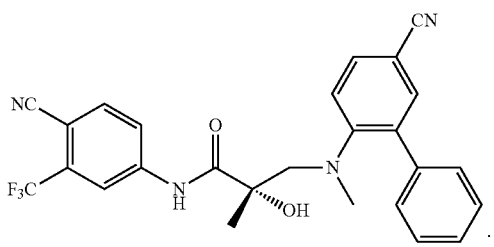

42. A pharmaceutical composition comprising a SARD compound according to claim 41, or its isomer, pharmaceutically acceptable salt, pharmaceutical product, polymorph, hydrate or any combination thereof, and a pharmaceutically acceptable carrier.

43. A method of treating, suppressing, reducing the incidence, reducing the severity, or inhibiting the progression of prostate cancer (PCa) and its symptoms, or increasing the survival of a male subject suffering from prostate cancer comprising administering to said subject a therapeutically effective amount of a compound according to claim 41, or its isomer, pharmaceutically acceptable salt, pharmaceutical product, polymorph, hydrate or any combination thereof.

44. The method of claim 43, wherein the prostate cancer is advanced prostate cancer, castration resistant prostate cancer (CRPC), metastatic CRPC (mCRPC), non-metastatic CRPC (nmCRPC), high-risk nmCRPC or any combination thereof.

45. The method of claim 43, wherein said subject further receives androgen deprivation therapy (ADT).

46. The method of claim 43, wherein said subject has failed androgen deprivation therapy (ADT).

47. The method of claim 43, wherein said cancer is resistant to treatment with an androgen receptor antagonist.

48. A method of treating, suppressing, reducing the incidence, reducing the severity, or inhibiting the progression of acne in a subject, comprising administering to said subject a therapeutically effective amount of the compound of claim 41.

49. A method of decreasing sebum production in a subject, comprising administering to said subject a therapeutically effective amount of a compound of claim 41, or its isomer, pharmaceutically acceptable salt, pharmaceutical product, polymorph, hydrate or any combination thereof.

50. A method of treating, suppressing, reducing the incidence, reducing the severity, or inhibiting the progression of hirsutism in a subject, comprising administering to said subject a therapeutically effective amount of a compound of claim 41, or its isomer, pharmaceutically acceptable salt, pharmaceutical product, polymorph, hydrate or any combination thereof.

51. A method of treating, suppressing, reducing the incidence, reducing the severity, or inhibiting the progression of alopecia, hormonal condition in a female, of sexual perversion, hypersexuality, or paraphilias, androgen psychosis, virilization in a subject, androgen insensitivity syndrome or cancer in a subject, comprising administering to said subject a therapeutically effective amount of a compound of claim 41, or its isomer, pharmaceutically acceptable salt, pharmaceutical product, polymorph, hydrate or any combination thereof.

52. A method of increasing, modulating, or improving ovulation in an animal, comprising administering to said animal a therapeutically effective amount of the compound of claim 41, or its isomer, pharmaceutically acceptable salt, pharmaceutical product, polymorph, hydrate or any combination thereof.

53. A method of reducing the levels of polyglutamine (polyQ) AR polymorphs in a subject, comprising administering to said subject a therapeutically effective amount of a compound according to claim 41, or its isomer, pharmaceutically acceptable salt, pharmaceutical product, polymorph, hydrate or any combination thereof.

54. A method of treating, suppressing, reducing the incidence, reducing the severity, or inhibiting the progression of uterine fibroids in a subject, comprising administering to said subject a therapeutically effective amount of the compound of claim 41, or its isomer, pharmaceutically acceptable salt, pharmaceutical product, polymorph, hydrate or any combination thereof.

55. The pharmaceutical composition of claim 42, wherein said composition is formulated for topical use.

56. The method of claim 51, wherein said cancer is breast cancer, testicular cancer, uterine cancer, ovarian cancer, urogenital cancer, brain cancer, skin cancer, lymphoma, liver cancer, renal cancer, osteosarcoma, pancreatic cancer, endometrial cancer, lung cancer, non-small cell lung cancer (NSCLC), colon cancer, perianal adenoma, central nervous system cancer, or any combination thereof.

* * * * *